(12) United States Patent
Wu et al.

(10) Patent No.: US 6,818,446 B2
(45) Date of Patent: Nov. 16, 2004

(54) COMPOSITIONS AND METHODS FOR THE ANALYSIS OF MUCIN GENE EXPRESSION AND IDENTIFICATION OF DRUGS HAVING THE ABILITY TO INHIBIT MUCIN GENE EXPRESSION

(75) Inventors: Reen Wu, Davis, CA (US); Yin Chen, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 127 days.

(21) Appl. No.: 09/990,613

(22) Filed: Nov. 21, 2001

(65) Prior Publication Data

US 2003/0096219 A1 May 22, 2003

(51) Int. Cl.$^7$ .......................... C12N 15/74; C07H 21/04
(52) U.S. Cl. ................... 435/320.1; 536/23.1; 536/24.1
(58) Field of Search ...................... 435/320.1; 536/23.1, 536/24.1

(56) References Cited

U.S. PATENT DOCUMENTS

| 6,136,539 A | 10/2000 | Basbaum et al. ............... 435/6 |
| 6,270,747 B1 | 8/2001 | Nadel et al. ................... 424/9.2 |

FOREIGN PATENT DOCUMENTS

| JP | 9012473 A2 | 1/1997 |
| WO | WO 99/41270 | 8/1999 |
| WO | WO 00/04142 | 1/2000 |
| WO | WO 01/54685 A1 | 8/2001 |

OTHER PUBLICATIONS

Chen et al, Gene Bank Accession No. AF107890, Released Nov. 22, 2000 IDS/14.*
Bernacki et al., "Mucin Gene Expression during Differentiation of Human Airway Epithelia In Vitro. MUC4 and MUC5B are Strongly Induced," *American Journal of Respiratory Cell and Molecular Biology*, 20(4) 595–604 (1999).
Chen et al., "Characterization of human MUC5B gene expression in airway epithelium and the genomic clone of the amino–terminal and 5'–flanking region," *American Journal of Respiratory Cell and Molecular Biology*, 25(5):542–553 (Nov., 2001).
Clavereau et al., "Transfection of various carcinoma cell lines using Effectene™ reagent," in *Qiagen News—Customer Application Guide*. Issue No. 1 (2000).
Davies et al., "Identification of MUC5B, MUC5AC and small amounts of MUC2 mucins in cystic fibrosis airway secretions," *Biochemical Journal*, 344 (Pt 2) (4697): 321–330 (1990).
Desseyn et al., "Genomic organization of the 3' region of the human mucin gene MUC5B," *J. Biol. Chem.*, 272(27):16873–16883 (Jul. 4, 1997).
Desseyn et al., "Genomic organization of the human mucin gene MUC5B," *J. Biol. Chem.*, 273(46): 30157–30164 (Nov. 13, 1998).

Desseyn et al., "Human mucin gene MUC5B, the 10.7–kb large central exon encodes various alternate subdomains resulting in a super–repeat," *The Journal of Biological Chemistry*, 272(6):3168–3178 (Feb. 7, 1997).
GenBank Accession No. AF107890, Chen et al., Homo sapiens mucin 5B (MUC5B) gene, partial cds. Released Nov. 22, 2000.
GenBank Accession No. AJ012453, Vanseuningen, Homo sapiens MUC5B gene proximal 5' flanking region. Released May 3, 2001.
GenBank Accession No. U67167, Gum et al., Homo sapiens intestinal mucin (MUC2) gene, promoter region and partial cds. Released Jul. 9, 1997.
GenBank Accession No. X74955, Laine, H. sapiens MUC5B mRNA (clone JER57) for mucin (partial). Released Jun. 12, 1996.
GenBank Accession No. Z48314, Lesuffleur, H. sapiens mRNA for apomucin. Released Aug. 2, 1995.
GenBank Accession No. Z72496, Laine, H. sapiens MUC5B gene (partial) Released Aug. 20, 1997.
GenBank Accession No. AJ004862, Laine, Homo sapiens partial MUC5B gene, exon 1–29. Released Mar. 10, 2000.
GenBank Accession No. AJ011582, Laine, Homo sapiens MUC5B gene, 5'UTR. Released Jul. 14, 2000.
Hovenberg et al., "Different mucins are produced by the surface epithelium and the submucosa in human trachea: identification of MUC5AC as a major mucin from the goblet cells," *Biochem. J.*, 318(Pt. 1, vol. 17):319–324 (1996).
Hovenberg et al., "MUC5AC, but not MUC2, is a prominent mucin in respiratory secretions," *Glycoconjugate Jour.*, 13(5) 839–847 (1996).
Jany, et al., "Modification of Mucin Gene Expression in Airway Disease," *Am. Rev. Respir. Dis.*, 144(3 Pt 2) S38–41 (1991).
Kaliner et al., "Pulmonary Perspective Human Respiratory Mucus," *American Review of Respiratory Disease*, 134(3):612–621 (1986).
Ke et al., "Human brocchial epithelial cells with integrated SV40 virus T antigen genes retain the ability to undergo squamous differentiation," *Differentiation*, 38(1):60–66 (1988).

(List continued on next page.)

*Primary Examiner*—Anne M. Wehbe'
*Assistant Examiner*—Q. Janice Li
(74) *Attorney, Agent, or Firm*—Ginger R. Dreger; Heller Ehrman White & McAuliffe LLP

(57) ABSTRACT

The invention relates to compositions and methods for the assessment of mucin gene expression. The invention also relates to compositions and methods for the identification of compounds useful in the treatment of various disorders caused by mucin overproduction. The invention provides novel MUC5B promoter sequences and reporter constructs comprising these MUC5B promoter sequences. The invention further provides methods for drug screening to identify compounds have the ability to inhibit MUC5B gene expression. Compounds having the ability to inhibit MUC5B gene expression find use in the treatment of diseases characterized by mucin hyperproduction.

4 Claims, 25 Drawing Sheets

OTHER PUBLICATIONS

Keates et al., "Molecular cloning of a major human gall bladder mucin: complete C–terminal sequence and genomic organization of MUC5B," *Biochem. J.*, 324(Pt 1):295–303 (1997).

Koo et al., "Restoration of the Mucous Phenotype by Retinoic Acid in Retinoid–Deficient Human Bronchial Cell Cultures: Changes in Mucin Gene Expression," *American Journal of Respiratory Cell and Molecular Biology*, 20(1):43–52 (1999).

Lesuffleur et al., "Differential expression of the human mucin genes MUC1 to MUC5 in relation to growth and differentiation of different mucus–secreting HT–29 cell subpopulations," *J. of Cell Science*, 106:771–783 (1993).

Lesuffleur et al., "Mucins in normal and neoplastic human gastrointestinal tissues," *Crit. Rev. Oncol. Hematol.*, 17(3):153–180 (1994).

Louahed et al., "Interleukin–9 upregulates mucus expression in the airways," *Am. J. Respir. Cell Mol. Biol.*, 22:649–656 (2000).

Meerzaman et al., "Cloning and Analysis of cDNA Encoding a Major Airway Glycoprotein, Human Tracheobronchial Mucin (MUC5)," *Jour. Biol. Chem.*, 269(7):12932–12939 (1994).

Offner et al., "The amino–terminal sequence of MUC5B contains conserved multifunctional D domains: Implications for tissue–specific mucin functions," *Biochem. Biophys. Res. Commun.*, 251(1):350–355 (1998).

Perrais et al., "Aberrant expression of human mucin gene MUC5B in gastric carcinoma and cancer cells; identification and regulation of a distal promoter," *J. Biol. Chem.*, 276(18):15386–15396 (May 4, 2001).

Pigny et al., "Human Mucin Genes Assigned to 11p15.5: Identification and Organization of a Cluster of Genes," *Genomics*, 38(3):340–352 (1996).

Pigny et al., "Identification of a 42–kDa nuclear factor (NF1–MUC5B) from HT–29 MTX cells that binds to the 3' region of human mucin gene MUC5B," *Biochem. Biophys. Res. Commun.*, 220(1):186–191 (1996).

Poster Presentation: Chen et al., "Differential mucin gene expression and regulation in cultures of conducting airway epithelial cells," American Thoracic Society / American Lung Association International Conference, San Diego, CA (Apr. 23–28, 1999), Abstract A22 [Poster: 604].

Reid et al., "Developmental Expression of Mucin Genes in the Human Respiratory Tract," *Am. J. Respir. Cell Mol. Biol.*, 17:592–598 (1997).

Robinson et al., "Culture of Conducting Airway Epithelial Cells," *J. Tiss. Cult Meth.*, 13:95–102 (1991).

Rogers et al., "Airway goblet cells: responsive and adaptable front–line defenders," *Eur. Respir. J.*, 7(9): 1690–706 (1994).

Sheehan et al., "Physical characterization of a low–charge glycoform of the MUC5B mucin comprising the gel–phase of an asthmatic respiratory mucous plug," *Biochemical Journal*, 338(Pt 2)(7):507–513 (1999).

Thornton et al., "Identification of two glycoforms of the MUC5B mucin in human respiratory mucus," *J. Biol. Chem.*, 272(14) 9561–9566 (1997).

Van Seuningen et al., "Sequence of the 5'–flanking region and promoter activity of the human mucin gene MUC5B in different phenotypes of colon cancer cells," *Biochem J.*, 348(Pt 3):675–686 (Jun. 15, 2000).

Wickström et al., "MUC5B is a major gel–forming, oligomeric mucin from human salivary gland, respiratory tract and endocervix; identification of glycoforms and C–terminal cleavage," *Biochem. Jour.*, 334(Pt. 3)(14):685–693 (1998).

Wu et al., "Growth and differentiation of conducting airway epithelial cells in culture," *European Respiratory Journal*, 10(10):2398–2403 (1997).

Yanagihara et al., "Lipopolysaccharide Induces Mucus Cell Metaplasia in Mouse Lung," *Am. J. Respir. Cell. Mol. Biol.*, 24(1):66–73 (2001).

Yankaskas et al., "Papilloma virus immortalized tracheal epithelial cells retain a well–differentiated phenotype," *Am. J. Physiol.*, 264:C1219–C1230 (1993).

\* cited by examiner

```
   1 ggtacccctg gttgtgcctg tcgctcagtg ggccagggtc taagggctgt gaagactcaa
  61 catgccccca cctgctactt ctgaacacca ggcactggct ctgagacccc cgggccttgc
 121 tggacatctc cccaggtgta ctgggccagg ggacaggggc ctggccatcc caacacccag
 181 gagcaagcag cccgtcacct gcccaggtcc ccgaggcccg gaacaccttc ctgctgggcc
 241 cacccagccc tggacctgtc ccgcttggtc acacgatggg accctcggcc catcagcagg
 301 tgagccccca ggagcgtgcg tctggcctgg taaggcctcc accccaggag ttgggggcc
 361 cccgtgccag ggagcaggag gctgccagg tggaggtcc cacacagcta ccactcccta
 421 tccccagcac agcctgggc ctggctctga gtacacatcc tggggcctgg ctctgagcag
 481 accaagagcc catccctgct tgtgacccc ctgggctgtg cctgacaccc caggtgtcca
 541 gcgtggagct ggggcccagc tcagtgcctg ggagctgatg gacctgggg cccggctcag
 601 tgcctggtgg ctgatggaca ctggggcctg gctcaaacct gcaccgctgt ggtcggggga
 661 ggggagggct gagccacgtg gggaacccag ccccagtgac gactctttgc ggtggccaag
 721 ccctccaggt gtccccagg gctgaggggc tgggcttggg gcagctggtg acagcagatg
 781 gtggccctga tcactggtgc ctggacggcc tctgaagggg tctgtggggt cctggacggg
 841 tccccattca tggcaggatt aaccccctc gggttctgtg tggtccaggc cgccccttttg
 901 tctccactgc ccctggcca gaatgaggga cagtgaccca ccagggctg ggcctggctc
 961 agactccgtc agagccgcag ggcaagttcc tggcacgtcc gaggtgggag gctcctctgc
1021 gctccaggag gctgtgcctg gccccccttc ccggcaggaa ccggctgtgt cccttttcctt
1081 cctttatctt ctgtttcag cgccttcaac tgtgaagagg tgaactcttc aaacacgctg
1141 agcaaacagg cccgactccc agggccgcat ccgggatgtc tcaatagctg tggccttgac
1201 gtccacctcg gacccctgcc ccggacccag cccagttccc aatgggccct ctgcccgggg
1261 aggtgcctag tgggagggac gagggcaaag tcggggcccc cacttgtttg gtgtcactgt
1321 gtgccagcgg ccactggcgg gcgaggctgt tccagggtgg aggcggggag ggttggacca
1381 caggcactga gcggggacag aggagctgcc tgagggtccc agctctgcca tggagaaaac
1441 gctatctcgc tgatgcagag gtgcccggcc cactcgagct ggggtgagg gggctgctcc
1501 ccagtgggcc gccagccccc atgaaggccg cgggcaccgg ccgtggtcag ggagggcagg
1561 ggacaggcag tgggggccag caggggagac actaggcttg ccccagcac ccaggtgggc
1621 atcggcttgt gagctggagc cgcgggcagg gagggggat gtcacgaggg cttggctaag
1681 gtgggagacc tgggcgggtg cgtcggggg acgtctgcag cagaggcctg ggcagcaggc
1741 acacccctcc tgccagtgcg aggaacgagg cgccacagcg gccggtagcc ccccatttgc
1801 ccagcctggc ctggagcagg caggaaggcc ggggagaggg gtctggctgg ggcctgggtg
1861 cagtcacagc cacgagccca ggggtgggga ctctggccca cccttcagac catgctcaag
1921 gcccactggc ccaggcatgc ccgccacccc ttccaccgtg ccgtgctgca gcgggtctac
1981 cggcctggat gtgaaagaga gcttggagac cccagagacc tcggaacctt cagctttgga
2041 agtgacgtcg gtggggtggg tggggggagc acaggctctg gagtcccgga agtgagcggg
2101 gagctacgct gagatctggg agaccccctg ccccaccca ggtacagggc caggcagaag
2161 cccgaggtgt gccctgagtt aaagaaaccg tcacaaagaa caagggagaa aggcgggttc
2221 cagcctgcac cacagccctc gcgctctgag gagccacctg ggggcttcag ccatgagggg
2281 tgacaggtgg caaaacgggc cagctccgtt cacgtcgctg tgcagctgtc tccggccctc
2341 catctccaga acgttctcac attcccaagc tgaaaccctg tccccatgca acaccagctc
2401 accatcccct ctgccagccc ctggcgccca ccgtccacac tccgtctctg cgggtttcat
2461 gactccaggg gcagcacacg agtggcccct cctgcctttg tcctctgtgt ccacctgcct
2521 cactctgcac agtgtcccca gcttccccca tggagcagcc tgggccagcc cctccttttc
2581 acggctgaac cgtattccac cgcacggatc agcctcacga tgctgaccca gtcctccgcc
2641 cagggacaca tgggcagctt ctgcccttttg tcagtgatgc tgctgtggac atgggtgtgc
2701 aaatgtccct caggacccgc cttcagttct tctggggaca gacccagagt ggagttgctg
2761 gtcaccccca ccagcagggc acagggctcc gggtcccac gtctctgcca acacttccta
2821 cttcctgtgt ttcttgatcc ccgccatcct attgagcgtg agacaggtca gaagctttga
2881 agatgggctt tcgtcttgtc ccagaaatcc cacctctaag aatttaactt cagaaagaca
2941 aacgcggggg agctggtgca gggcccgtga cggggactgt gacgtaaata aaacaacaga
3001 cctggacacc accctagggt cccatggggg ccggacgagg ccacaccacc cgacctggtg
```

FIG. 6A

```
3061 cttcctgcct ggcgtctgcg ccacggagca ttcaggacgc tggtgaccag ggagccagga
3121 ggtgggagca tctgaggtgc aggtcacacg ggcaggaggt gtttgcaaga ggtattgcag
3181 cgcggacgga gtgtcctgca gatgacgctg tctgtcctgt agatgacgct cgtcaaggag
3301 ggctcccacc tggggcaggc ggaggacccc gggcaggtcc aggaccccca ggagcagctg
3361 cttcctcaac cctgccaggg ttaatgagga ggccccagag tgaggtggag gccaaatggg
3421 actcagggcc ggagcctctg gcctggctgg atcagggctg gcattggaca agcgcagctg
3481 actccgatg  tgcatggcca ggagacactc tgggcctcag tttccccttg aatgtgaacc
3541 ttgaaacaga tcagcccaga gacctccac  ggtcttcaag gggctctggt cagctgggct
3601 ggggtctctg gaaatagagc ctcctccagg gaccccaca  agccacccag actgagcatc
3661 ctggccatgt gcatgcctga gctcagcagg agcctgccgg gctcccgtg  ggctaagcag
3721 tggtgggagg ggagctccag cctcgtgggc cctgcccggg cctcggggac ccatggtcag
3781 tgctggggg  tgctgcccag aggctgggat tcccttccag caggagccgc agtggggctg
3841 agtgtgaggc aggctggctg accactgttt ccatggaccc tgcgtccaag gccagccctg
3901 ccttccagcg gctttgccat ctaggacggg tgccaggtgg ggtaggccct tctctccctt
3961 ccgattctca gaagctgctg ggggtggggg cgtcctgggc ctcagggcac agagctgcaa
4021 atccttcctg atccaggcct ctccctgcc  acagcccctc ccgagagca  aacacacgtg
4081 gctggagcgg ggaagagcac ggtgccctgc gtggcctggc ctggcttggg gccaaggctc
4141 cctgctacat aagctggggc ccccagggga gcaagcaccc ggcccggctc cctccctgcc
4201 cgtccccgtc ccccacccg  tgccagcccc caggatgggt gccccgagcg cgtgccggac
4261 gctggtgttg gctctggcgg ccatgctcgt ggtgccgcag gcaggtaaga gccccccact
4321 ccgcccccc  tcgatgctgt cttcacggcg ggggtctctg caggtcgctt gcctgggagc
4381 ttctcctgca gagtgcacgg gcagatcccc ctacgactcc ctgagtgtcc tggatgggac
4441 cctacccgtc cccaacacag ggctctgggg cccacgggc  tcacagtgtc aggaaactca
4501 ggggctggct tggatggggt gtccaggaga aggtgggccc ctgaccgcag ggcaaggccc
4561 ctgggagacc accgaaaggg tcttggtctt ggggtggga  caggagtggg caatggggga
4621 gggggtcaca gctggggtc  tctctggagc cccatgaggc ccaggcatca gagtgagcag
4681 gggcaggctt agcgtggacc cctgtccagg accggctcta cccttcacga cctccctggg
4741 gatcacagct ggcagggcag gtgagggtac ccgggaccct caagggttgc acagccagcc
4801 gcaagagccc cggcctcaac ccagcgctcga ctcccacggc ccatctgtgg gcatctcatg
4861 ccgcacgggc tgcctggctc tcagccgagc gttttccctc gtctgctgtc tcttggccag
4921 agccgcagca ttaatactta ctgtcaatag agaaagatgc agccccaggg gccaccggga
4981 gacacccagc caggctggcc atgaggctgc tgcagcccct ccctgccccg ccctccgccc
5041 cctcccaagc ttggggtctg ggctgggcag gtgaggttcc ctgggtctc  tctccatctg
5101 tggaagggag gctgggtggt cagcagggct ggaggcaggg ggcttccccc agtggctccc
5161 agcctgggcc cgggggagc  tgcgtctggc tgcaaggttt gggggctgtt ttgaccagaa
5221 tagccaccct cttgcatctg attcttccgg gccatgcagc cttggctccc ctcacctgag
5281 caggcaggc  ctagggactc tcagcccacc cgtcctcctg tcctccacgc acgtccaagt
5341 tggggagatc aagcccttgg cagggactgt gctttagtca ccagatgcac gtcctgtggc
5401 cggggaaggc agccctgcac agagcagctt catgttaggg gacacacccc aaagtgatgg
5461 ggtggctggt ggtgggcact tctctggcta caagatgag  gcccaggtgg tccagcccaa
5521 ggagggcact gcacggagca gataaccaag ggcagtcagc ctgggcaggg gagggggctgc
5581 ctggggggga ggggttgcct gggttgggga ggggctgtct ggggcagggg aggagctgcc
5641 tgggcgggg  gagggctgt  agggccaggg aggggctgcc tggggctggg gaggggctgc
5701 tggggtgggg aggggctgcc tgcggcggga gccggggcgt gggagtggct ggttgggctg
5761 gcacacaggg gcagggctgt gagctgtggg tcggggtgga ggactcaggg atcggctggc
5821 tttctgggaa aggcagtcaa cctggatctc tggaggcggc ccctgtggtg gttcccagat
5881 gtcagcagga cctggctgga aaagccaggc agggccaggc cagagtgcga accacagggc
5941 cggcccctcg ctgagccctg accatgcttg tggggctgg  ggcctcacct cccacctccc
6001 cacagagagt ctcagatcag gatccaggga ggagctctgg ggtcctgtga agggggcgcc
6061 ccaacccaaa ctgggcagac aatggccggg ggtcctcaga gtcctgtggg ttggagctgc
6121 ctcctcccag cctccatggg gttggtgggt gaggccttgc ccggaggcgg tggtcagcct
```

FIG. 6B

```
6181  gggggacctt  gggcggccat  cccagtatca  acggccacac  agcttgcgcg  gcccagagtc
6241  ctgccccag   cctgccccac  tcgccctgac  ttaggatcta  gttcgaaact  ggttctgtgt
6301  ttaggtttct  gctaagtcac  gcctggaagg  ctccaagtgt  gtcctcctaa  caaagctggt
6361  ctttgtcctt  ctccaaggga  tgtgtgggat  ggggcgaaat  ccccccttgg  ggcggccaac
6421  gccttttcct  gattccattt  tctccccat   cccttgagaa  ggaggcacca  tccccgcctg
6481  tcagtcgggg  acagggcagg  ccgtgctggg  ggcagctcag  ggctccctgc  tggaagcttc
6541  catcccgcag  gctttccata  gcattgagca  ggagcggagg  catctgcggc  tgacggttgg
6601  ggtggcctga  gcggctgggg  aggagtcccg  gccttggcca  cagtgtgtcg  tgagggtgaa
6661  cctgcagggc  atggagaccg  ccaccaagga  cccacatgc   ggctgccgca  ccagggatgt
6721  ggccaggtcc  gtggttgggt  tcgtggctgg  cagccacatc  tagttcctca  ctgactccca
6781  ttccctcttc  ccacagagac  ccagggccct  gtggagccga  gctggggaa   tgcagggcac
6841  accatggatg  gcggtatgtg  gccaggttcg  ggggtggggg  gttcctgacc  aggctggagg
6901  ggctggaatt  tgggctgggg  caggcagacg  cctctccaag  cagccatgcg  tctgacagag
6961  accctccctg  ggtcccctgc  ccaggacaat  acccagcacc  cgaggcggag  cttggtgctc
7021  caaagaagag  gaaagtgcag  agcagagaga  catgcacaca  gaagcacacg  cgtggacagg
7081  cacatgcgtg  cccacactta  cactggcaca  cacatgtgtg  cacacacagg  ccaaaacaca
7141  agggcagcag  tgtttgtggg  gcagacaggg  ccaagggtaa  aggggctgcc  ttggccccag
7201  cccatcagtt  ttgggctccc  cttcaactct  ggtggctggc  gaggagggtg  ggccccgggg
7261  agggtgtctc  tgcttcccct  tcctggccac  gttcctgggg  tgaccagcct  tcacccacag
7321  gtgccccgac  gtcctcgccc  acccggcgcg  tgagctttgt  tccacccgtc  actgtcttcc
7381  ccagcctgag  ccgtaagcag  atgctgcccc  tgccagccgg  gaaggggtg   tttgccagtc
7441  ccaaaggtgg  gggcccagat  ctaggggtgc  agctgccacc  aggtggggcc  gttgggccag
7501  acccagagtc  ctccgtgtgg  gcggtctcct  ggtcactggc  caccctgggg  gatggggacg
7561  ggtcagggt   cttggagcaa  aacagacgca  gtccagggtg  agccaggcag  ggcacagcca
7621  gcagccgacc  atgggctttt  ccattccaaa  aaccagggtg  cctcggccca  ggggaggcta
7681  ccccgtgggg  ggctggcatg  gggatgggcc  tcatcccgcg  ctccccacag  ccctgaaccc
7741  ggcgcacaat  gggcgggtgt  gcagcacctg  gggtgacttc  cactacaaga  ccttcgacgg
7801  cgacgtcttc  cgcttccctg  gcctttgcaa  ctacgtgttc  tctgagcact  gccgcgccgc
7861  ctacgaggac  ttcaacgtcc  agctacgccg  aggcctagtg  ggctccaggc  ctgtggtcac
7921  ccgtgttgtc  atcaaggccc  aggggctggt  gctgaaggcg  tccaacggct  ccgtcctcat
7981  caatgggcag  cggtgagccg  gccaccctgg  ggaggggcga  gggccgggcc  acacagtgtg
8041  acctccccac  acggccatgt  ctgacctggg  ccagggctgg  ggtggggttg  ggtgggcagg
8101  cagccaggag  agcggggccc  agggagagac  cccgctgtct  gcgcagggag  gagctgcctt
8161  acagccgcac  tggcctcctg  gtggagcaga  gcggggacta  catcaaggtc  agcatccggc
8221  tggtgctgac  attcctgtgg  aacgagagg   acagtgccct  ggtgaggaag  cccctcgcc
8281  ccttgcccct  tcaggcctgg  ccacaaaacc  cccaccgggg  gtcgagggat  gcctccctgg
8341  gcttggggtc  acggggcttg  gggcatgttg  ccagtggggg  gatcagaggt  cctgaggctg
8401  gagctgcccc  tccccactct  cagctggagc  tggatcccaa  atacgccaac  cagacctgtg
8461  gcctgtgtgg  ggacttcaac  ggcctcccgg  ccttcaacga  gttctatgcc  cacagtgagt
8521  gccacctggg  tgaggggcg   gtgaccaatt  atgtcggcca  acgaagagcc  acagtcccgg
8581  ggaggccggg  aggggcgga   gtggggaccg  ggcaccaggc  agggagggc   cacgaggact
8641  gtgccctaca  tggtgggagg  agtgccctc   ggggtgttg   ggcctaggc   aggagtggga
8701  gtcctctggc  ctgggctcag  gaagtgggag  cccatatctt  gtccccagga  gcccctcaga
8761  gccaccacac  ccctgctttc  ttcccggcag  acgccaggct  gaccccgctc  cagtttggga
8821  acctgcagaa  gttggatggg  cccacagagc  agtgcccgga  cccgctgccc  ttgccggccg
8881  gcaactgcac  ggacgaggtg  agtccccgc   cacccccagc  tcctgggcag  ggacggcctc
8941  caggtccagg  gggagctggg  ccgaggtctg  aggaatgttc  ccagctggtg  gagagatggt
9001  gccattggag  ggaggccggg  cagccaccct  ctgtgtgctc  agttccacgg  tacacactgt
9061  ccgagtgtgg  tgacgtgcgt  gttcatcagg  ccacgcgtgt  gcccatctgt  gtgagcaaac
9121  acaggcccat  gctgcacagg  ctgggctgag  ggtgggcact  cgggaagccc  ggagccagcc
9181  cttcccacca  gcaggtggac  tcagaagggg  cctggaggct  ccaggatccc  caaaccagca
```

FIG. 6C

```
 9241 ggatctctga gccttaaatt gtgctgtgaa tgacagcatg agccccctg tgagctgggc
 9301 cccgcagccg gcagccctgg gcctggggac ggaggacact cagcactgga ctgccctgaa
 9361 cctgccgggc tgcccagaga ggcggggcct ccacctcccc tccttggctc cgcctcctgg
 9421 ggtggggtc tgcacctttc ttgggcgctt actccacggg caggcacatc cggagtaggg
 9481 gatcccgggt tgacgggtca ctccccaagg gccaagcaga gctctgcatg ccacagtgg
 9541 gtggaagggg tggggctggg tacaaggaac cccgacaggg agagggcttc ccggcctggc
 9601 ctgccatggg tcctattcca gcaccgtggc agccccatg gatggcaggg gtgcccagcc
 9661 tggcccactg tgctccccag gagggcatct gccaccgcac cctgctgggg ccggcctttg
 9721 cggagtgcca cgcactggtg gacagcactg cgtacctggc cgcctgcgcc caggacctgt
 9781 gccgctgccc cacctgcccg tgtgccacct ttgtggaata ctcacgccag tgcgcccacg
 9841 cgggggggcca gccgcggaac tggaggtgcc ctgagctctg ccgtgagtgc tccagggcc
 9901 ttcgccaggg attgtgccag agagaagggg caggggagc gccttggggg ccactggggg
 9961 tggggaggcc tggggacag gggtggaggg cagaggaccc accccaggca tagtgggcag
10021 aggccacccc aggaccccag gagggggtgg ggccgccggg ggctgcaggg gaaggagagg
10081 cttgtggaga ggcttgtgca gcaggtggca ggggctgggg ctgagggtg tagctgccca
10141 cgatgagggg cgtcagggcc accctggggc ctagctctgg cttctgtgga cttgatggca
10201 tgtggaaggc cgtggaaggc ggctggggct gaccacacgg gcagtacagg gcccttcccc
10261 tggcccagcc ccgcctcctt ttgcgcagcc cggacctgcc cctcaacat gcagcaccag
10321 gagtgtggct caccctgcac ggacacctgc tccaacccccc agcgcgcgca gctctgcgag
10381 gaccactgtg tggacggctg cttctgcccc caggcagtg cttgtgtgcc ctgaaccct
10441 caggggctt tcaggtccct gctcccaacc ccgcccccag cctcatcagg cctggaagca
10501 gagcccctca tgccagaagg tccaccaga gggcccaggg tgggaagggc actggctggg
10551 agggtgctgg aagacctgcc gatgcgtgga gggaggtaga gcagtgccat gagccagctg
10621 ggcatggtgg ggaaactgag gcccagaggt gcttggtgtt catccaagcg agtgcagctc
10681 aggggcgggg cagtgtcctg gagcaggaat tcctccccaa gggaggcagc ttgtccccaa
10741 ggccggtgtc ttctgacctt ggtgtcccc gtgcatgggc cggcctgcc tcacgccgcg
10801 cccacaggc acggtgctgg atgacatcac gcactctggc tgcctgcccc tgggcagtg
10861 cccctgcacc cacggcggcc gcacctacag cccgggcacc tccttcaaca ccacctgcag
10921 ctcctggtac ttatgagccc accagcctcc gcctggggtg gggtgtggag ctcctggtat
10981 ttatgaaccc gccagcctct gcctggggtg ggggtgtgga gctcctggtg tgcacccacc
11041 agcctccgcc tgcggtgggg gtgtggaggg tggggcccac ctcctcccga catgccggtt
11101 ctgctcacgg cctccctccc cagcacctgc tcgggggggc tatggcagtg ccaggacctg
11151 ccgtgccctg gcacctgctc tgtgcagggc ggggcccaca tctccaccta tgatgagaaa
11221 ctctacgacc tgcatggtga ctgcagctac gttctgtcca aggtctgggc ttggggccgg
11281 gtcttcagac acccagaccc tcctgggacc ctcatgccac ttccacccag gggagcccc
11341 cacgatggtc atagaggggt ggatgtccct gctgaggggg gagccctggg tccccatgat
11401 ggtcatagag ggatggctct ccctgctgag cggcatgggg ccaaggagcc cccagccct
11461 gagacaagct gctgggaggt gaccagaggt gccaaggacc acctccccac agagccacat
11521 cccccacatg ggcatcccca gcacacttct gggggcacc ccacatcatc gagccaggcc
11581 caatgcacgc gtgggtcctt ctcccagaa atgtgccgac agcagcttca ccgtgctggc
11641 tgagctgcgg aagtgcggcc tgacggacaa cgagaactgc ctgaaagcgg tgacgctcag
11701 cctggacggc ggggacacgg tgaggacctg gctggggccc tgggctggga caggaagagg
11761 catgcgaagg tgtgtgggga gcaagcacgg tcaggtcccc ctccagcccc gaggccaggt
11821 cccccctcca gccccaggc caggtccccc tcagccccc aggtcaggtc ccccctccag
11881 ccctgaggtc aggtcctccc ggggggcaa ttgcagagcc caccgcaggt ccaggcctga
11941 gcttctctgt gggctctgtc cccagtgggg ccctgggc aggccacccc ctcatttgag
12001 agtcgggaat gggttcctcc ccagagctga cctccgccc gcctccttcc gcaggccatc
12061 cgggtccaag cggacggcgg cgtgttcctc aactccatct acacgcagct gccctgtcg
12121 gcaggtatgt ggctctccca ggacggccgg gctgggtggc gcctgcttgc agggcagct
12181 cccacagcct gggcagcgtc cgctccatcc ctgctagttc tccgtggcct cggcagctc
12241 caggagctcc ctgtgctcgg tttctcgtct gcagagtggg gatgccaggc tcccacccg
```

FIG. 6D

```
12301  gcagcggcag  ggaccccaca  tccagctcgc  tcagccccac  tctctcaggg  agcccggtct
12361  ccacctgagc  ccacttggcg  gccacaggca  tgggacaggg  agcctgaggg  ctcctggcca
12421  ctcctgggtc  tcactccgg   gtctcagtgg  ggtggccgg   cccactggat  gccctgcccc
12481  tccaatctag  ccagatctgt  ccctgcaccc  ctgaccggcc  tctccccac   actccggca
12541  gccaacatca  ccctgttcac  accctcgagc  ttcttcatcg  tggtgcagac  aggcctcggg
12601  ctgcagctgc  tggtgcagct  ggtgccactc  atgcaggtgt  ttgtcaggct  ggaccccgcc
12661  caccagggcc  agatgtgcgg  tgaggctggg  caggggcctt  cggggacagg  gccattgggg
12721  acggggcctg  gactagcgcc  aggctgcagg  gaggggcagg  cagaggcggg  cagggaccg
12781  gggaggggc   tgccccagg   gcatggcgga  gatcctggtg  ccagcgcagg  acaccagcat
12841  tggaccagcg  gccccggaag  cagccagctg  ggaggatgga  gcgggcagcc  ctgccctggc
12901  tcaggccgac  tttgcacagg  ggctggcttt  gcacaggggc  cgactgcaca  ggggcgcccc
12961  ccgccagggc  ttatctgcag  agggttctgg  gagcagaatc  ctgggacagg  gctcccagcc
13021  gttctaccct  gtgtggtgcc  tggagggatg  gcaggggcca  ggagccaggt  gggcccaaca
13081  gtggccgctg  acatccccca  accctggccc  ccaggcctgt  gtgggaactt  caaccagaac
13141  caggctgacg  acttcacggc  cctcagcggg  gtggtggagg  ccacgggcgc  agccttcgcc
13201  aacacctgga  aggcccaggc  tgcctgtgcc  aatgccagga  acagctttga  ggaccctgc
13261  tccctcagtg  tggagaatgg  tactcctcgc  ccccacccc   acagtcaccc  caggctcaag
13321  tcccacccag  caccttcctg  tccctgggc   cacggggacc  cctgggtggg  attggggacc
13381  ccatggaggc  aggtgggagg  catcaggagg  aggtgcttgg  ggccaggcgg  ccagaacccc
13441  ccaaggcgca  gcaggtgagc  cgcaaattcc  aactcactgt  tccccgggct  gaggggggtcg
13501  caggcctgcg  tgtcagggt   gtgggcttcg  gggcagggcg  tggagatgag  gtcaggtctt
13561  cccacagag   aactacgccc  ggcactggtg  ctcgcgcctg  accgatccca  acagtgcctt
13621  ctcgcgctgc  cactccatca  tcaaccccaa  gcccttccac  tcggtgagag  gctgaggcca
13681  gaccccacg   cctgggcagg  atgggtgggg  gagccctggc  aggctgggt   cctgacgcc
13741  ccgacgcctc  ccacctccgc  agaactgcat  gtttgacacc  tgcaactgtg  agcggagcga
13801  ggactgcctg  tgcgccgcgc  tgtcctccta  cgtgcacgcc  tgtgccgcca  agggcgtaca
13861  gctcagcgac  tggagggacg  gcgtctgcag  tgagtgccca  cgctgggggt  gggatgtgtc
13921  cacccgcgt   ggggtgcgg   gggaccctgg  ccggcagcag  ccgtcactca  cacggttctc
13981  agcccagagc  tttgcacttc  ctcatcccag  cctcgcaaga  acctcatgcc  cttcgatcc
14041  ccacgtcaca  gacggggatg  ctgagttgaa  gatggggct   ggccaggctg  ctcggccgct
14101  gacctgtccc  cctggccc    accaccaca   gccaagtaca  tgcagaactg  ccccaagtcc
14161  cagcgctacg  cctacgtggt  ggatgcctgc  cagcccactt  gccgcggcct  gagtgaggcc
14221  gacgtcacct  gcagcgtttc  cttcgtgcct  gtggacggct  gcacctgccc  cgcgggcacc
14281  ttcctcaatg  acgcgggcgc  ctgtgtgccc  gccaggagt   gccctgcta   cgctcacggc
14341  accgtgctgg  ctcctggaga  ggtggtgcac  gacgagggcg  ccgtgtggta  agggtctggg
14401  gggaaagcag  gccccccagg  tgctcctcag  agccacttcc  cgccctcccc  gaaggcttct
14461  gtgcctcccc  ccgagggttc  tgagacacga  ggggccaggc  tggggagagt  ggggcagggt
14521  ggacccagca  cattctgaag  agaaaattcc  cagctgggaa  agaggccagg  agaggaggtg
14581  gccctgggag  gacacctgct  ggctgttctc  agctgggtcc  acatggcagc  cctgccagg
14641  aaaggtgggt  ggcccccact  cccaccctgg  gctcaaaggc  cgctcctaac  cccagggtcc
14701  tggctgcttt  gctgccccc   tgtgtgtatt  tacccatgtg  cctccagggg  atttggggc
14761  tcccagcaaa  cacagcagca  ggcaccgtct  ggccttacaa  ggaggtggcc  aggctgggga
14821  ggcccagcat  tcggcggggg  ctcggaagcc  cggggtggg   gtctgcgggg  tgagggccgc
14881  agatccaggc  tgtgccgtct  gtctcttgta  gttcatgtac  gggtgggaag  ctaagctgcc
14941  tgggagcctc  tctgcagaaa  agcacaggta  agtgccaccc  ctgcctgcc   ctgccccgcc
15001  ccgcatcacc  ccgcctggcc  tggccccaac  acgcccacc   ctgcccacc   ccacctgaac
15061  cctgccgggc  caggtcagtc  ctcacctggg  ctctgccaca  ggcacccatg  ccctgacacg
15121  ccaggacgg   aggggccagt  gggtctctgc  cccgcagtgt  ggccggggtg  tcctgggtt
15181  gggggctgca  ggtgtcatgg  aagctttggc  tcggggctg   ttaacttgat  cagcaggaca
15241  ggctcagggc  tgcctggggt  cagttgaggg  ccgtggctgc  ccttccccag  gacccctccc
15301  accaagctct  gtccccaggg  tgtgcagccc  ccatggtgta  cctggactgc  agcaacagct
```

FIG. 6E

```
15361  cggcgggcac ccctggggcc gagtgcctcc ggagctgcca cacgctggac gtgggctgtg
15421  tgagttccat gcttcaggga ggggtgggca gggaaggggt cccagctttc ccagctcccg
15481  agcccaggga tctggtggtc ctggagacac ttacccacct ggaagctccg ccctggccca
15541  tgcgttgccc tgggtgctgc tgggtgcgcc tgtcccagag ggtgagtgac atctgcccac
15601  cctggtgtcc agccctgacc ggtacctgcc tgggccccac agttcagcac acactgcgtg
15661  tccggctgtg tctgtccccc ggggctggtg tcggatggga gtggggctg cattgccgag
15721  gaggactgcc cctgtgtgca caacgaggcc acctacaagc ctggagagac catcagggtc
15781  gactgcaaca cctggtgggt cgtgagtctc tcggaggcag caggtgggga gggcggggc
15841  ggggagggca gcgggtgggg aggcagcggg cagggagggc aggggcggg gagggcaggg
15901  ggccagctgg ccaggtgag gtggggccgt ggcaggagag agagttgcta ggaaagccat
15961  gggccgtcct gtgcgtcctc tggaaggtgg cccaggggcc atggtgctac caggagcctg
16021  gtggggctgc gtgccctgca ttcacagtgg gggacaccac ttcttccacg gaggagggt
16081  caggctgggc ctggggaggc tgaggcccg tgctgacctg cacaggcctg ggtgcgggt
16141  ctcaggaagg ccgggagagc aggccctgt gagcaggcac cattgtggcc ccttgcagca
16201  cctgcaggaa ccggaggtgg gagtgcagcc accggctctg cctgggcacc tgcgtggcct
16261  acggggatgg ccacttcatc acctttgatg gcgatcgcta cagctttgaa ggcagctgcg
16321  agtacatctt ggcccaggta cgccgccccc tcgcccactc ctgcaggccg ggcacactcc
16381  agcccgcggc cagcagcttg tctctttctg gcccaggact actgtgggga caacaccacc
16441  cacgggacct tccgcatcgt caccgagaac atccctgtg ggaccaccgg caccacctgc
16501  tccaaggcca tcaagctctt cgtggaggtg agaacggccc cagctgtgag caccccgac
16561  cctgcagcca acgagccggc cccagggaa gcttcgtgag ctttagctg cacccacagg
16621  ttctcagcag tgtcctggcc ccgggctgct gttccaagca gccacaaacc aggggctta
16681  gacaacagaa atgcattctc agtcctggag ccggaagtca gagatccagg cgggcagggc
16741  cacactccct gtcgagggtc tggggaggtc cttcctgcct ctcccagctt cacaggcggc
16801  aggcgtccct gggctgtggc tgcctgtggc ctcccgctgt gtctgcgtct gtcttctctc
16861  tgttttctc ttctgtctct tgtaaggaca ctggtcattg gatttagggc cccccccgc
16921  ccccacgtag tccaggatga tctcatttca agatgcttca cttaatcccg tctgcagaga
16981  tgctttctcc cagtgagggc ccgggctgag gttctgggag ttcgcatgtg gacaggcatt
17041  ttcaggagcc acgattcacc ctgccacacc tagagacacc cactccagca aaggggggcc
17101  agagctccca ggggataaag cagcgccgct ggccgggatg ctccctgcag atggcgggag
17161  gggctgagga ccgcagcggg tcaggggagg ctggtgtgag ggcgtggggg ctgcagggct
17221  ggatggggag cagggtgggg tggagtgggc ctactgcagc ctctgctgct cccgtgcagc
17281  cccaaggttc ccaggcagcc cctgttccca gcacttcctg gccagcctct tgccaaacct
17341  tcactgaggg tctcacggac ccagctcacc cctaacgcca gccgcttgtg ctaagagccc
17401  gtgcgcacct gcagagcact gggtggggca tccctgggtc tcaggcccct ccctgggggc
17461  cacagggtcg gcttccggca gcgtctgcct ccctgcaga gctacgagct gatcctccaa
17521  gagggacct taaggcggt ggcgagaggg ccgggtgggg acccacccta caagatacgc
17581  tacatgggga tcttcctggt catcgagacc cacgggatgg ccgtgtcctg ggaccggaag
17641  accagcgtgt tcatccgact gcaccaggac tacaaggtga gctcgggccg tgcactccta
17701  ggccctgcag gaccctctca cagtgacaga aaccctggtg ccaggtgggg cctgtgggac
17761  tcgctgaccc gtgggtgcgt gagcctggct ggtgagggcc ctgcctgtgg cctccacagt
17821  gggcagagga ttttgcaggg aagcaggtgc cacccagcgg cccacccagg gaccactgc
17881  acacctgtct cctacaagtt caccaggcac tgcctgggga accggctgcc ctccctccat
17941  ccccccgaggg ctctggagcc cagggtgggc tctgtgctgc ctcccacggg tgcctgtggc
18001  cccagctcca gggcccccact ctctcgctgc ctctgcaggg cagggtctgc ggcctgtgcg
18061  ggaacttcga cgacaatgcc atcaatgact ttgccacgcg tagccggtcc gtggtgggg
18121  acgcactgga gtttgggaac agctggaagc tctcccctc ctgcccggac gcctggcac
18181  ccaaggaccc ctgcacggcc aacccttcc gcaagtcctg ggcccagaag cagtgcagca
18241  tcctccacgg cccacccttc gccgcctgcc gctcccaggt gggctctgg tcttggcagg
18301  cagggtctgg tggggatggc agttgcttcc ttcccgccga gaactgggtc ttctgggcag
18361  acagcagcgc tccaaggagg gtctgaccat gtcccacggc acacagtcct ggatgtcagg
```

FIG. 6F

```
18421  tcccaagtcc ggatctcccg tcagccccac acctgtgcct cttgcccctg gcacgaagcc
18481  atcttggctg tttcccggcc actcctttga ccacagcctc agtcacaccc agaggctcac
18541  agggagggc  agccctctat gtggccccta gccaccctcc tctatgatcc ccagacctgc
18601  ccagtcctca gcacaaactg gaatgccagc ctggctcccc gctcagccag ggaggaatca
18661  gagatctgcc ctaagcagag acttccgaaa agcagtttcc tgactgggcg cggtggctca
18721  tgtctgtaat cccagcactt tgggacgctg aggcaggtgg atcacctgag gtcaggagtt
18781  tgagaccagc ctggtcaaca tggcgaaacc ccgtctctac aaaaaataca aaaatagccg
18841  ggtgtggtgg tgtgtgcctg taatcccagc tactcgggag gctgaggcag gagaatcact
18901  tgaacctggg aagaggaggt tgcagtgagc caagatcgtg ccactgcact ccagcctaag
18961  caaaagagt  gagactctgt ctcaaaacaa aacaacaaaa aaccaaaaag cagtttcgtg
19021  tcatcttaag gaagacttga gtgcccactt aggcacacag catggtggct caggagctga
19081  gatgagggc  tggcgtaggg gcagcagtgg gcatactcgc tcgtgggagg ccctgaagca
19141  ctctcatgtc ggccgccgct tgccctcttg agaaggcagc tggtgacccc ttggaaggtc
19201  ctgtggcctg acaaagctga gcccaggttc agatggggcc tgggaggggt gtgggctgcc
19261  tggaggaagc aggcagcttc ccatggtcag gacgcattca cagctcagct ccccgcgtgg
19321  ctggtctgga aaggaagtga ccactccttc cttagtgcac attcactggg tgcctggaat
19381  agcctggcat gttctgggct cacccagtg  atcaggggac gaggctgacc ctcacagagc
19441  ttccagagga ggcagaaagg cggtgggtgc tgggtggtcg gatgctagga tgtggagggc
19501  cctggccggg ggttggttcc gctggaggga aggcccccag gtggaaagga ggccagtacg
19561  actgcagcgg agggaggtgg gggcgagggc agagggtaag caggggtgct atgctccaca
19621  tgggtttgaa acctgtgggc cacatgacca gatccacgtg atagaaagat ccaaagagca
19681  catgtgaagg caggcagatg ggcaggtgca taggtgggca ggtgcatagg tgggcagatg
19741  gacaggtggg cagatgggca ggtgggcagg gatataggtg gacgagggca caggtgggct
19801  ggagaagtgc tggggcagct cccatttggg gcacgctctg aggtattcca ggccccagga
19861  gctcagagag ctgccatggg gggtgttgaa atacagatgg ttccagcaac tggccctggg
19921  ccagccaccc cctggccggg ggggccattg tcccggctga gctgcacctt ggcctcaccc
19981  gcaggttgac tccaccaagt actacgaggc ctgcgtgaac gacgcgtgtg cctgcgactc
20041  gggtggcgac tgcgagtgtt tctgcacggc tgtggctgcc tacgcccagg cctgccacga
20101  cgcgggcctg tgtgtgtcct ggcggactcc ggacacctgc cgtgagtcgg gctctgtccg
20161  tggtgctgaa gggtggagct gctggggcag gggaggaggt gtggcagcct ccgaaggtgc
20221  attgacctgg gcctgagccg cacacagaca tccaacacgc atgtgcctcc atgtgagtgc
20281  acaagtttct atgcacagag gaagacctgt gcaaaaccac cagacaggtt gccccagcat
20341  gagacagctc ctaggggaca agagttccaa gggcagggct ggggagtgga ggggaaggtg
20401  aggcaccacc cggccgaggc cctgcatgtc tgggacaagc ccgggtctgg ctctggggac
20461  accggccccc acgcccgggg taggggctgc cctgcacaac agggtgagg  gctggtggcg
20521  cctccttagc ctctgccctc tgtgcccag  ccttgttctg tgacttctac aacccacatg
20581  ggggctgtga gtggcactac cagccctgcg ggcaccctg  cctaaaaacc tgccggaacc
20641  ccagtgggca ctgcctggtg gacctgcctg gcctggaagg tgaggggcag cctttcttgg
20701  atggagcctc ctctccttgg gttcccgagt gtacgtgggg gggcggggat ccccagggac
20761  gcggtgtagg ctcccgtaaa ctgcacaatg caagccttga gggcaggccc ctgctggctg
20821  gtgggggcg  gctactccct gcagcatgga gccctggct  ggagagacta aagggccctg
20881  gtgagtcttc tgctcaccct gccggcccta ggctgctacc gaagtgccc  acccagccag
20941  cccttcttca atgaggacca gatgaagtgc gtggcccagt gtggctgcta cgacaaggac
21001  ggaaactact atgacgtcgg tgcaagggtc cccacagcgg agaactgcca gagctggtga
21061  ggggtggga  agcgggtggc gctggggag  cagggctggg gagcaggccc tgcaggctgc
21121  ccccaggcc  ctcagctcgc ctctccccca cccctagtaa ctgcacaccc agtggcatcc
21181  agtcgctca  cagccttgag ggtaaggaag gccggggg   ttagtgggcc ggtgaaggct
21241  ggggccaggg gctcggaggc cctgggtgac tctgccggct ccatcccag  cctgcacctg
21301  cacctatgag gacaggacct acagctacca ggacgtcatc tacaacacca ccgatgggct
21361  tggcgcctgc ttgatcgcca tctgcggaag caacggcacc atcatcagga aggctgtggc
21421  atgtcctgga actccagcca caacgccatt caccttcacc accgcctggg tcccccactc
```

FIG. 6G

```
21481 cacgacaagt aagccctgcc tggctctcct gaggcccagt actgtctggg tgacaaggag
21541 gaccccctgg gctcttagtg caggtgccct gtatggtagc gacagtccca atccactgac
21601 cttccgggct ctgtctaggg gtgcacggcc cctcaacacc ctgcgtgtct ccaggggctc
21661 cccacgaagc ctcagcacaa tgattgatgg gatacccaa ggagacaata aagctttcct
21721 ggactccgtc ccatccctca gcacggccta tcccagccag ccagctccct caaggccagg
21781 ctgccaggcc ccagtccctc atgcagaaac ggctctaacc aaggctgagg caggcactgg
21841 ggtccccagt atcccacagg ggcagggcca gccctgggga aagggtcctc tggggcccct
21901 ccaccttgtg aggccaggac tggaggatgc tgagccagga ccctttccc atgccccttg
21961 caggcccggc cctccggtc tccaccgtgt gtgtccgcga ggtctgccgc tggtccagct
22021 ggtacaatgg gcaccgccca gagcccggcc tgggaggcgg agactttgag acgtttgaaa
22081 acctgaggca gagagggtac caggtatgcc ctgtgctggc tgacatcgag tgccgggcgg
22141 cgcagcttcc cgacatgccg ctggaggagc tgggccagca ggtggactgt gaccgcatgc
22201 gggggctgat gtcgccaac agccaacaga gtccccgct ctgtcacgac tacgagctgc
22261 gggttctctg ctgcgaatac gtgccctgtg gccctcccc ggccccaggc accagccctc
22321 agccctccct cagtgccagc acggagcctg ctgtgcctac cccaacccag accacagcaa
22381 ccgaaaagac caccctatgg gtgaccccga gcatccggtc gacggcggcc ctcacctcgc
22441 agactgggtc cagctcaggc cccgtgacgg tcaccccctc ggccccaggt accaccacct
22501 gccagccccg gtgtcagtgg acagagtggt ttgatgagga ctacccaag tctgaacaac
22561 ttggagggga cgttgagtcc tacgataaga tcagggccgc tggagggcac ttatgccagc
22621 agcctaagga catagagtgc caggccgaga gcttccccaa ctggaccctg gcacaggtgg
22681 ggcagaaggt gcactgtgac gtccacttcg gcctggtgtg caggaactgg gagcaggagg
22741 gcgtcttcaa gatgtgctac aactacagga tcc
```

FIG. 6H

```
TGTGCCCTGAGTTAAAGAAACGTCACAAAGAACAAAGGAGAAGGCGGGTTCCAGCCTGCACCACAGCCCTGCGCTCTGAGGAGCACCTGGGGCTT  -1908
            AP-1                    GRE
CAGCCATGAGGGGTGACAGGTGGCAAAACGGGCCAGCTCGTTCACGTGCTGCTGTGCAGCTGTGTCTCGGCCCTCCATCTCCAGAACGTTCTCACATTCCA -1808
AGCTGAAACCCTGTCCCATGCAACACCAGCTCACCATCCCTGCCGCCACCGTCTGGCCCACACTCGTCTCTGCGGGTTTCATGACTCCA  -1708
GGGGCAGCAGCACGAGTGGCCCCTCGCCTTTGTCCACTGCCACTGCACAGTGTCCCCAGCTTCCCCATGGAGCAGCCTGGCCA  -1608
GCCCTCCTTTTCACGGCTGAACCGTATTCACCGACGGATCAGCCTCACGATGCTGACCCAGTCTCTTCCCAGGACACATGGGCAGCTTCTGCCCT  -1508
TGTCAGTGATGCTGTGTGGACATGGTGTGCAAATGTCCCTCAGGACCGCCTTCAGTTCTTCTGTGTTCTTGATCCCGCCATCTATTGAGCGTGAGACAGG  -1408
CCACCAGCAGGGCACAGGCTCCGGGTCCTCCGGGTTCCCACGTCTTGTCCCAACACTTCTACTTCTGTGTTCTTGATCCCGCCATCTATTGAGCGTGAGACAGG  -1308
TCAGAAGCTTTGAAGATGGGCTTTCGTCTTGTCCAGAAATCCCACCTCTAAGAATTAACTTCAGAAAGACAAACGCGGGAGCTGTGCAGGGCCG  -1208
TGACGGGGACTGTGACGTGAGTAAAACAACAGACCTGGACACCACCCTAGGGTCCCATGGGCCGGACGAGGCCACACACCGACCTGGTGCTTCCTGC  -1108
                         Hoxd9,Hoxd10
CTGGCGTCTGCGCCACGAGCATTCAGGACGCTGGTGACCAGGAGCCAGGAGGTGGGAGCATCTGAGGTGCAGGTCACGGGCAGGAGGTGTTTGCAA  -1008
                AP-2
GAGGTATTGCAGCGCGACGAGGTGCTCAGATGCTGCGCTGTGTCCTGGGAGGCCAGGAGGTTTACCACACATAGCCCCGGAAGCCA  -908
CCAACACCAGCCAGCTGTAGGCTTCTGCGAGCTCCACTGCAGGGAGGACCTCAGGGCCAGGTTCAGGAGCTCAGGAGCAGCTGCTTCCTCA  -808
ACCCTGCCAGGGTTAATGAGGAGGCCCCCAGAGTGAGGTGGAGGCCAAATGGGCCTCAGTTTCCCCTTGAATGTGAACTTGAAACAGATCAGCCAGAGACCTCCC  -708
CAAGCGCAGCTGACTCCGATGTGCATGGCCAGGAGACACTCTGGGGTCTCTGGAAATAGAGCCTCTCAGGGACCCCACACGCCTCCAGACTGAGCATCCTGCCAT  -608
ACGGTCTTCAAGGGCTCGGTGGTCAGTCAGTGTGCAGGAGCCTGCCGGGCTCCCGGGCTGGGCTAAGCAGTAGCAGTGTGGAGGGAGCTCGTGGGCCTGTGGGCTGAGGCAGGCTGGCACCTGGGGG  -508
                                                                        AP-1
GTGCATGCCTGAGCTCAGCAGGAGCCTGCCGGGCTGCTGCCCAGAGGCTGGATTCCCTTCAGCAGGAGCCGCAGTGGGCGAGTGGGCTGAGTGTGAGGCAGGCTGGCACCTGGGGG  -408
ACCCATGGTCAGTGCTGGGGGTGCTGCCAGGCCAGCCTGCCTTCTCCCTTCCGATTCT  -308
                                NF-κB
TTCCATGACCCTGCTGCAAGGCCAGCCTGCGTTTGCAGCGCTTTGCCATCTAGGACGCGGTGCCAGGTGGGTAGGCCCTTCTCTCCCTTCCGATTCT  -208
                                                                                        TATA box
CAGAAGCTGCTGGGGGTGGGGCGTCTGGGCCTCAGGGCACAGAGCTGCAAATCCTTCTGATCCAGCTGCAAAGGCTCTCCCCTGCACAGCCCTGCAGAG  -108
CAAACACACGTGGCTGGAGCGGGGAAGAGCACAGGTGCCTGCGTTGGGGCCAAGGCTCCCTGCTTGGGGCCAAGGCTCCCTGCTACATAAGCTGGGCCCCAGGG  -8
                                                                            c-Myc
GAGCAAGCACCCGGCCCTGCCCTCCCTGCCTGCCCCCGTGCCAGCCCGTGCCAGCCCGTCCCCCGTCCCCGTCCCCGTGCCAGCCCGTGCCAGCCCCAGG ATG GGT GCC CCG AGC GCG TGC CGG ACG +86
     +1 ┗━▶ (TRANSCRIPTION START)                              (M   G   A   P   S   A   C   R   T
CTG GTG TTG GCT CTG GCG GCC ATG CTG GTC GTG GTG CCG CAG GCA GAG ACCA       PUTATIVE SIGNAL PEPTIDE
 L   V   L   A   L   A   A   M   L   V   V   V   P   Q   A   E   T)

FIG. 8
```

```
(-1098) ggcgtctgcg ccacggagca ttcaggacgc tggtgaccag
ggagccagga ggtgggagca tctgaggtgc aggtcacacg ggcaggaggt
gtttgcaaga ggtattgcag cgcggacgga gtgtcctgca gatgacgctg
tctgtcctgt agatgacgct cgtcaaggag gtttaccaca tagcccccgg
gaagcccacc caacaccagc cggaggtgct aggcttctgc ggctcccacc
tggggcaggc ggaggacccc gggcaggtcc aggacccccc ggagcagctg
cttcctcaac cctgccaggg ttaatgagga ggcccagag  tgaggtggag
gccaaatggg actcagggcc ggagcctctg gcctggctgg atcagggctg
gcattggaca agcgcagctg actcccgatg tgcatggcca ggagacactc
tgggcctcag tttcccttg  aatgtgaacc ttgaaacaga tcagcccaga
gacctcccac ggtcttcaag gggctctggt cagctgggct ggggtctctg
gaaatagagc ctcctccagg gacccccaca agccacccag actgagcatc
ctggccatgt gcatgcctga gctcagcagg agcctgccgg gctcccgtg
ggctaagcag tggtgggagg ggagctccag cctcgtgggc cctgcccggg
cctcggggac ccatggtcag tggctggggg tgctgcccag aggctgggat
tcccttccag caggagccgc agtggggctg agtgtgaggc aggctggctg
accactgttt ccatggaccc tgcgtccaag gccagccctg ccttccagcg
gctttgccat ctaggacggg tgccaggtgg ggtaggccct tctctccctt
ccgattctca gaagctgctg ggggtggggg cgtcctgggc ctcagggcac
agagctgcaa atccttcctg atccaggcct ctccctgcc  acagccctc
cccgagagca aacacacgtg gctggagcgg ggaagagcac ggtgccctgc
gtggcctggc ctggcttggg gccaaggctc cctgctacat aagctggggc
ccccagggga gcaagcaccc gg  (+7)
```

FIG. 10

(-4169)    ggtaccctg  gttgtgcctg  tcgctcagtg  ggccagggtc
taagggctgt gaagactcaa catgcccca  cctgctactt  ctgaacacca
ggcactggct ctgagacccc cgggccttgc tggacatctc  cccaggtgta
ctgggccagg ggcagggc   ctggccatcc caacacccag  gagcaagcag
cccgtcacct gcccaggtcc ccgaggcccg gaacaccttc  ctgctgggcc
cacccagccc tggacctgtc ccgcttggtc acacgatggg  accctcggcc
catcagcagg tgagccccca ggagcgtgcg tctggcctgg  taaggcctcc
accccaggag ttgggggcc  cccgtgccag ggagcaggag  gctgccgagg
tggagggtcc cacacagcta ccactcccta tccccagcac  agcctgggc
ctggctctga gtacacatcc tggggcctgg ctctgagcag  accaagagcc
catccctgct ttgtgacccc ctgggctgtg cctgacaccc  caggtgtcca
gcgtggagct ggggcccagc tcagtgcctg ggagctgatg  gaccctgggg
cccggctcag tgcctggtgg ctgatggaca ctggggcctg  gctcaaacct
gcaccgctgt ggtcggggga ggggagggct gagccacgtg  ggaacccag
ccccagtgac gactctttgc ggtggccaag ccctccaggt  gtcccccagg
gctgagggc  tgggcttggg gcagctggtg acagcagatg  gtggccctga
tcactggtgc ctggacggcc tctgaagggg tctgtggggt  cctggacggg
tccccattca tggcaggatt aaccccctc  gggttctgtg  tggtccaggc
cgccccttg  tctccactgc ccctggcca  gaatgaggga  cagtgaccca
cccagggctg ggcctggctc agactccgtc agagccgcag  ggcaagttcc
tggcacgtcc gaggtgggag gctcctctgc gctccaggag  gctgtgcctg
gccccttc   ccggcaggaa ccggctgtgt ccctttcctt  cctttatctt
ctgttttcag cgccttcaac tgtgaagagg tgaactcttc  aaacacgctg
agcaaacagg cccgactccc agggccgcat ccgggatgtc  tcaatagctg
tggccttgac gtccacctcg gaccctgcc  ccggacccag  cccagttccc
aatgggccct ctgcccgggg aggtgcctag tgggagggac  gagggcaaag
tcggggcccc cacttgtttg gtgtcactgt gtgccagcgg  ccactggcgg
gcgaggctgt tccagggtgg aggcggggag ggttggacca  caggcactga
gcggggacag aggagctgcc tgagggtccc agctctgcca  tggagaaaac
gctatctcgc tgatgcagag gtgcccggcc cactcgagct  ggggggtgagg
gggctgctcc ccagtgggcc gccagccccc atgaaggccg  cgggcaccgg
ccgtggtcag ggagggcagg ggacaggcag tgggggccag  cagggagac
actaggcttg gccccagcac ccaggtgggc atcggcttgt  gagctggagc
cgcgggcagg gagggggat  gtcacgaggg cttggctaag  gtgggagacc
tgggcgggtg cgtcggggg  acgtctgcag cagaggcctg  ggcagcaggc
acacccctcc tgccagtgcg aggaacgagg cgccacagcg  gccggtagcc
ccccatttgc ccagcctggc ctggagcagg caggaaggcc  ggggagaggg
gtctggctgg ggcctgggtg cagtcacagc cacgagccca  ggggtgggga
ctctggccca cccttcagac catgctcaag gcccactggc  ccaggcatgc
ccgccacccc ttccaccgtg ccgtgctgca gcgggtctac  cggcctggat
gtgaaagaga gcttggagac cccagagacc tcggaacctt  cagctttgga
agtgacgtcg gtggggtggg tgggggagc  acaggctctg  gagtcccgga
agtgagcggg gagctacgct gagatctggg agacccctg   ccccaccca
ggtacagggc caggcagaag cccgaggtgt gccctgagtt  aaagaaaccg
```

FIG. 11A tcacaaagaa caaagggaga aggcgggttc cagcctgcac cacagccctc
gcgctctgag gagccacctg ggggcttcag ccatgagggg tgacaggtgg
caaaacgggc cagctccgtt cacgtcgctg tgcagctgtc tccggccctc
catctccaga acgttctcac attcccaagc tgaaaccctg tccccatgca
acaccagctc accatcccct ctgccagccc ctggcgccca ccgtccacac
tccgtctctg cgggtttcat gactccaggg gcagcacacg agtggccct
cctgcctttg tcctctgtgt ccacctgcct cactctgcac agtgtcccca
gcttccccca tggagcagcc tgggccagcc cctccttttc acggctgaac
cgtattccac cgcacggatc agcctcacga tgctgaccca gtcctccgcc
caggacaca tgggcagctt ctgcccttg tcagtgatgc tgctgtggac
atgggtgtgc aaatgtccct caggacccgc cttcagttct tctggggaca
gacccagagt ggagttgctg gtcaccccca ccagcagggc acaggctcc
gggtccccac gtctctgcca acacttccta cttcctgtgt ttcttgatcc
ccgccatcct attgagcgtg agacaggtca gaagctttga agatgggctt
tcgtcttgtc ccagaaatcc cacctctaag aatttaactt cagaaagaca
aacgcggggg agctggtgca gggcccgtga cggggactgt gacgtaaata
aaacaacaga cctggacacc accctagggt ccccatgggg ccggacgagg
ccacaccacc cgacctggtg cttcctgcct ggcgtctgcg ccacggagca
ttcaggacgc tggtgaccag ggagccagga ggtgggagca tctgaggtgc
aggtcacacg ggcaggaggt gtttgcaaga ggtattgcag cgcggacgga
gtgtcctgca gatgacgctg tctgtcctgt agatgacgct cgtcaaggag
gtttaccaca tagccccgg gaagcccacc caacaccagc cggaggtgct
aggcttctgc ggctccacc tggggcaggc ggaggacccc gggcaggtcc
aggacccccc ggagcagctg cttcctcaac cctgccaggg ttaatgagga
ggccccagag tgaggtggag gccaaatggg actcagggcc ggagcctctg
gcctggctgg atcagggctg gcattggaca agcgcagctg actcccgatg
tgcatggcca ggagacactc tgggcctcag tttccccttg aatgtgaacc
ttgaaacaga tcagcccaga gacctccac ggtcttcaag gggctctggt
cagctgggct ggggtctctg gaaatagagc ctcctccagg gaccccaca
agccacccag actgagcatc ctggccatgt gcatgcctga gctcagcagg
agcctgccgg gctccccgtg ggctaagcag tggtgggagg ggagctccag
cctcgtgggc cctgcccggg cctcggggac ccatggtcag tggctggggg
tgctgcccag aggctgggat tcccttccag caggagccgc agtggggctg
agtgtgaggc aggctggctg accactgttt ccatggaccc tgcgtccaag
gccagccctg ccttccagcg gctttgccat ctaggacggg tgccaggtgg
ggtaggccct tctctccctt ccgattctca gaagctgctg ggggtggggg
cgtcctgggc ctcagggcac agagctgcaa atccttcctg atccaggcct
ctccctgcc acagccctc cccgagagca aacacgtg gctggagcgg
ggaagagcac ggtgccctgc gtggcctggc ctggcttggg gccaaggctc
cctgctacat aagctggggc ccccagggga gcaagcaccc gg (+7)

FIG. 11B

```
   (-13)        ccagggga  gcaagcaccc  ggcccggctc  cctccctgcc
cgtccccgtc  cccccacccg  tgccagcccc  caggatgggt  gccccgagcg
cgtgccggac  gctggtgttg  gctctggcgg  ccatgctcgt  ggtgccgcag
gcaggtaaga  gccccccact  ccgcccctc   tcgatgctgt  cttcacggcg
ggggtctctg  caggtcgctt  gcctgggagc  ttctcctgca  gagtgcacgg
gcagatcccc  ctacgactcc  ctgagtgtcc  tggatgggac  cctacccgtc
cccaacacag  ggctctgggg  ccccacgggc  tcacagtgtc  aggaaactca
ggggctggct  tggatggggt  gtccaggaga  aggtgggccc  ctgaccgcag
ggcaaggccc  ctgggagacc  accgaaaggg  tcttggtctt  gggggtggga
caggagtggg  caatggggga  ggggtcaca   gctggggtc   tctctggagc
cccatgaggc  ccaggcatca  gagtgagcag  gggcaggctt  agcgtggacc
cctgtccagg  accggctcta  cccttcacga  cctcctggg   gatcacagct
ggcagggcag  gtgagggtac  ccgggaccct  caagggttgc  acagccagcc
gcaagagccc  cggcctcaac  ccacgctcga  ctccacggc   ccatctgtgg
gcatctcatg  ccgcacgggc  tgcctggctc  tcagccgagc  gttttccctc
gtctgctgtc  tcttggccag  agccgcagca  ttaatactta  ctgtcaatag
agaaagatgc  agccccaggg  gccacggga   gacacccagc  caggctggcc
atgaggctgc  tgcagcccct  ccctgccccg  cctccgccc   ctcccaagc
ttggggtctg  ggctgggcag  gtgaggttcc  ctggggtctc  tctccatctg
tggaagggag  gctgggtggt  cagcagggct  ggaggcaggg  ggcttccccc
agtggctccc  agcctgggcc  cggggggagc  tgcgtctggc  tgcaaggttt
gggggctggt  ttgaccagaa  tagccacctc  cttgcatctg  attcttccgg
gccatgcagc  cttggctccc  ctcacctgag  caggcagggc  ctagggactc
tcagcccacc  cgtcctcctg  tcctccacgc  acgtccaagt  tggggagatc
aagcccttgg  cagggactgt  gctttagtca  ccagatgcac  gtcctgtggc
cggggaaggc  agccctgcac  agagcagctt  catgttaggg  gacacacccc
aaagtgatgg  ggtggctggt  ggtgggcact  tctctggcta  caagatggag
gcccaggtgg  tccagcccaa  ggagggcact  gcacggagca  gataaccaag
ggcagtcagc  ctgggcaggg  gaggggctgc  ctgggggga   ggggttgcct
gggttgggga  ggggctgtct  ggggcagggg  aggagctgcc  tggggcgggg
gagggctgt   agggccaggg  aggggctgcc  tggggctggg  gagggctgc
tggggtgggg  aggggctgcc  tgcggcggga  gccggggcgt  gggagtggct
ggttgggctg  gcacacaggg  gcaggctgt   gagctgtggg  tcgggtgga
ggactcaggg  atcggctggc  tttctgggaa  aggcagtcaa  cctggatctc
tggaggcggc  ccctgtggtg  gttcccagat  gtcagcagga  cctggctgga
aaagccaggc  agggccaggc  cagagtgcga  accacagggc  cggcccctcg
ctgagccctg  accatgcttg  tggggctgg   ggctcacct   cccacctccc
cacagagagt  ctcagatcag  gatccaggga  ggagctctgg  ggtcctgtga
aggggcgcc   caacccaaa   ctgggcagac  aatggccggg  ggtcctcaga
gtcctgtggg  ttggagctgc  ctcctccag   cctccatggg  gttggtgggt
gaggccttgc  ccggaggcgg  tggtcagcct  gggggacctt  gggcggccat
cccagtatca  acggccacac  agcttgcgcg  gcccagagtc  ctgcccccag
cctgccccac  tcgccctgac  ttaggatcta  gttcgaaact  ggttctgtgt
ttaggtttct  gctaagtcac  gcctggaagg  ctccaagtgt  gtcctcctaa
```

FIG. 12A

```
caaagctggt ctttgtcctt ctccaaggga tgtgtgggat ggggcgaaat
ccccccttgg ggcggccaac gcctttcct gattccattt tctcccccat
cccttgagaa ggaggcacca tccccgcctg tcagtcgggg acagggcagg
ccgtgctggg ggcagctcag ggctccctgc tggaagcttc catcccgcag
gctttccata gcattgagca ggagcggagg catctgcggc tgacggttgg
ggtggcctga gcggctgggg aggagtcccg gccttggcca cagtgtgtcg
tgagggtgaa cctgcagggc atggagaccg ccaccaagga ccccacatgc
ggctgccgca ccagggatgt ggccaggtcc gtggttgggt tcgtggctgg
cagccacatc tagttcctca ctgactccca ttccctcttc ccacagagac
ccagggccct gtggagccga gctgggggaa tgcagggcac accatggatg
gcggtatgtg gccaggttcg ggggtggggg gttcctgacc aggctggagg
ggctgga (+2738)
```

FIG. 12B

COMPOSITIONS AND METHODS FOR THE ANALYSIS OF MUCIN GENE EXPRESSION AND IDENTIFICATION OF DRUGS HAVING THE ABILITY TO INHIBIT MUCIN GENE EXPRESSION

This invention was made with Government support by Grant Nos. HL35635, ES06230 and ES09701, awarded by the National Institutes of Health. The Government has certain rights in this invention.

BACKGROUND OF THE INVENTION

1. Field of the Invention

The invention relates to compositions and methods for the assessment of mucin gene expression. The invention also relates to compositions and methods for the identification of compounds useful in the treatment of various medical conditions caused by mucin overproduction.

2. Description of the Related Art

Mucins are a family of high molecular weight glycoproteins secreted from epithelial cells at many body surfaces, including the eyes, pancreatic ducts, gallbladder, prostate and respiratory, gastrointestinal and reproductive tracts. Mucins are a major component of mucus, and are responsible for the viscoelastic properties of mucus, and serve a role in protecting and lubricating the epithelial surfaces. At least twelve mucin genes have been identified in humans.

In the airways, mucin proteins form a protective barrier on the airway epithelial cells, and interact with cilia to trap and clear pathogens (e.g., microorganisms), particulate matter, irritants and pollutants (e.g., tobacco smoke and sulfur dioxide). Mucus secretions in the airway are produced from two different secretory cell populations, the surface epithelial goblet cells and the mucous cells in the submucosal glands. At least eight mucin genes are expressed (at the mRNA level) in the upper and lower respiratory tracts. Of these, only the MUC5AC and MUC5B polypeptides have been conclusively demonstrated to be major components of human airway secretions (Hovenberg et al., Biochem. J., 318(Pt. 1, Vol. 17):319–324 [1996]; Hovenberg at al., Glycoconjugate Jour., 13(5):839–847 [1996]; Thornton et at., J. Biol. Chem., 272(14):9561–9566 [1997]; and Wickstrom et al., Biochem. Jour., 334(Pt. 3, Vol. 14):685–693 [1998]). MUC5B is also expressed in other tissues, including, for example, pancreas and gall bladder.

Diseases of Mucin Overproduction

Mucin production is upregulated in response to mucosal irritation. Most notably, bacterial infection of the airway epithelium is often accompanied by mucin overproduction. Some airway diseases are also characterized by mucus hypersecretion. Hypersecretion of mucus can overwhelm the ability of the cilia to function properly, and can result in various pathologies, such as airway mucus plugging and airflow obstruction. Mucus hypersecretion also contributes to chronic infection by shielding bacteria from endogenous and exogenous antibacterial agents. Mucus plugging and bacterial infections create a non-healing injury and can result in chronic influx of inflammatory cells which destroy gas exchange tissue. When severe, these effects result in respiratory function decline, and can be fatal.

Diseases which are characterized by mucin (and mucus) hypersecretion also frequently demonstrate goblet cell hyperplasia and submucosal gland hypertrophy. Such diseases include, for example, chronic bronchitis, bronchial pneumonia, cystic fibrosis, chronic asthma, emphysema, usual interstitial pneumonitis and other diseases (Basbaum et al., Am. Rev. Respir. Dis., 144(3 Pt 2):S38–41 [1991]; Yanagihara et al., Am. J. Respir. Cell. Mol. Biol., 24(1):66–73 [2001]; Rogers et al., Eur. Respir. J., 7(9):1690–706 [1994]; and Kaliner et al., American Review of Respiratory Disease 134(3):612–21[1986]).

MUC5B mRNA and Genomic Structure

In order to better understand the molecular mechanism of mucin gene expression regulation in normal and disease states, it is necessary to elucidate the genomic structure of the mucin gene. MUC5B and three other mucin genes, MUC6, MUC2, and MUC5AC, have all been mapped to 11p15.5 on a single band of 400 kilobases, and their order has been determined to be: telomere-MUC6-MUC2-MUC5AC-MUC5B-centromere. The MUC5B genomic structure (i.e., exon identification, intron/exon boundaries and transcriptional start sites) and cDNA sequence are also partially known, albeit with some discrepancies in the published literature (Pigny et al., Genomics 38(3):340–352 [1996]; Desseyn et al., Jour. Biol. Chem., 273(46):30157–30164 [1998]; Desseyn et al., Jour. Biol. Chem., 272(27):16873–16883 [1997]; Desseyn et al., Jour. Biol. Chem., 272(6):3168–3178 [1997]; Offner et al., Biochem. Biophy. Res. Comm., 251(1):350–355 [1998]; and Keates et al., Biochem. J., 324(Pt 1):295–303 [1997]).

The MUC5B gene is large and complex. The MUC5B exons and introns encompass approximately 39076 basepairs of genomic sequence, and the gene's cDNA is approximately 17079 basepairs in length. The gene is characterized by an unusually large central exon of 10,713 basepairs and 3,571 amino acids. The central exon contains multiple repeated motifs, including characteristic cysteine-rich subdomains, which are also found in other mucin genes. In addition to the large central exon, there are approximately 30 smaller exons upstream and another approximately 17 exons downstream of the central exon. In total, the MUC5B message is predicted to encode a 5683 amino acid polypeptide having a molecular weight of 590 kDa. However, as the mucin proteins are extensively glycosylated, the observed molecular weight is expected to be much greater. Conflicting descriptions of the gene's transcription start sites and identity of the first exon have been reported.

There exist published reports of the isolation and analysis of limited portions of the MUC5B 5' promoter region. Van Seuningen et al. (Biochem. J., 348(Pt. 3):675–686 [2000]) describe an analysis of the MUC5B promoter region, which encompasses approximately 956 basepairs of genomic nucleotide sequence upstream of the transcription start site. Perrais et al. (J. Biol. Chem., 276(18):15386–15396 [2001]) describe an analysis of the MUC5B promoter region, which includes approximately 2044 basepairs of genomic nucleotide sequence upstream of the transcription start site. GenBank Accession Number AJ012453 describes approximately 2954 basepairs of MUC5B genomic sequence 5' of the transcriptional start site.

There is a need to identify compounds capable of inhibiting the production of mucin proteins, and specifically, MUC5B protein. There is a need to provide therapies for reducing mucus (e.g., MUC5B) production in individuals suffering from airway diseases characterized by mucus hypersecretion, such as cystic fibrosis, chronic bronchitis, bronchial pneumonia and asthma. The object of the present invention is to provide novel compositions and methods that find use in the analysis of MUC5B gene expression. These compositions incorporate previously unreported MUC5B genomic sequences derived from the MUC5B gene 5' promoter region, and the methods of the invention use these sequences. These novel compositions further comprise reporter genes in operable combination with the novel MUC5B gene 5' promoter regions of the present invention. It is also an object of the present invention to provide methods for drug screening using the novel MUC5B promoter reporter constructs to identify compounds having the ability to downregulate MUC5B gene expression. The invention also provides transgenic animals suitable for use in screening assays to identify compounds capable of inhibiting mucin production. Compounds thus identified find use in the treatment of diseases characterized by mucin hypersecretion.

SUMMARY OF THE INVENTION

The present invention provides novel isolated nucleic acid molecules comprising promoter sequences regulating the transcription of the human MUC5B gene. These novel sequences are provided in SEQ ID NO: 31 and SEQ ID NO: 32. In a related embodiment, the invention also provides nucleic acid molecules wherein the promoter sequences of SEQ ID NO: 31 or SEQ ID NO: 32 are operably linked to a heterologous gene (i.e., a gene that is not naturally linked to the promoter sequences of SEQ ID NO: 31 or SEQ ID NO: 32).

In one embodiment, the combination of promoter sequence and heterologous gene reside within a vector. In some embodiments, the heterologous gene contained on the vector is a reporter gene. The heterologous gene can encode various polypeptides, including luciferase, green fluorescent protein (GFP), chloramphenicol acetyl transferase (CAT), β-glucuronidase (GUS), secreted alkaline phosphatase (SEAP) and β-galactosidase (β-gal).

It is intended that host cells harboring the nucleic acid molecules and various vectors of the present invention are also within the scope of the invention. The nature of the host cell is not particularly limited. In some embodiments, host cells harboring the nucleic acid molecule comprising either promoter sequences of SEQ ID NO: 31 or SEQ ID NO: 32 operably linked to a heterologous gene are provided by the present invention. Furthermore, host cells harboring a vector carrying either of these promoter sequences operably linked to a heterologous gene are also provided by the invention. In related embodiments, host cells harboring a vector carrying either of these promoter sequences operably linked to a reporter gene are provided by the invention. In some embodiments, the host cell is a eukaryotic cell. In other embodiments, the host cell is a cell of human origin. In some preferred embodiments, the host cell is a cell of tracheobronchial epithelial (TBE) origin. When cells are of TBE origin, they may be primary TBE cells or established HBE1 cells. In one embodiment, when the host cells are eukaryotic cells, the host cell can be present in a non-human mammal, in which case the non-human mammal is a transgenic animal. It is intended that transgenic animals comprising the nucleic acid molecules, vectors and host cells of the invention are within the scope of the invention.

The present invention provides a variety of cell culture conditions and culture methods for the cultivation of the host cells of the invention. In its broadest sense, the invention provides a method for culturing a host cell in a culture medium under conditions allowing the expression of a heterologous gene product that is under the transcriptional control of MUC5B promoter sequences SEQ ID NO: 31 or SEQ ID NO: 32. In one embodiment of these cell culture methods, the host cell is of tracheobronchial epithelial (TBE) origin. In other embodiments, the host cell of TBE origin is cultured biphasically in an air-liquid interface. In still other methods for culturing host cells of the invention, the host cell of TBE origin is cultured on a substrate comprising collagen gel. In still other culture methods, the host cells are cultured in the presence of retinoic acid.

In another embodiment, the present invention provides non-human transgenic mammals comprising eukaryotic host cells harboring the promoter sequences of SEQ ID NO: 31 or SEQ ID NO: 32 operably linked to a heterologous gene.

The present invention provides a wide variety of methods for the assessment of MUC5B promoter activity, and related screening methods to identify compounds having the ability to inhibit human MUC5B promoter activity. In one embodiment, a method for the assessment of MUC5B gene promoter activity entails delivering a reporter construct driven by MUC5B promoter sequences SEQ ID NO: 31 or SEQ ID NO: 32 operably linked to a reporter gene to a host cell, and assessing the expression of said marker gene product encoded by the reporter gene. In this method, expression of the marker gene product is indicative of MUC5B gene promoter activity.

In a related embodiment, the method above further comprises measuring the quantity of the marker gene product, where the quantity of the marker gene product is proportionate to MUC5B gene promoter activity.

In another embodiment, the present invention provides a method for identifying a compound capable of modulating MUC5B gene promoter activity, where the method has the steps of providing a first and a second sample of a host cell, where the host cell harbors a reporter construct driven by a MUC5B nucleotide sequence of SEQ ID NO: 31 or SEQ ID NO: 32, operably linked to a reporter gene encoding a marker gene product; contacting the first sample of host cells with a test compound; assessing the expression of the marker gene product in the first and second samples; and identifying the compound as capable of modulating MUC5B gene promoter activity if the expression of the marker gene product is significantly different in the first and second samples.

In a related embodiment of the method above, the quantity of the marker gene product is measured, where the quantity is proportionate to MUC5B gene promoter activity. Also in a related embodiment of the method above, the modulation is inhibition.

The present invention also provides a method for identifying a compound capable of modulating MUC5B gene promoter activity. In one embodiment, this method comprises the steps of providing a host cell harboring a reporter construct driven by a MUC5B nucleotide sequence of SEQ ID NO: 31 or SEQ ID NO: 32, operably linked to a reporter gene encoding a marker gene product; contacting the host cell with a test compound; measuring the activity of the reporter gene construct; and identifying a compound as capable of modulating MUC5B gene promoter activity, if the activity of the reporter gene construct is significantly different from activity measured prior to contact with the test compound. In one embodiment of this method, the modulation is inhibition.

The present invention provides methods for producing a non-human transgenic animal. In one embodiment, the method comprises the steps of introducing a vector comprising a reporter gene under control of a MUC5B promoter sequence comprising a nucleotide sequence of SEQ ID NO: 31 or SEQ ID NO: 32 into an embryonic stem cell of a non-human transgenic animal to produce a transgenic embryonic stem cell; introducing the transgenic embryonic stem cell into a female mouse under conditions such that the mouse delivers progeny of the transgenic embryonic stem cell; and identifying at least one offspring of the progeny comprising the vector.

In another embodiment of this method, the non-human transgenic animal selectively expresses the reporter gene in a cell of tracheobronchial epithelial (TBE) origin. In another embodiment, the transgenic animal is a mouse.

The present invention provides methods for screening compounds for the ability to modulate MUC5B gene promoter activity. This method comprises the steps of administering a test compound to a non-human transgenic animal produced by the method above, and monitoring MUC5B gene promoter activity. In one embodiment of this method, the modulation is inhibition.

The present invention also provides a method for the specific expression of a nucleic acid of interest in cells of tracheobronchial epithelial (TBE) origin of a mammal, comprising delivering a vector comprising the nucleic acid of interest under control of a MUC5B promoter sequence with a sequence of SEQ ID NO: 31 or SEQ ID NO: 32 to the mammal.

BRIEF DESCRIPTION OF THE DRAWINGS

FIG. 1A shows a section of bronchial tissue after the in situ hybridization. Original magnification is 100×. FIG. 1B shows an enlarged picture of the surface epithelium in a region different from FIG. 1A. Original magnification is 400×. FIG. 1C shows an enlarged picture of the submucosal gland region from FIG. 1A corresponding to the rectangle in that image. Original magnification is 400×.

FIG. 2A shows a normal trachea tissue section following staining. FIG. 2B shows trachea tissue section of a typical interstitial pneumonitis (UIP) patient following staining. FIG. 2C shows a section of bronchiole region tissue from a UIP patient following staining.

FIG. 3A shows a section of the trachea tissue of a UIP patient after the in situ hybridization. A 48-mer oligonucleotide (SEQ ID NO: 1) corresponding to the antisense sequence of the human MUC5B tandem repeats region was used as the in situ probe. Original magnification was 100×. FIG. 3B shows a cross section of surface epithelium of the bronchiole region of the UIP patient's lung. A MUC5B oligonucleotide as described in FIG. 3A was used as the in situ probe. Original magnification was 400×. FIG. 3C shows an in situ hybridization in a human tracheal tissue section derived from a patient with emphysema. A MUC5B oligonucleotide as described in FIG. 3A was used as the in situ probe. Original magnification was 100×. FIG. 3D shows an in situ hybridization in a human tracheal tissue section derived from a patient with emphysema using a MUC5AC nucleic acid probe (SEQ ID NO: 2). Original magnification was 100×.

FIG. 4A, top panel, shows Northern blot analysis of total RNA isolated from primary explant human tracheobronchial epithelial (TBE) cell cultures. These cultures were maintained under four different culture conditions, which were standard tissue culture dishes (TC), collagen gel coated dishes (CC), Transwell™ chambers (BI), or collagen-gel coated Transwell™ chambers (BICG). Cultures were grown either in the presence (+RA) or absence (−RA) of retinoic acid at a concentration of 30 nM. FIG. 4B, top panel, shows a Northern blot using total RNA isolated from airway cultures and probed for MUC5B message expression. Cells used in the analysis were primary TBE cells, HBE1 cells and BEAS-2B (S clone) cells. The cells used in FIG. 4B were plated using BICG culture conditions contained 30 nM retinoic acid. Following analysis with the MUC5B probe, the blots used in FIGS. 4A and 4B were stripped and reprobed with an 18S rRNA cDNA probe as a reference for RNA loading normalization.

FIG. 5A shows the organization of genomic sequences contained on the Cos-1 cosmid clone. The regions corresponding to MUC5B and MUC5AC coding sequences are shown as filled bars. The 22,773 basepair portion of Cos-1 that was sequenced is indicated. FIG. 5B shows the detailed genomic organization of that part of Cos-1 that was subjected to sequence analysis and which contains MUC5B gene exons upstream of the large central exon as well as promoter sequences. Open bars and numbers indicate the exons and the size of these bars are approximately proportional to the relative sizes of the exons. The TATA box, 5' untranslated region (UTR), the initiator ATG, and large central exon are indicated.

FIGS. 6A–6H show 22,773 basepairs of human MUC5B genomic region isolated and sequenced from the Cos-1 genomic cosmid clone (SEQ ID NO: 6). This 22.7 kB encompasses 4169 basepairs of sequence upstream of the transcription start site, the 5'-UT and the 30 exons/introns upstream of the MUC5B large central exon.

FIG. 8 shows the nucleotide sequence of the MUC5B gene 5'-UTR, adjacent promoter proximal flanking region and the first exon (SEQ ID NO: 35). Only 2007 basepairs of the sequenced 22,773 basepairs are shown. Various putative DNA motifs are underlined. The transcription start site is indicated by an arrow. The predicted first exon coding region is underlined, and the corresponding predicted signal peptide amino acid sequence is shown using standard letter codes (SEQ ID NO: 36).

FIG. 10 shows the MUC5B genomic nucleotide sequence encompassing positions −1098 through +7 that were subcloned into the MUC5B-b1 luciferase reporter construct (SEQ ID NO: 31).

FIG. 11A and 11B show the MUC5B genomic nucleotide sequence encompassing positions −4169 through +7 that were subcloned into the MUC5B-b2 luciferase reporter construct (SEQ ID NO: 32).

FIG. 12 shows the MUC5B genomic nucleotide sequence encompassing positions −13 through +2738 that were subcloned into the MUC5B-i1 luciferase reporter construct (SEQ ID NO: 33).

DETAILED DESCRIPTION OF THE INVENTION

Definitions

Figure 1A:
FIGS. 1A–1C show light microscopy images of in situ nucleic acid hybridization of human bronchial tissue cross sections from a patient with no obvious airway disease or inflammation. A 48-mer oligonucleotide (SEQ ID NO: 1) corresponding to the antisense sequence of the human MUC5B tandem repeats region was used as the in situ probe.

Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described. For purposes of the present invention, the following terms are defined below.

The terms "nucleic acid," "nucleic acid sequence," "nucleotide sequence," "oligonucleotide," "polynucleotide" or "nucleic acid molecule" as used herein refer to an oligonucleotide or polynucleotide, and fragments or portions thereof, and to DNA or RNA of genomic or synthetic origin which can be single- or double-stranded, and represent the sense or antisense strand. The terms nucleic acid, polynucleotide and nucleotide also specifically include nucleic acids composed of bases other than the five biologically occurring bases (i.e., adenine, guanine, thymine, cytosine and uracil).

As used herein, the term "oligonucleotide," refers to a short length of single-stranded polynucleotide chain. Oligonucleotides are typically less than 100 nucleotides long (e.g., between 15 and 50), however, as used herein, the term is also intended to encompass longer polynucleotide chains. Oligonucleotides are often referred to by their length. For example a 24 residue oligonucleotide is referred to as a "24-mer." Oligonucleotides can form secondary and tertiary structures by self-hybridizing or by hybridizing to other polynucleotides.

As used herein, "recombinant nucleic acid," "recombinant gene" "recombinant DNA molecule" or similar terms indicate that the nucleotide sequence or arrangement of its parts is not a native configuration, and has been manipulated by molecular biological techniques. The term implies that the DNA molecule is comprised of segments of DNA that have been artificially joined together. Protocols and reagents to produce recombinant nucleic acids are common and routine in the art (See e.g., Maniatis et al.(eds.), *Molecular Cloning: A Laboratory Manual,* Cold Spring Harbor Laboratory Press, NY, [1982]; Sambrook et al. (eds.), *Molecular Cloning: A Laboratory Manual,* Second Edition, Volumes 1–3, Cold Spring Harbor Laboratory Press, NY, [1989]; and Ausubel et al. (eds.), *Current Protocols in Molecular Biology,* Vol. 1–4, John Wiley & Sons, Inc., New York [1994]).

As used herein, the term "probe" refers to an oligonucleotide (i.e., a sequence of nucleotides), which is often produced from nucleic acid isolated from cells (typically a recombinant nucleic acid), produced synthetically or in vitro, which is capable of hybridizing to a nucleic acid of interest. Probes are useful in the detection, identification and isolation of particular gene or mRNA sequences. It is contemplated that any probe used in the present invention is capable of being labeled with any "reporter molecule," so that the probe is detectable. Detection systems include, but are not limited to, the detection of enzymatic activity, fluorescence, radioactivity, and luminescence. In addition, a detection system may also comprise a specific antibody. It is not intended that the present invention be limited to any particular probe, label or detection system.

The terms "peptide," "polypeptide" and "protein" all refer to a primary sequence of amino acids that are joined by covalent "peptide linkages." In general, a peptide consists of a few amino acids, typically from 2–25 amino acids, and is shorter than a protein. "Polypeptides" encompass both peptides or proteins. As used herein, a recited "amino acid sequence" refers to an amino acid sequence of a naturally occurring protein molecule, a protein produced by recombinant molecular genetic techniques, or a synthetic or naturally occurring peptide, and may refer to a portion of a larger "peptide," "polypeptide" or "protein," and is not meant to limit the amino acid sequence to the complete, native amino acid sequence associated with the recited protein molecule.

The terms "exogenous" and "heterologous" are sometimes used interchangeably with "recombinant." An "exogenous nucleic acid," "exogenous gene" and "exogenous protein" indicate a nucleic acid, gene or protein, respectively, that has come from a source other than its native source, and has been artificially supplied to the biological system. In contrast, the terms "endogenous protein," "native protein," "endogenous gene," and "native gene" refer to a protein or gene that is native to the biological system, species or chromosome under study. A "native" or "endogenous" gene is a gene that does not contain nucleic acid elements encoded by sources other than the chromosome on which it is normally found in nature. An endogenous gene or transcript is encoded by its natural chromosomal locus, and not artificially supplied to the cell.

The term "isolated" when used in relation to a nucleic acid, as in "an isolated nucleic acid," "an isolated oligonucleotide," "isolated polynucleotide" or "isolated nucleotide sequence," refers to a nucleic acid that is identified and separated from at least one contaminant nucleic acid with which it is ordinarily associated in its natural source. Isolated nucleic acid is present in a form or setting that is different from the form or setting of that nucleic acid found in nature. In contrast, non-isolated nucleic acids are found in the state in which they exist in nature. For example, a given DNA sequence (e.g., a gene) is found on the host cell chromosome in proximity to neighboring genes; RNA sequences, such as a specific mRNA sequence encoding a specific protein, are found in the cell in a mixture with numerous other mRNAs that encode a multitude of proteins. However, isolated nucleic acid encoding a given polypeptide includes, by way of example, such nucleic acid in cells ordinarily expressing the given protein where the nucleic acid is in a chromosomal location different from that of natural cells, or is otherwise flanked by a different nucleic acid sequence than that found in nature. This isolated nucleic acid, oligonucleotide, or polynucleotide is either single-stranded or double-stranded. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide is single-stranded). In other embodiments, the oligonucleotide or polynucleotide contains both the sense and anti-sense strands (i.e., the oligonucleotide or polynucleotide is double-stranded).

As used herein, the term "purified" or "to purify" refers to the removal of at least one contaminant from a sample. As used herein, the term "substantially purified" refers to molecules, either nucleic acids or amino acid sequences, that are removed from their natural environment, "isolated" or "separated," and are largely free from other components with which they are naturally associated. An "isolated nucleic acid" or "isolated polypeptide" are therefore a substantially purified nucleic acid or substantially purified polypeptide.

Nucleic acid molecules (e.g., DNA or RNA) are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also can be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, in some embodiments, enhancer elements exert their effect even when located 3' of the promoter element or the coding region. Transcription termination and polyadenylation signals are located 3' or downstream of the coding region.

The term "gene" refers to a nucleic acid (e.g., DNA) sequence comprised of parts, that when appropriately combined in either a native or recombinant manner, provide some product or function. In some embodiments, genes comprise coding sequences necessary for the production of a polypeptide, while in other embodiments, the genes do not comprise coding sequences necessary for the production of a polypeptide. Examples of genes that do not encode polypeptide sequences include ribosomal RNA genes (rRNA) and transfer RNA (tRNA) genes. In preferred embodiments, genes encode a polypeptide or any portion of a polypeptide within the gene's "coding region" or "open reading frame." In some embodiments, the polypeptide produced by the open reading frame of a gene displays at least one functional activity (e.g., enzymatic activity, ligand binding, signal transduction, etc.), while in other embodiments, it does not.

In addition to the coding region of the nucleic acid, the term "gene" also encompasses the transcribed nucleotide sequences of the full-length mRNA adjacent to the 5' and 3' ends of the coding region. These noncoding regions are variable in size, and typically extend for distances up to or exceeding 1 kb on both the 5' and 3' ends of the coding region. The sequences that are located 5' and 3' of the coding region and are contained on the mRNA are referred to as 5' and 3' untranslated sequences (5' UT and 3' UT). Both the 5' and 3' UT may serve regulatory roles, including translation initiation, post-transcriptional cleavage and polyadenylation. The term "gene" encompasses mRNA, cDNA and genomic forms of a gene.

In some embodiments, the genomic form or genomic clone of a gene contains the sequences of the transcribed mRNA, as well as other non-transcribed sequences which lie outside of the mRNA. The regulatory regions which lie outside the mRNA transcription unit are sometimes called "5' or 3' flanking sequences." A functional genomic form of a gene must contain regulatory elements necessary for the regulation of transcription. The term "promoter/enhancer region" is usually used to describe this DNA region, typically but not necessarily 5' of the site of transcription initiation, sufficient to confer appropriate transcriptional regulation. Used alone, the term "promoter" is sometimes used synonymously with "promoter/enhancer." In some embodiments, the promoter is constitutively active, or while in alternative embodiments, the promoter is conditionally active (i.e., where transcription is initiated only under certain physiological conditions or in the presence of certain drugs). In some embodiments, the 3' flanking region contains additional sequences which regulate transcription, especially the termination of transcription. "Introns" or "intervening regions" or "intervening sequences" are segments of a gene which are contained in the primary transcript (i.e., heteronuclear RNA, or hnRNA), but are spliced out to yield the processed mRNA form. In some embodiments, introns contain transcriptional regulatory elements such as enhancers. The mRNA produced from the genomic copy of a gene is translated in the presence of ribosomes to yield the primary amino acid sequence of the polypeptide.

As used herein, the term "regulatory element" refers to a genetic element which controls some aspect of the expression of nucleic acid sequences. For example, a promoter is a regulatory element that enables the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis et al., *Science* 236:1237 [1987]). Promoter and enhancer elements have been isolated from a variety of eukaryotic sources including genes in yeast, insect and mammalian cells, as well as viruses. Analogous control elements (i.e., promoters and enhancers) are also found in prokaryotes. The selection of a particular promoter and enhancer to be operably linked in a recombinant gene depends on what cell type is to be used to express the protein of interest. Some eukaryotic promoters and enhancers have a broad host range while others are functional only in a limited subset of cell types (for review see, Voss et al., *Trends Biochem. Sci.*, 11:287 [1986] and Maniatis et al., *Science* 236:1237 [1987]). For example, the SV40 early gene enhancer is very active in a wide variety of mammalian cell types (Dijkema et al., *EMBO J*, 4:761-22-[1985]). Two other examples of promoter/enhancer elements active in a broad range of mammalian cell types are those from the human elongation factor t a gene (Uctsuki et al., *J. Biol. Chem.*, 264:5791 [1989]; Kim et al., *Gene* 91:217 [1990]; Mizushima and Nagata, Nuc. *Acids. Res.*, 18:5322 [1990]), the long terminal repeats of the Rous sarcoma virus (Gorman et al., *Proc. Natl. Acad. Sci. USA* 79:6777 [1982]), and human cytomegalovirus (Boshart et al., *Cell* 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element). For example, the long terminal repeats of retroviruses contain both promoter and enhancer functions. In some embodiments, the promoter/enhancer is "endogenous," while in other embodiments, the promoter/enhancer is "exogenous," or "heterologous." An "endogenous" promoter/enhancer is one which is naturally linked with a given gene in the genome. An "exogenous" or "heterologous" promoter/enhancer is one placed in juxtaposition to a gene by means of genetic manipulation (i.e., molecular biological techniques such as cloning and recombination) such that transcription of the gene is controlled by the linked promoter/enhancer.

The terms "in operable combination," "in operable order," "operably linked" and similar phrases when used in reference to nucleic acids herein are used to refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the terms "an oligonucleotide having a nucleotide sequence encoding a gene," "polynucleotide having a nucleotide sequence encoding a gene," and similar phrases are meant to indicate a nucleic acid sequence comprising the coding region of a gene (i.e., the nucleic acid sequence which encodes a gene product). In some embodiments, the coding region is present in a cDNA, while in other embodiments, the coding region is present in genomic DNA or RNA form. When present in a DNA form, the oligonucleotide, polynucleotide or nucleic acid is either single-stranded (i.e., the sense strand or the antisense strand) or double-stranded. In some embodiments, suitable control elements such as enhancers/promoters, splice junctions, polyadenylation signals, etc. are placed in close proximity to the coding region of the gene if needed to permit proper initiation of transcription and/or correct processing of the primary RNA transcript. Alternatively, the coding region utilized in the expression vectors of the present invention contains endogenous enhancers/promoters, splice junctions, intervening sequences, polyadenylation signals, etc. or a combination of both endogenous and exogenous control elements.

As used herein, the terms "nucleic acid molecule encoding," "DNA sequence encoding," and "DNA encoding" and similar phrases refer to the order or sequence of deoxyribonucleotides along a strand of deoxyribonucleic acid encoding a particular polypeptide. The order of the deoxyribonucleotides determines the order of the amino acids in the polypeptide chain. The DNA sequence thus codes for the amino acid sequence.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of the mRNA. Gene expression regulation often occurs at many stages. "Up-regulation" or "activation" refers to regulation that increases the production of gene expression products (i.e., RNA or protein), while "down-regulation" or "repression" refers to regulation that decreases mRNA or protein production. Molecules (e.g., transcription factors) that are involved in up-regulation or down-regulation are often called "activators" and "repressors," respectively.

As used herein, the terms "reporter gene" or "reporter" refer to a gene and/or gene product that can be readily detected in a biological system. The choice of the most suitable reporter gene to use for a particular application depends on the intended use, and other variables known to one familiar with the art. Many reporter genes are known in the art. Each reporter gene has a particular assay for the detection of that reporter. Some detection assays are enzymatic assays, while other assays can be immunological in nature (e.g., ELISA or immunohistochemical analysis).

As used herein, the term "vector " is used in reference to nucleic acid molecules that can be used to transfer DNA segment(s) from one cell to another. The terms "vehicle" or "construct" or "plasmid" are sometimes used interchangeably with "vector." In some embodiments, a vector "backbone" comprises those parts of the vector which mediate its maintenance and enable its intended use (e.g., the vector backbone contains sequences necessary for replication, genes imparting drug or antibiotic resistance, a multiple cloning site, and possibly operably linked promoter/enhancer elements which enable the expression of a cloned nucleic acid). The cloned nucleic acid (e.g., such as a cDNA coding sequence, or an amplified PCR product) is inserted into the vector backbone using common molecular biology techniques. Vectors are often derived from plasmids, bacteriophages, or plant or animal viruses. A "cloning vector" or "shuffle vector" or "subcloning vector" contain operably linked parts which facilitate subcloning steps (e.g., a multiple cloning site containing multiple restriction endonuclease sites). A "recombinant vector" indicates that the nucleotide sequence or arrangement of its parts is not a native configuration, and has been manipulated by molecular biological techniques. The term implies that the vector is comprised of segments of DNA that have been artificially joined. A "reporter construct" is a vector encoding a suitable "reporter" gene. The transcription of the reporter gene is typically regulated by heterologous promoter sequences.

The term "expression vector" as used herein refers to a recombinant DNA molecule containing a desired coding sequence and operably linked nucleic acid sequences necessary for the expression of the operably linked coding sequence in a particular host organism (e.g., a bacterial expression vector, a yeast expression vector or a mammalian expression vector). Nucleic acid sequences necessary for expression in prokaryotes typically include a promoter, an operator (optional), and a ribosome binding site, often along with other sequences. Eukaryotic cells utilize promoters, enhancers, and termination and polyadenylation signals and other sequences which are generally different from those used by prokaryotes.

The term "transfection" as used herein refers to the introduction of foreign DNA into cells. Transfection can be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, recombinant retroviral infection, and biolistics. Mammalian cell transfection techniques are common in the art, and are described in many sources (See, e.g., Ausubel et al. (eds.), Current Protocols in Molecular Biology, Chapter 9, John Wiley & Sons, Inc., New York [1994]).

The term "stable transfection" or "stably transfected" refers to the introduction and integration of foreign DNA into the genome of the transfected cell. The term "stable transfectant" refers to a cell which contains stably integrated foreign DNA within its own genomic DNA. A cell that that has been stably transfected transmits the transfected and integrated DNA to all subsequent cell generations, most typically in the presence of a selectable marker.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a eukaryotic cell, and most typically mammalian cells. The uptake of nucleic acids by cells is enhanced when the nucleic acid is presented as a calcium phosphate-nucleic acid co-precipitate. Various modifications of the original technique of Graham and van der Eb (Graham and van der Eb, Virol., 52:456 [1973]) are known in which the conditions for the transfection of a particular cell type has been optimized. The art is well aware of these various methods.

The term "transformation" has various meanings, depending on its usage. In one sense, the term "transformation" is used to describe the process of introduction of foreign DNA into prokaryotic cells (i.e., bacterial cells), and most frequently E. coli strains. Bacterial cell transformation can be accomplished by a variety of means well known in the art, including the preparation of "competent" bacteria by the use of calcium chloride, magnesium chloride or rubidium chloride, and electroporation. When a plasmid is used as the transformation vector, the plasmid typically contains a gene conferring drug resistance, such as the genes encoding ampicillin, tetracycline or kanamycin resistance. Bacterial transformation techniques are common in the art, and are described in many sources (e.g., Cohen et al., Proc. Natl. Acad. Sci. USA 69: 2110–2114 [1972]; Hanahan, J. Mol. Biol., 166:557–580 [1983]; Sambrook et al. (eds.), Molecular Cloning: A Laboratory Manual, Second Edition, Volumes 1–3, Cold Spring Harbor Laboratory Press, NY, [1989]; Ausubel et al. (eds.), Current Protocols in Molecular Biology, Vol. 1–4, John Wiley & Sons, Inc., New York [1994]).

"Transformation" also describes the physiological process by which a normal eukaryotic cell acquires the phenotypic properties of a malignant cell. Such properties include, but are not limited to the ability to grow in soft agar, the ability to grow in nutrient poor conditions, rapid proliferation, and the loss of contact inhibition. A eukaryotic cell which is "transformed" displays the properties of malignant cells. In some embodiments, eukaryotic cells acquire their transformed phenotype in vivo, while in other embodiments, the cells are artificially transformed in culture.

As used herein, the term "established" or "established culture" is a cell culture, most typically a mammalian cell culture, that has acquired the ability to grow indefinitely in culture (in contrast to a primary cell culture). An established cell culture may or may not display traits of transformed cells. Mammalian cells can be established artificially, e.g. by the stable forced expression of the SV-40 large T-antigen.

As used herein, the term "selectable marker" refers to the use of a gene that encodes an enzymatic activity that confers the ability to grow in medium lacking what would otherwise be an essential nutrient (e.g., the HIS3 gene in yeast cells); in addition, in some embodiments, a selectable marker confers resistance to an antibiotic or drug upon the cell in which the selectable marker is expressed. Furthermore, some selectable markers are "dominant." Dominant selectable markers encode an enzymatic activity that is detectable in any suitable eukaryotic cell line. Examples of dominant selectable markers include the bacterial aminoglycoside 3' phosphotransferase gene (i.e., the neo gene) that confers resistance to the drug G-418 in mammalian cells, as well as the bacterial hygromycin G phosphotransferase (hyg) gene that confers resistance to the antibiotic hygromycin, and the bacterial xanthine-guanine phosphoribosyl transferase gene (i.e., the gpt gene) that confers the ability to grow in the presence of mycophenolic acid. The use of non-dominant selectable markers must be in conjunction with a cell line that lacks the relevant enzyme activity. Examples of non-dominant selectable markers include the thymidine kinase (tk) gene (used in conjunction with tk-cell lines), the CAD gene (used in conjunction with CAD-deficient cells) and the mammalian hypoxanthine-guanine phosphoribosyl transferase (hprt) gene (used in conjunction with hprt-cell lines). A review of the use of selectable markers in mammalian cell lines is provided in Sambrook et al., *Molecular Cloning: A Laboratory Manual,* Second Edition, Cold Spring Harbor Laboratory Press, New York (1989), at pp.16.9–16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the terms "host," "expression host," and "transformant" refer to organisms and/or cells which harbor an exogenous DNA sequence (e.g., via transfection), an expression vector or vehicle, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host.

As used herein, the term "host cell" refers to any cell capable of harboring an exogenous nucleic acid or gene product. In some embodiments, the host cell also transcribes and/or translates and expresses a gene contained on the exogenous nucleic acid. It is intended that the exogenous nucleic acid be obtained from any suitable source. In some embodiments, it is produced synthetically, while in other embodiments, it is produced by another cell or organism. In addition, in some embodiments, the exogenous nucleic acid is subjected to replication, while in other embodiments, it is not.

As used herein, the term "in vitro" refers to an artificial environment and to processes or reactions that occur within an artificial environment. The term "in vivo" refers to the natural environment (e.g., in an animal or in a cell) and to processes or reactions that occur within a natural environment. The definition of an in vitro versus in vivo system is particular for the system under study.

The term "mammal" or "mammalian species" refers to any animal classified as a mammal, including humans, domestic and farm animals, and zoo, sports, or pet animals, such as dogs, cats, cattle, horses, sheep, pigs, goats, rabbits, as well as rodents such as mice and rats, etc. Preferably, the mammal is human.

As used herein, the term "inhibit" refers to the act of diminishing, suppressing, alleviating, preventing, reducing or eliminating. For example, in some embodiments, a compound that inhibits a gene promoter activity results in elimination or reduced transcription of that gene. The term "inhibit" applies equally to both in vitro and in vivo systems.

As used herein, the term "chimeric" molecule (e.g., a chimeric plasmid construct or chimeric gene or chimeric protein) refers to a molecule that comprises various elements that are not in a combination normally found in nature. For example, a luciferase reporter open reading frame under the transcriptional control of a MUC5B promoter element can be considered a chimeric gene.

As used herein, the terms, "primary," "primary culture" or "primary explant" or the like refer to a cell culture, typically a mammalian cell culture, where the cells in the culture are of low passage number (have not been maintained in culture for an extended period of time following their isolation from an organism) and where the cells are not immortal (i.e., not "established"). In one embodiment, a primary culture is derived from a tissue sample from a human subject.

The term "cell type specific" as it applies to a gene promoter refers to a promoter that imparts preferential transcriptional activity (i.e., "preferential expression" or "selective expression") onto a downstream nucleic acid in the context of one or a subset of specific cell type(s) relative to another cell type. Preferably, cell specific expression means selective expression of a nucleic acid in one specific tissue, as compared to no significant (or detectable) expression of the same nucleic acid in a different cell type. Cell-type specificity of a promoter can be evaluated in a variety of ways and in various in vitro and in vivo model systems, as known to one familiar with the art. In one embodiment, the cell type specificity of a promoter is evaluated, for example, by operably linking a reporter gene to the promoter sequence to generate a reporter construct, introducing the reporter construct into cultured cells (either stably or transiently), and detecting the expression of the reporter gene in various types of cultured cells (i.e., cultured cells of different origins). Selectivity need not be absolute. The detection of a greater level of expression of the reporter gene in one cell type (or a subset of cell types) relative to the level of expression of the reporter gene in other cell type(s) shows that the promoter is specific for the cell type(s) in which greater levels of expression are detected. A single tissue can comprise multiple cell types. The cell types being compared can come from different tissues, or be derived from the same tissue.

Alternatively, in another embodiment, the cell type specificity of a promoter is evaluated by constructing a suitable reporter construct and introducing the reporter construct into the cells of an animal. The construct can be either stably delivered (in which case the reporter is integrated into the animal genome) or transiently delivered to all cells or a subset of the cells of an animal to form a transgenic animal. The expression of the reporter gene in the cells of that animal is then assessed. The detection of a greater level of expression of the reporter gene in one (or more) cell type relative to the level of expression of the reporter gene in other cell type(s) shows that the promoter is specific for the cell type(s) in which greater levels of expression are detected. Selectivity need not be absolute.

Preferably, cell type specific expression means selective expression of a nucleic acid in a specific type of cell compared to no significant expression of the same nucleic acid in other types of cells within the same tissue. The term "cell type specific" when applied to a promoter also means a promoter capable of promoting preferential (including selective) expression of a nucleic acid in a region within a single tissue. It is clear from this definition that cell type specificity need not be absolute.

The term "tissue specific" as it applies to a gene promoter refers to a promoter that imparts preferential transcriptional activity (i.e., preferential expression) onto a downstream nucleic acid in the context of one or a subset of specific tissue type(s) relative to another tissue type. Tissue specificity of a promoter is a function of the cell type specificity of that promoter, where the promoter is more active in the cells of one tissue relative to the cells of a different tissue. A single tissue can comprise multiple cell types. A gene promoter need not be active in every cell type within a given tissue for the promoter to be considered tissue specific. Preferably, tissue specific expression means selective expression of a nucleic acid in one specific tissue, as compared to no significant (or detectable) expression of the same nucleic acid in a different tissue. Selectivity need not be absolute. Tissue specificity of a promoter can be evaluated in a variety of ways and in various in vitro and in vivo model systems, as known in the art. The detection of a greater level of expression of the reporter gene in one (or more) cell type relative to the level of expression of the reporter gene in other cell type(s) shows that the promoter is specific for the tissues in which greater levels of expression are detected.

The cell type specificity or tissue specificity of a promoter can be assessed using methods other than reporter constructs, as known in the art. For example, the specificity of a promoter within a cell type, and more commonly within a tissue, can be assessed using in situ hybridization techniques with nucleic acid probes, as known in the art. Also, the specificity of a promoter within a tissue can be assessed using immunohistochemical staining. Briefly, when using immunohistochemistry, tissue sections are embedded in paraffin, and paraffin sections are reacted with a primary antibody which is specific for the polypeptide product encoded by the nucleic acid whose expression is controlled by the promoter. A labeled (e.g., peroxidase conjugated) secondary antibody which is specific for the primary antibody is allowed to bind to the sectioned tissue and specific binding is visualized and observed microscopically (e.g., by colorimetric visualization of peroxidase activity, and/or by using an avidin/biotin labeling system).

The terms "selective expression", "selectively express" and grammatical equivalents thereof refer to a comparison of relative levels of expression in two or more regions of interest. For example, "selective expression" when used in connection with tissues refers to a substantially greater level of expression of a gene of interest in a particular tissue, or to a substantially greater number of cells which express the gene within that tissue, as compared, respectively, to the level of expression of, and the number of cells expressing, the same gene in another tissue (i.e., selectivity need not be absolute). Selective expression does not require, although it may include, expression of a gene of interest in a particular tissue and a total absence of expression of the same gene in another tissue. Similarly, "selective expression" as used herein in reference to cell types refers to a substantially greater level of expression of, or a substantially greater number of cells which express, a gene of interest in a particular cell type, when compared, respectively, to the expression levels of the gene and to the number of cells expressing the gene in another cell type.

The term "promoter activity" when made in reference to a nucleic acid sequence refers to the ability of the nucleic acid sequence to initiate transcription of a downstream deoxyribonucleic acid (DNA) sequence into a ribonucleic acid (i.e., RNA) sequence (e.g., messenger-RNA, transfer-RNA or ribosomal-RNA).

The term "sample" as used herein is used in its broadest sense. A "sample" is typically of biological origin, where "sample" refers to any type of material obtained from animals or plants (e.g., any fluid or tissue), cultured cells or tissues, cultures of microorganisms (prokaryotic or eukaryotic), and any fraction or products produced from a living (or once living) culture or cells. A sample can be a cell extract (i.e., a cell lysate), and can be purified or unpurified. An "experimental sample" is a sample where the presence, concentration and/or activity of some molecule of interest is unknown. A "control sample" is a sample where the presence, concentration and/or activity of some molecule of interest is known.

As used herein, the term "transgene" refers to a nucleic acid sequence which is partly or entirely heterologous, i.e., foreign to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can be operably linked to one or more transcriptional regulatory sequences and any other nucleic acid, such as introns, that may be necessary for optimal expression of a selected nucleic acid. A transgene can also comprise a "reporter gene," which facilitates visualization or quantitation of expression of the transgene.

Accordingly, the term "transgene construct" refers to a nucleic acid that includes a transgene, and (optionally) such other nucleic acid sequences as transcriptionally regulatory sequence, polyadenylation sites, replication origins, marker genes, etc., which may be useful in the general manipulation of the transgene for insertion in the genome of a host organism.

The term "transgenic" is used herein as an adjective to describe the property, for example, of an animal or a construct, of harboring a transgene. For instance, as used herein, a "transgenic organism" is any animal, preferably a non-human mammal, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the transgenic animals described herein, the transgene is in the form of a reporter gene, the transcription of which is driven by MUC5B promoter sequences (e.g., SEQ ID NOs: 31 or 32). The terms "founder line" and "founder animal" refer to those animals that are the mature product of the embryos to which the transgene was added, i.e., those animals that grew from the embryos into which DNA was inserted, and that were implanted into one or more surrogate hosts.

The terms "progeny" and "progeny of the transgenic animal" refer to any and all offspring of every generation subsequent to the originally transformed mammals. The term "non-human mammal" refers to all members of the class Mammalia except humans. "Mammal" refers to any animal classified as a mammal, including humans, domestic and farm animals, and zoo, sports, or pet animals, such as mouse, rat, rabbit, pig, sheep, goat, cattle and higher primates.

DESCRIPTION OF THE PREFERRED EMBODIMENTS

In its broadest aspect, the present invention relates to compositions and methods for the analysis of mucin gene expression. The present invention provides the genomic 5' regulatory domain of the human mucin-5B (MUC5B) gene. This regulatory domain is used to construct various reporter constructs which find use in drug screening. It is contemplated that MUC5B reporter constructs can be used to identify compounds which downregulate (i.e., inhibit) MUC5B gene expression. Compounds that are able to downregulate MUC5B production find use in the treatment of diseases characterized by mucin hypersecretion and airway plugging.

I. MUC5B Overexpression is Observed in Diseased Airway Tissues

Figure 1B:
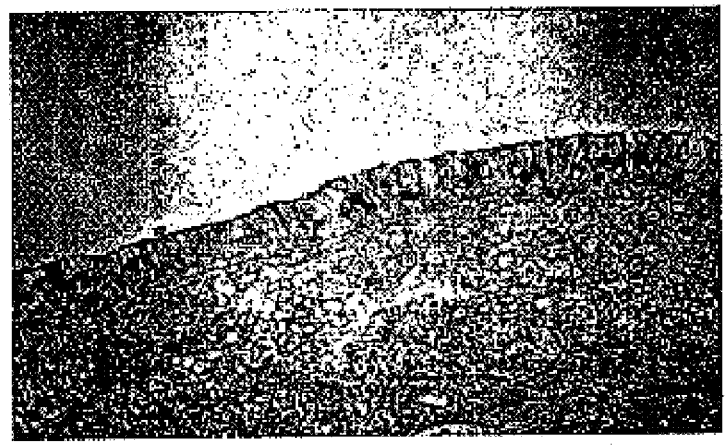
Figure 1C:

In the present study, MUC5B expression was analyzed in normal and diseased airway tissues using in situ hybridization techniques, as described in EXAMPLE 2 and FIGS. 1–3. These experiments demonstrated that MUC5B message is present in non-diseased tissue, and is predominantly expressed in the submucosal gland cells of tracheobronchial airway tissue (FIG. 1C). However, in airway tissues from patients demonstrating emphysema and ususal interstitial pneumonitis (UIP), there is a general elevated expression of MUC5B in the submucosal gland cells, and in addition, MUC5B message expression is also present in the surface goblet cell population in diseased lung tissues (see, FIGS. 3A–3C). These observations are in agreement with previous reports that suggested that the MUC5B gene product was one of the major components in mucus obtained from asthma (Sheehan et al., *Biochemical Journal* 338(Pt 2)(7):507–513 [1999]) and cystic fibrosis patients (Davies et al., *Biochemical Journal* 344 Pt 2(4697):321–330 [1999]). In contrast to MUC5B gene expression, the expression of MUC5AC message is restricted to the airway surface epithelium in normal and diseased airway tissues, and does not show elevated expression in disease states. These results suggest a significant positive correlation between elevated MUC5B gene expression and the presence of pathogenesis in airway diseases. Such an association was not seen for the expression of MUC5AC message (see, FIG. 3D).

II. Isolation of MUC5B Genomic Sequences

For the purpose of studying MUC5B transcriptional regulation and genomic structure, genomic DNA encompassing the MUC5B transcriptional start site was isolated. To isolate genomic DNA clones containing MUC5B nucleotide sequence, an initial low stringency hybridization strategy using a MUC2 amino-terminal and promoter proximal region nucleic acid probe was used to screen a Clontech human genomic library (the MUC2 and MUC5B genes contain strong homology in their promoter and amino-terminal domains). This initial screening of $10^6$ cosmid clones identified eight (8) candidate clones, which were then subjected to a secondary screening using MUC5AC cDNA sequences as a Southern blot probe under high stringency conditions. This secondary screen of the initial eight positive clones yielded only a single positive cosmid clone, which was termed Cos-1. The detailed methodology and reaction conditions used in this isolation are provided in EXAMPLE 4.

This clone was sequenced, and it was found that one end of the clone contained the 5' half of the MUC5B coding region, while the opposite end contained coding sequence from the 3' end of the adjacent MUC5AC gene. Thus, based on the known gene order on 11p15.5 of cen-MUC5AC-MUC5B-tel, it was concluded that the Cos-1 clone must contain the nucleotide sequence corresponding to the 5' promoter region of MUC5B.

Figure 5:
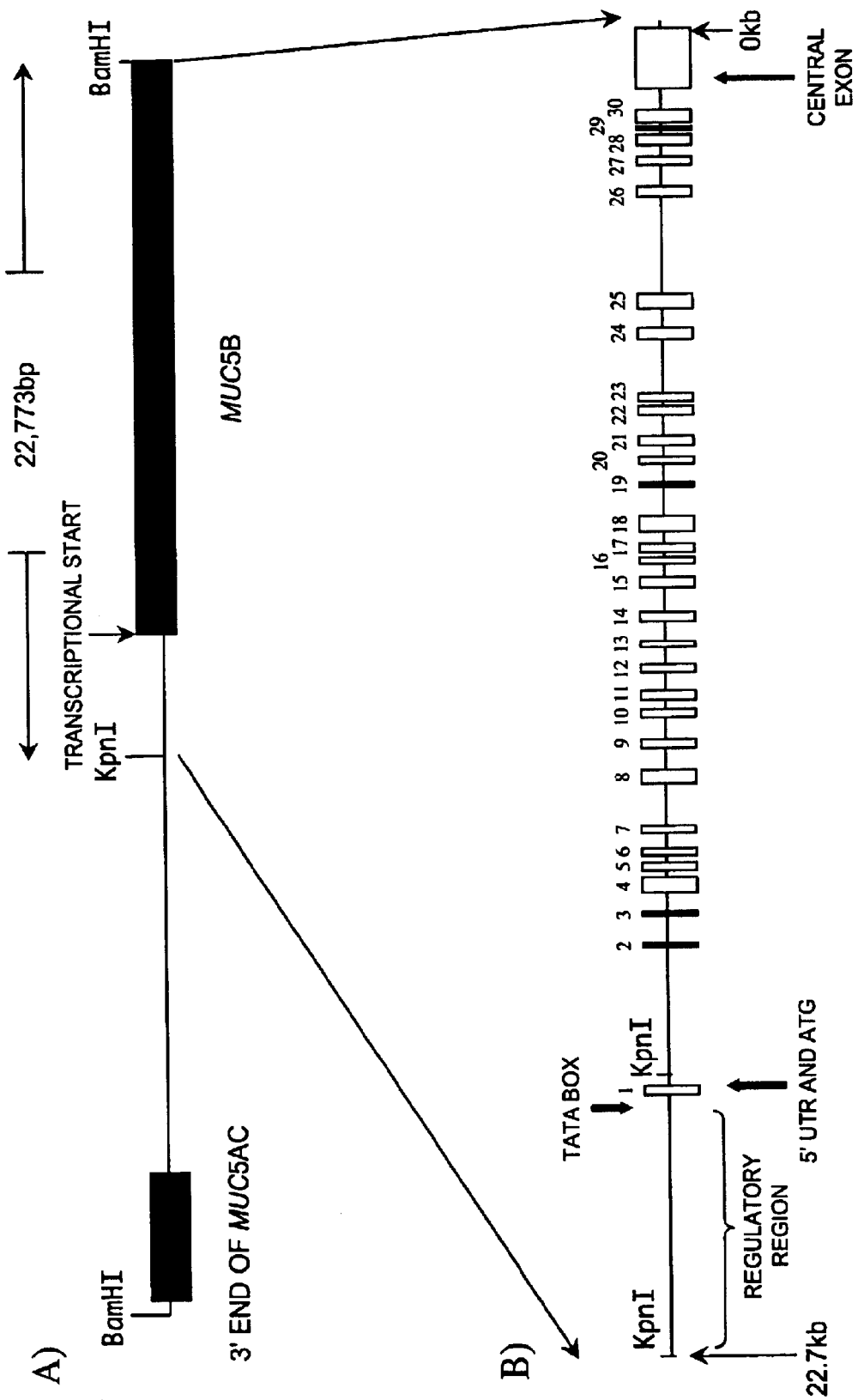
FIGS. 5A and 5B show schematic representations of the Cos-1 cosmid clone and the genomic organization of the amino-terminal and 5' flanking regions of the MUC5B gene.

The total size of the genomic insert on the Cos-1 clone was estimated to be approximately 44 kB, as determined by restriction mapping (see, EXAMPLE 4). Of this 44 kB sequence, the 5' half of the clone accounting for 22,773 basepairs, was filly sequenced. This 22.7 kB encompassed 4169 basepairs upstream of the transcription start site, the 5'-untranslated (5'-UT) region, and the first 30 N-terminal MUC5B exons (i.e., all exons/introns upstream of the large central exon). This sequence was submitted to GenBank (GenBank Accession No. AF107890; and see, FIG. 6 and SEQ ID NO: 6). A schematic representation of the Cos-1 clone and genomic organization of the MUC5B gene upstream of the large central exon is shown in FIG. 5.

Another depiction of part of the 22.7 kB sequence proximal to the transcription start site showing predicted landmarks of the gene is shown in FIG. 8 (SEQ ID NO: 35). This FIG. shows the predicted MUC5B transcription start site, a TATA box 30 nucleotides upstream of the transcription start site and a putative translation start codon ATG embedded within a Kozak consensus sequence. Furthermore, based on the deduced amino acid sequence, the extreme amino-terminal coding region contained a classic putative secretory signal sequence. This feature is consistent with the secretory nature of the mucin gene products in the airway and various other organs. Several putative motifs for various transcription factor binding sites were also identified upstream of the transcription start site, as indicated in FIG. 8 (SEQ ID NO: 35).

III. MUC5B Expression Analysis by Northern Blot

To further elucidate patterns of MUC5B gene regulation, the expression patterns of MUC5B in primary and established cultures of TBE-derived human cells were studied using Northern blotting techniques, as described in EXAMPLE 3. MUC5B gene expression was analyzed in primary cell lines derived from airway tissues (i.e., TBE cells) as well as in established cell lines, and also in a variety of culture conditions. The established tracheobronchial cell lines used in this study were BEAS-2B, which was derived from SV-40 large T-antigen immortalized bronchial epithelial cells (Ke et al., *Differentiation* 38(1):60–66 [1988]) and HBE1 cells, which are a papilloma virus immortalized tracheal epithelial cell line (Yankaskas et al., *Am. J. Physiol.*, 264:C1219–C1230 [1993]).

Total RNA was isolated from airway-derived primary cell cultures and established BEAS-2B and HBE1 tracheobronchial cell lines using a guanidinium thiocyanate phenol-chloroform extraction method. A 48-basepair MUC5B-specific probe (SEQ ID NO: 3) was derived from the tandem repeat domain of the human MUC5B large central exon. The relative abundance of MUC5B message in the samples was normalized using an 18S ribosomal RNA probe. The primary TBE cells were alternatively plated on standard 35 mm tissue culture dishes (TC), collagen-gel coated tissue culture dishes (CG), 25 mm Transwell™ chambers (Corning-COSTAR, Acton, Mass.; Catalog No. 3506) (BI) or in collagen gel-coated Transwell™ chambers (BICG). The Transwell™ chambers provide a biphasic growth environment where the cells grow in an air-liquid interface that mimics the in vivo environment. It is intended that the collagen-gel coating further mimics the in vivo environment and provides a more physiological growth environment. These cells were also grown in the presence or absence of retinoic acid.

Figure 4A:
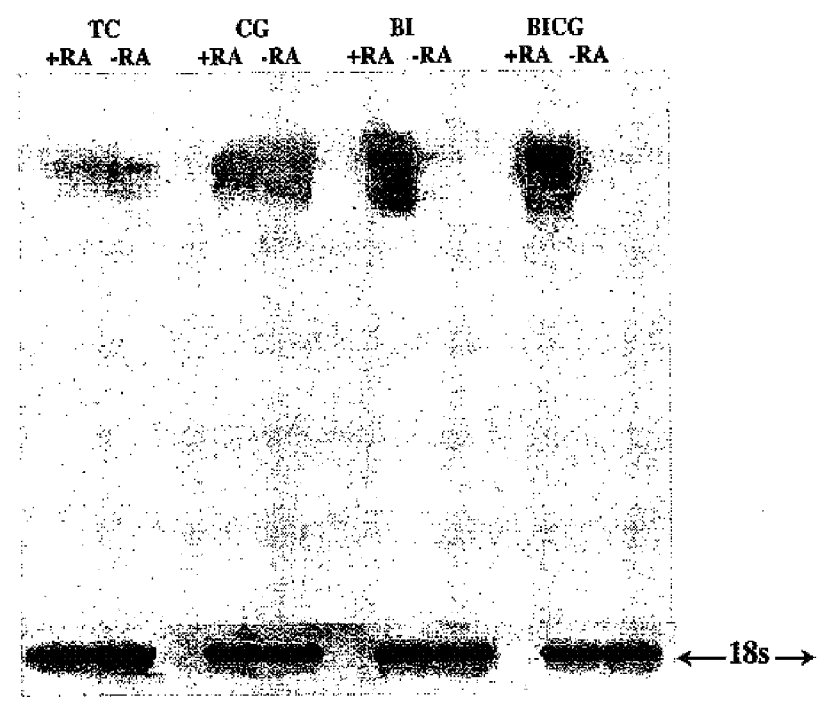
FIGS. 4A–4B show Northern blot analyses of MUC5B message expression in various human cell cultures. The top portions of these blots are probed using a 48 basepair $^{32}$P-end labeled nucleic acid probe derived from the repetitive repeat region of the human MUC5B gene.

As shown in FIG. 4A, primary human TBE cells derived from a "normal" patient expressed detectable levels of MUC5B message when cultured in the presence of retinoic acid. The levels of MUC5B message in TC and CG cultures were very low compared to the BI and BICG culture conditions, and appeared unaffected by retinoic acid. However, the levels of MUC5B message in BI and BICG cultures were greatly enhanced by the presence of retinoic acid, and furthermore, were induced to a level far in excess of the expression observed in the TC and CG culture conditions. This observation is consistent with previous studies (Koo et al., *American Journal of Respiratory Cell and Molecular Biology* 20(1):43–52 [1999] and Wu et al., *European Respiratory Journal* 10(10):2398–2403 [1997]). Thus, MUC5B message in culture was affected not only by RA, but also by the culture condition with an order of most-to-least responsive of BICG>BI>>CG>TC. The results of this Northern blot were identical when RNA from cell cultures derived from 11 diseased human tissues were used in place of the TBE cells derived from a normal subject (data not shown). Results on the Northern blot analysis of MUC5B message are also consistent with the extent of mucous cell differentiation in these cultures (data not shown).

Figure 4B:
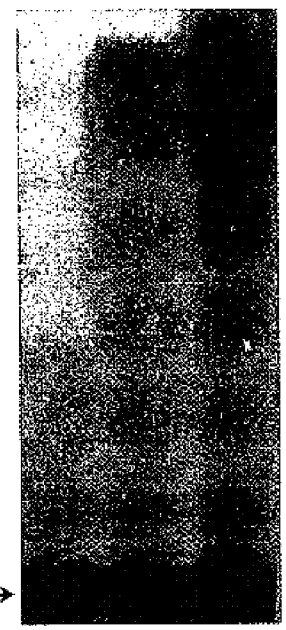

Expression of the MUC5B gene was also studied in two human TBE immortalized cell lines (HBE1 and BEAS-2B). These cultures were maintained under the BICG culture condition and were maintained in the presence of retinoic acid. Similar to the primary TBE cells, the HBE1 cell line also showed strong MUC5B expression, although slightly lower than the TBE culture (see, FIG. 4B). For the BEAS-2B subclone S cell line, MUC5B expression was undetectable in the Northern blot under all four culture conditions as described above (FIG. 4B, and data not shown).

IV. Mapping of MUC5B Transcription Start Site

Figure 7:
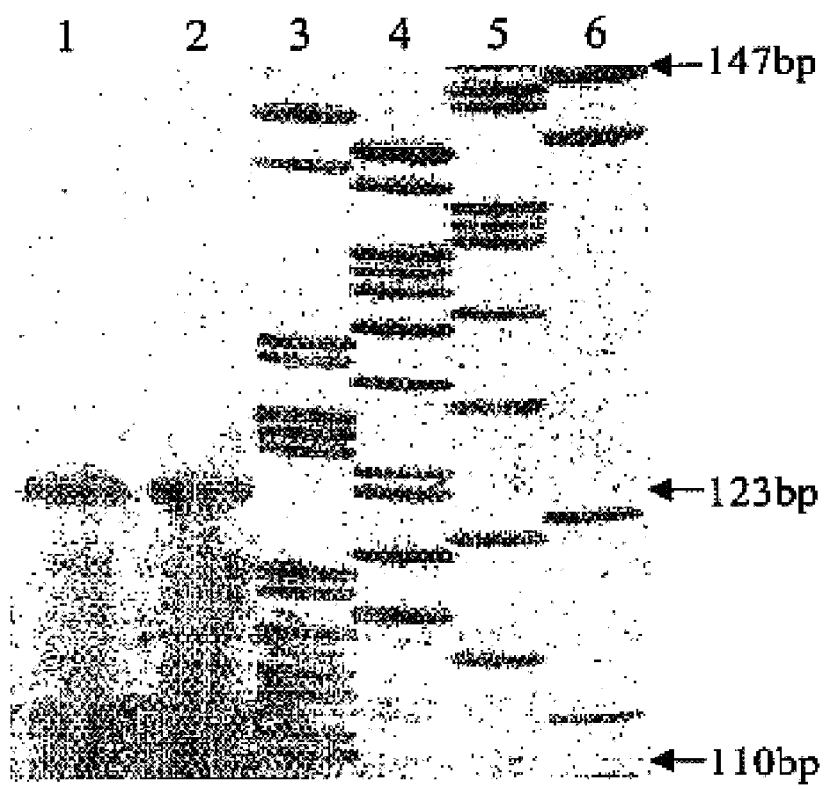
FIG. 7 shows a denaturing polyacrylamide gel electrophoresis (PAGE) containing a primer extension analysis of the MUC5B transcript. The primer used in the analysis is the Pel1 primer (SEQ ID NO: 7; and TABLE 2). The extension product shown in lane 1 used RNA template isolated from human trachea tissue. The extension product shown in lane 2 used RNA template isolated from human primary tracheobronchial epithelial (TBE) cells. Lanes 3–6 contain a Sanger dideoxynucleotide sequencing ladder in the order GATC, which was produced using a pcDNA3 vector as the nucleic acid template and the Pel1 primer. Radio-labeled dephosphorylated DNA size markers (pBR322/MspI; New England Biolabs, Inc. Beverly, Mass.) were also run, and whose sizes are indicated on the right.

A primer extension method was used to map the start site(s) of the MUC5B transcription unit, as described in EXAMPLE 5. In this primer extension protocol, total RNA isolated from human trachea tissue or from human primary tracheobronchial epithelial (TBE) cells was reverse-transcribed using a $^{32}$P end-labeled primer (the Pel1 primer; SEQ ID NO. 7, and see TABLE 2). The radiolabeled reverse-transcribed products were resolved on a denaturing gel simultaneously with a corresponding Sanger (i.e., di-deoxy) sequencing series and DNA size reference markers. The results of the primer extension analysis are shown in FIG. 7. This analysis showed the transcription start site to be located at approximately basepair position 4176, as shown in FIG. 6, and GenBank Accession No. AF107890. Significant degradation and weak signal are observed in this analysis, most likely due to the inherent difficulty in obtaining intact full-length transcripts from genes that have extremely long messages, such as the human MUC5B message (Desseyn et al., *Jour. Biol. Chem.*, 273(46):30157–30164 [1998]).

To overcome the limitations of the primer extension mRNA mapping method of EXAMPLE 5, a modified 5'-rapid amplification of cDNA ends (5'-RACE) method was developed to determine the transcription start site, as described in EXAMPLE 6.

A 5'-RACE kit (Roche Molecular Biochemicals, Indianapolis, Ind.) containing a reverse transcriptase was used to synthesize the first-strand cDNA from total RNA (3 µg) isolated from human tracheobronchial tissues or cultures of primary human TBE cells that had been cultured using air-liquid interface culture conditions. Various antisense primers were used to generate first strand cDNA. Instead of 3' tailing with only oligo d(A), the first strand cDNA was also anchored with oligo d(T) by terminal deoxynucleotidyl transferase.

After tailing, the resulting double stranded cDNA products were used in polymerase chain reactions (PCR) with nested primers within the 3'-end and the 5'-anchor oligo d(T) adapter. PCR amplification was carried out using various primer combinations (see, TABLE 2). The resulting PCR products were subcloned into the TA Cloning® vector (Invitrogen, Carlsbad, Calif.) and sequenced. Since there should be only one common DNA sequence adjacent to oligo d(T) and oligo d(A) adapters, this DNA sequence should be identical to that of the 5'-end message upstream to the +250/+230 primer. A major advantage of this approach is the use of POR, which allows the amplification of the 5'-ends of low abundance messages. The sequence analysis of the PCR products generated above identified a transcription start site located at approximately basepair position 4176, as shown in FIG. 6, and GenBank Accession No. AF107890 (and see, FIG. 8). This position is in agreement with the primer extension analysis described in EXAMPLE 5. Both approaches yielded the same conclusion, suggesting that the transcription start site is 18604 basepairs upstream of the large central exon (using the numbering convention of FIG. 8). This putative transcription start site is different from the sites previously reported (Offner et al., *Biochem. Biophys. Res. Comm.*, 251(1):350–355 [1998]; and Van Seuningen et al., *Biochemical Jour.*, 348 Pt 3(12):675–686 [2000]).

V. Construction of MUC5B Chimeric Reporter Constructs

In order to study the transcriptional regulation of the MUC5B gene, and also to define minimal promoter elements controlling MUB5B transcription in response to environmental conditions, luciferase reporter constructs under the transcriptional control of MUC5B gene sequences were constructed, as described in EXAMPLE 7. The gene sequences used to make these reporter constructs were derived from the isolated genomic DNA described in EXAMPLE 4.

Fragments of the human MUC5B gene corresponding to different 5'-flanking regions as well as a region downstream of the transcription start site (including exon 1) were PCR amplified using appropriate primer pairs (see, TABLE 2). The PCR products were subcloned into the promoterless pGL-3 basic vector (Promega, Madison, Wis.), which contains the luciferase gene open reading frame. Thus, the luciferase gene is under the transcriptional control of the subcloned nucleic acid upstream of the luciferase open reading frame. Three constructs were made, as listed in TABLE 3, and shown in FIG. 9. These reporter constructs, and the MUC5B genomic sequences contained in each reporter, were:

MUC5B-b1 (−1098 to +7). See SEQ ID NO: 31 and FIG. 10.

MUC5B-b2 (−4169 to +7). See SEQ ID NO: 32 and FIG. 11.

MUC5B-i1 (−13 to +2738). See SEQ ID NO: 33 and FIG. 12.

The MUC5B-b1 and MUC5B-b2 constructs comprise various extents of MUC5B sequence upstream of the predicted transcription start site. In addition, the third construct, MUC5B-i1, comprises sequences downstream of the presently predicted transcription start site. This last construct was made to test whether these downstream sequences contain elements capable of promoting transcription initiation of the MUC5B gene, as proposed in previously published reports (Desseyn et al., *Jour. Biol. Chem.*, 273(46):30157–30164 [1998]; and Van Seuningen et al., *Biochemical Jour.*, 348 Pt 3(12):675–686 [2000]).

In addition, a MUC5B promoter reporter construct driving the expression of a GFP reporter gene is also provided by the invention. This GFP reporter construct is under the transcriptional control of the −4169 to +7 promoter region (see, SEQ ID NO: 32 and FIG. 11). This GFP reporter is analogous to the luciferase reporter MUC5B-b2.

VI. Analysis of MUC5B Chimeric Reporter Constructs in Transient Transfection Assays The activity of the MUC5B reporter constructs described above and in EXAMPLE 7 was assessed in cultured primary TBE cells and established TBE cell lines following transient transfection according to the methods provided in EXAMPLE 8. In addition, the MUC5B luciferase reporter activity of the constructs was also assayed in response to various culture conditions. The chimeric reporter plasmids used in the transfections were purified using QIAGEN® plasmid isolation kits, and the transient transfections were done using Roche FuGENE 6™ transfection reagent (Roche Molecular Biochemicals, Indianapolis, Ind.), all according to the manufacturer's instructions. In these transient transfections, a cotransfected pSV-β-galactosidase (β-gal) expression vector was included for the normalization of transfection efficiency. Cell extracts prepared from the various transfected cell cultures were assayed for both luciferase and β-galactosidase reporter gene activities (see, EXAMPLE 8).

Figure 13:
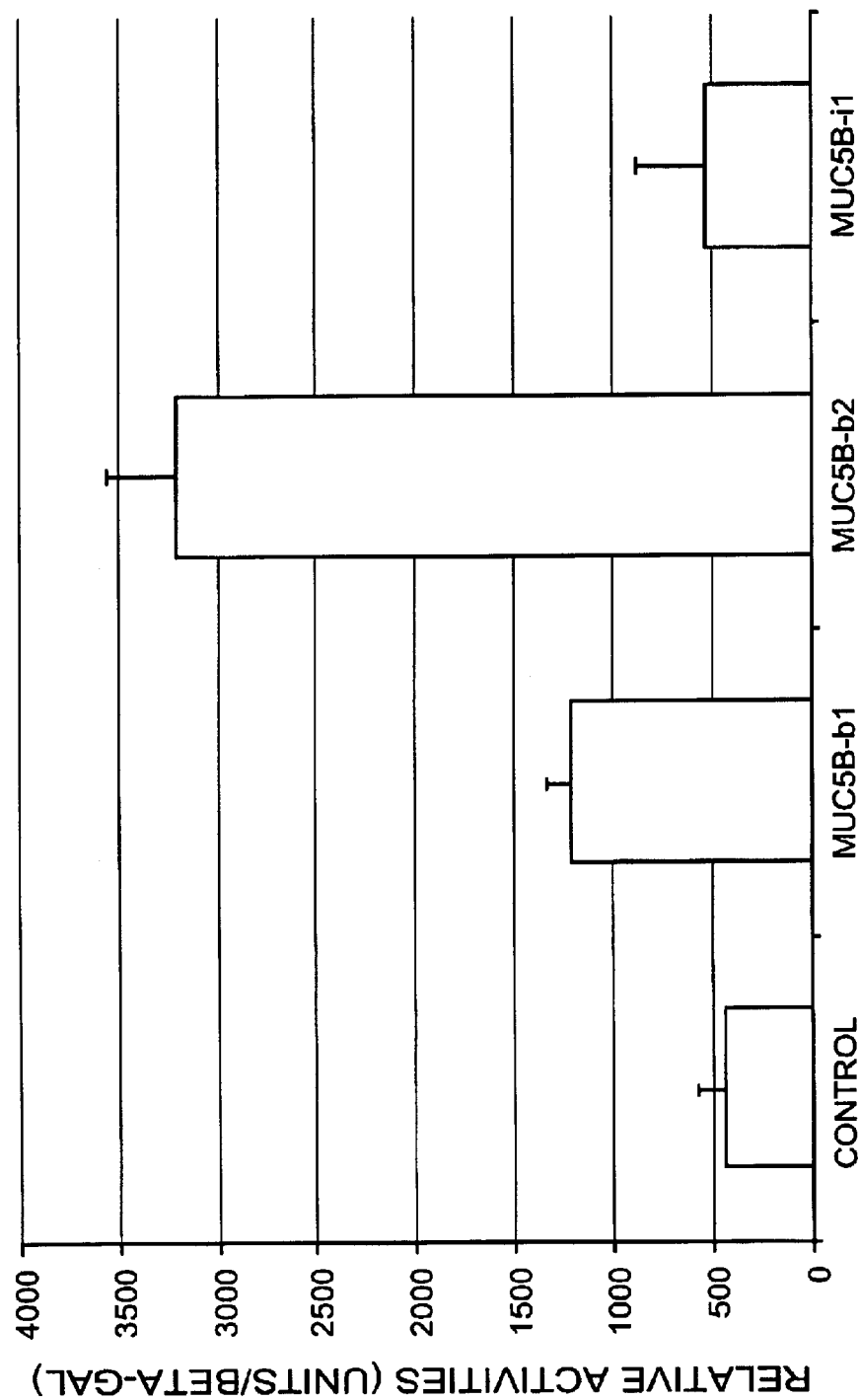
FIG. 13 shows the results of a transfection assay using the chimeric MUC5B luciferase reporter constructs shown in FIG. 9 and primary TBE cells. The TBE cells were also co-transfected with a β-galactosidase expression vector, and luciferase activity was normalized against β-galactosidase activity to take into account transfection efficiency variability. Relative activities of each of the reporter constructs following transfection in the TBE cells is shown, and activity is expressed as units of luciferase activity per unit of β-gal activity (units/beta-gal).

FIG. 13 shows the results of a transfection assay using cultured primary TBE cells and the chimeric MUC5B reporter constructs. The primary TBE cells were maintained on standard 35 mm tissue culture dishes (without retinoic acid). As can be seen in the FIG. 13, the reporter gene activity in MUC5B-b1 and MUC5B-b2 transfected cells was two- to five-fold higher, respectively, than those transfected with the promoterless control construct, pGL-3 (labeled "control"). No significant activity was observed in the transfection using the MUC5B-i1 construct. These results indicate that the regions −1098 to +7 and −4169 to +7 both have promoter activity, and the −4169 to +7 region contains stronger promoter activity than does the −1098 to +7 region. Furthermore, the −13 to +2738 region contained no detectable promoter activity under these conditions.

Figure 14:
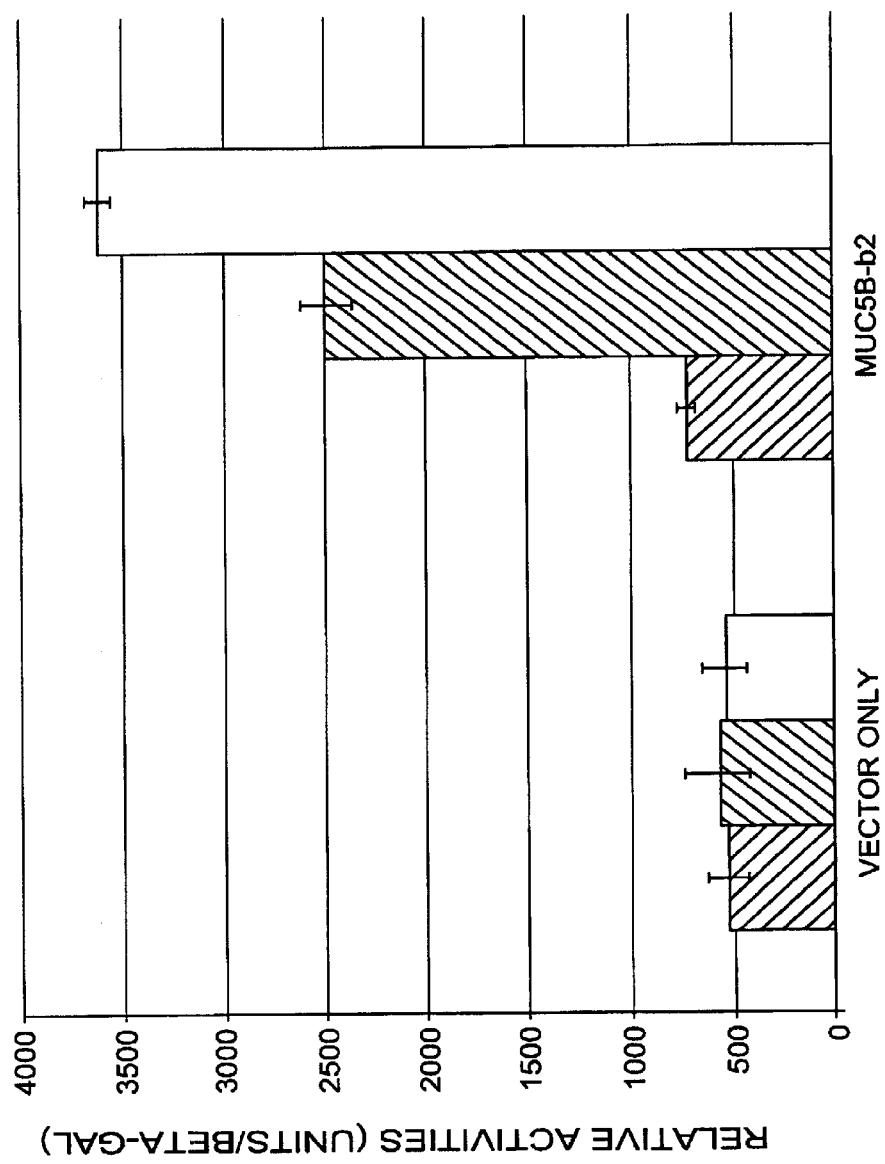
FIG. 14 shows the results of a transfection assay using the MUC5B-b2 luciferase reporter construct shown in FIG. 9 and three different cell types. These were primary TBE cells (unfilled bars), HBE1 cells (striped bars) and BEAS-2B (S clone) cells (black bars). The cells were also co-transfected with a β-galactosidase expression vector, and luciferase activity was normalized against β-galactosidase activity to take into account transfection efficiency variability, and activity is expressed as units of luciferase activity per unit of β-gal activity (units/beta-gal). Transfections were done in triplicate, and the mean results of two independent experiments are shown.

FIG. 14 shows an analysis of MUC5B-b2 reporter activity in various cell types, which were primary TBE cells (unfilled bars), HBE1 cells (striped bars) and BEAS-2B (S clone) cells (black bars), all grown in 35 mm tissue culture dishes without retinoic acid. As can be seen in FIG. 14, the MUC5B-b2 promoter was most active in the primary TBE cells, followed by activity observed in the HBE1 cells. No significant promoter activity was observed in the BEAS-2B cells. These results are consistent with the Northern blot data (FIG. 4), which suggests cell type-specific MUC5B regulation.

Figure 15:
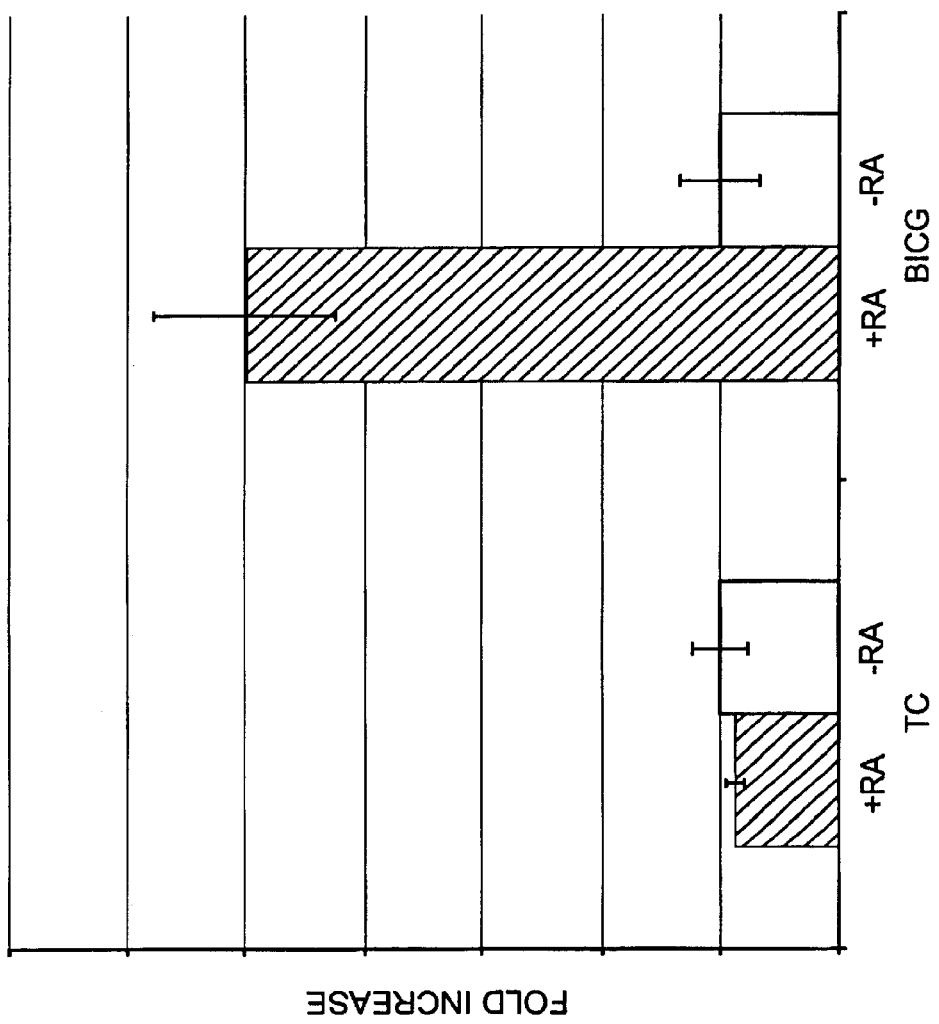
FIG. 15 shows the results of a transfection study using the MUC5B-b2 luciferase reporter construct shown in FIG. 9 and primary human TBE cells. The TBE cells were maintained in two different culture conditions, which were standard tissue culture dishes (TC) or collagen gel-coated Transwell™ chambers (BICG). Activity of the MUC5B-b2 reporter construct was observed in the cultures maintained in the presence (+RA) or absence (−RA) of retinoic acid. The luciferase reporter gene activity in each transfected culture was normalized to the activity of a cotransfected β-galactosidase expression vector. Results are expressed as "fold increase" of luciferase activity, comparing RA-treated and RA-untreated cultures. The activity of the MUC5B-b2 reporter in RA-untreated culture in the TC conditions was normalized to 1. Transfections were done in triplicate, and the mean results of two independent experiments are shown.

FIG. 15 shows the results of an experiment examining the effects of cell culture conditions on MUC5B-b2 promoter activity in primary human TBE cells. The TBE cells were maintained in either standard tissue culture dishes (TC) or collagen gel-coated Transwell™ chambers (BICG), and activity of the MUC5B-b2 reporter construct was observed. Furthermore, the cultures were maintained either in the presence or absence of retinoic acid (RA). As can be seen in FIG. 15, when TBE cells were plated on tissue culture dishes, the reporter gene activity was not affected by the addition of retinoic acid. In contrast, the reporter gene activity was elevated five-fold by retinoic acid treatment when transfected cells were maintained under BICG conditions. This culture condition-dependent promoter activity was consistent with the Northern blot data, which showed that culture conditions influenced retinoic acid-dependent MUC5B gene expression.

Thus, the largest of the reporter constructs, MUC5B-b2, contained sufficient MUC5B promoter region (i.e., approximately 4 kB) to drive the transcription of the luciferase open reading frame in a cell type-specific manner. Furthermore, this promoter region was sufficient to respond to various culture conditions, including various growth substratum and nutrient states (e.g., the presence or absence of retinoic acid). These data demonstrate the importance of the biphasic air-liquid interface in regulating MUC5B gene expression.

MUC5B reporter constructs using the GFP open reading frame can also be used to assess promoter activities, both qualitatively and quantitatively. GFP production can be visualized in a fluorescence microscope in either tissues or individual cells as well as quantitated from crude cell extracts prepared from cultured cells or tissues (see, EXAMPLE 10). Furthermore, the expression of luciferase or GFP can also be visualized using immunohistochemical techniques, especially in the analysis of tissue sections.

VII. Construction and Analysis of Transgenic Animals Carrying Chimeric Reporter Constructs In order to study the transcriptional regulation of the MUC5B gene in the context of a mammalian organism, transgenic animals carrying MUC5B reporter constructs were produced using methods well known to one familiar with the art. The reporter constructs used in this study (both luciferase and GFP reporter constructs) are described in EXAMPLE 7 The generation of the respective transgenic mice is described in EXAMPLE 9.

Transgenic animal technology, including the construction (i.e., establishment) of a desired transgenic animal line (e.g., a mouse line), is common in the art, and the protocols used to establish such transgenic lines are described in many sources (see, for example, Hogan et al., *Manipulating the Mouse Embryo,* Cold Spring Harbor Laboratory, Cold Spring Harbor, N.Y., [1986]). General discussion of such protocols is provided below. In addition, the actual procedure used to produce the transgenic animals of the invention are provided in EXAMPLE 9. Although the making of transgenic animals is illustrated herein with reference to transgenic mice, this is only for illustrative purpose, and is not to be construed as limiting the scope of the invention. This specific disclosure can be readily adapted by those skilled in the art to incorporate MUC5B-reporter transgene sequences into any non-human mammal utilizing the methods and materials described herein.

A. Cells Used for Introduction of Transgene

The transgenic animals of the present invention all include within a plurality of their cells a transgene of the present invention (e.g., a MUC5B promoter reporter construct, as described in EXAMPLE 7). In an exemplary embodiment, the transgenic mammals of the invention were produced by introducing a MUC5B-reporter transgene into the germline of the mammal. Embryonal target cells at various developmental stages can be used to introduce a MUC5B-reporter transgene. Different methods are used depending on the stage of development of the embryonal target cell. The specific line(s) of any animal used to practice this invention are selected for general good health, good embryo yields, good pronuclear visibility in the embryo, and good reproductive fitness.

In one embodiment, the transgene construct is introduced into a single stage embryo. Generally, the female animals are superovulated by hormone treatment, mated and fertilized eggs are recovered. For example, in case of mice, females six weeks of age are induced to superovulate with a 5 IU injection (0.1 ml, i.p.) of pregnant mare serum gonadotropin (PMSG; Sigma) followed 48 hours later by a 5 IU injection (0.1 ml, i.p.) of human chorionic gonadotropin (hCG; Sigma). FVB strain of mice are used in this case. Females are then mated immediately with a stud male overnight. Such females are next examined for copulation plugs. Those that have mated are euthenized by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Normally, fertilized embryos are incubated in suitable media until the pronuclei appear. At about this time, the transgene is introduced into the female or male pronucleus as described below. In some species such as mice, the male pronucleus is preferred. For example, the exogenous genetic material is added to the early male pronucleus, as soon as possible after the formation of the male pronucleus, which is when the male and female pronuclei are well separated and both are located close to the cell membrane. Alternatively, the exogenous genetic material is added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

In addition to similar biological considerations, physical ones also govern the amount (e.g., volume) of exogenous genetic material, which can be added to the nucleus of the zygote, or to the genetic material which forms a part of the zygote nucleus. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional.

B. Methods of Introducing Transgene

Each transgene construct to be inserted into the cell must first be in the linear form since the frequency of recombination is higher with linear molecules of DNA as compared to the circular molecules. Therefore, if the construct has been inserted into a vector, linearization is accomplished by digesting the DNA with a suitable restriction endonuclease selected to cut only within the vector sequence and not within the transgene sequence.

Introduction of the transgene into the embryo may be accomplished by any means known in the art so long as it is not destructive to the cell, nuclear membrane or other existing cellular or genetic structures. Some of the widely used methods include microinjection, electroporation, or lipofection. Following introduction of the transgene, the embryo may be incubated in vitro for varying amounts of time, or reimplanted into the surrogate host, or both. One common method is to incubate the embryos in vitro for about 1–7 days, depending on the species, and then reimplant them into the surrogate host.

The zygote is the best target for introducing the transgene construct by microinjection method. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., *Proc. Natl. Acad. Sci. USA* 82: 4438–4442 [1985]). As a consequence, all cells of the transgenic animal will carry the incorporated transgene. This will in general also be reflected in the efficient transmission of the transgene to offspring of the founder since 50% of the germ cells will harbor the transgene.

Retroviral infection can also be used to introduce transgene into a non-human mammal. The developing non-human embryo can be cultured in vitro to the blastocyst stage. During this time, the blastomeres can be targets for retroviral infection (Jaenich, *Proc. Natl. Acad. Sci. USA* 73: 1260–1264 [1976]). Efficient infection of the blastomeres is obtained by enzymatic treatment to remove the zona pellucida (*Manipulating the Mouse Embryo,* Hogan (ed.), Cold Spring Harbor Laboratory Press, Cold Spring Harbor, [1986]). The viral vector system used to introduce the transgene is typically a replication-defective retrovirus carrying the transgene (Jahner et al., *Proc. Natl. Acad. Sci. USA* 82: 6927–6931 [1985]; Van der Putten et al., *Proc. Natl. Acad. Sci. USA* 82: 6148–6152 [1985]). Transfection is easily and efficiently obtained by culturing the blastomeres on a monolayer of virus-producing cells (Van der Putten, supra; Stewart et al., *EMBO J.,* 6: 383–388 [1987]). Alternatively, infection can be performed at a later stage. Virus or virus-producing cells can also be injected into the blastocoele (Jahner et al., *Nature* 298: 623–628 [1982]). Most of the founders will be mosaic for the transgene since incorporation occurs only in a subset of the cells which formed the transgenic animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al., (1982) supra).

Insertion of the transgene construct into the ES cells can be accomplished using a variety of methods well known in the art including for example, electroporation, microinjection, and calcium phosphate treatment. A preferred method of insertion is electroporation, in which the ES cells and the transgene construct DNA are exposed to an electric pulse using an electroporation machine and following the manufacturer's guidelines for use. After electroporation, the ES cells are typically allowed to recover under suitable incubation conditions. The cells are then screened for the presence of the transgene.

C. Implantation of Embryos

Pseudopregnant, foster or surrogate mothers are prepare or the purpose of implanting embryos, which have been modified by introducing the transgene. Such foster mothers are typically prepared by mating with vasectomized males of the same species. The stage of the pseudopregnant foster mother is important for successful implantation, and it is species dependent. For mice, this stage is about 2–3 days pseudopregnant. Recipient females are mated at the same time as donor females. Although the following description relates to mice, it can be adapted for any other non-human mammal by those skilled in the art. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmaker's forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures. The number of embryos implanted into a particular host will vary by species, but will usually be comparable to the number of off spring the species naturally produces.

Where the ES cell have been used to introduce the transgene, the transformed ES cells are incorporated into the embryo as described earlier, and the embryos may be implanted into the uterus of a pseudopregnant foster mother for gestation.

D. Screening for the Presence or Expression of Transgene

Transgenic offspring of the surrogate host may be screened for the presence and/or expression of the transgene by any suitable method. Offspring that are born to the foster mother may be screened initially for mosaic coat color where a coat color selection strategy has been employed. Alternatively, or additionally, screening is often accomplished by Southern blot or PCR of DNA prepared from tail tissue, using a probe that is complementary to at least a portion of the transgene. Western blot analysis or immunohistochemistry using an antibody against the protein encoded by the transgene may be employed as an alternative or additional method for screening for the presence of the transgene product. Alternatively, the tissues or cells believed to express the transgene at the highest levels are tested for the RNA expression of the transgene using Northern analysis or RT-PCR.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

E. Breeding of the Transgenic Animals

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods. Typically, crossing and backcrossing is accomplished by mating siblings or a parental strain with an offspring, depending on the goal of each particular step in the breeding process.

F. Cell Lines and Cell Cultures

The animals of this invention can be used as a source of cells, differentiated or precursor, which can be immortalized in cell culture if desired. Cells containing a MUC5B-reporter can be isolated from the transgenic animal and established in vitro as cell lines and used for drug screening. Thus, the transgenic animals of this invention can be used as a source of cells for cell culture. Tissues of transgenic mice are analyzed for the presence and/or expression of the MUC5B-reporter transgene as described, and cells or tissues carrying the reporter transgene are cultured, using standard tissue culture techniques (see, EXAMPLE 10).

VIII. Construction and Analysis of Stably Transfected Established TBE Cell Lines Carrying Chimeric MUC5B Promoter Reporter Constructs The present invention provides a stably transfected established TBE cell line, namely the HBE 1 cell line, carrying MUC5B reporter constructs (i.e., the constructs described in EXAMPLE 7). Both luciferase and GFP reporter lines were created, where the reporter genes are driven by the MUC5B 4,169 to +7 promoter region. Methods for the construction of the stably transfected cell lines, and a description of MUC5B reporter gene activity in these lines, is provided in EXAMPLE 11. Furthermore, the activity of the stably transfected reporter constructs was analyzed in response to cytokines and environmental stimuli, including interleukin-6 (IL-6), IL-17 and tobacco smoke. It was observed that these stable cell lines expressed detectable levels of the reporter gene, and were strongly induced by the addition of the proinflammatory cytokines IL-6 and IL-17.

IX. Isolation and Analysis of Stably Transfected Primary Cell Cultures Carrying Chimeric MUC5B Promoter Reporter Constructs The present invention provides compositions and methods for the isolation and reporter gene analysis of stably transfected mouse primary cell cultures carrying the MUC5B luciferase or GFP reporter constructs (i.e., the constructs described in EXAMPLE 7). These primary transgenic cell cultures were derived from the transgenic mice described in EXAMPLE 9. This analysis of reporter gene activity included observation of reporter gene activity in response to various culture conditions.

Figure 16:
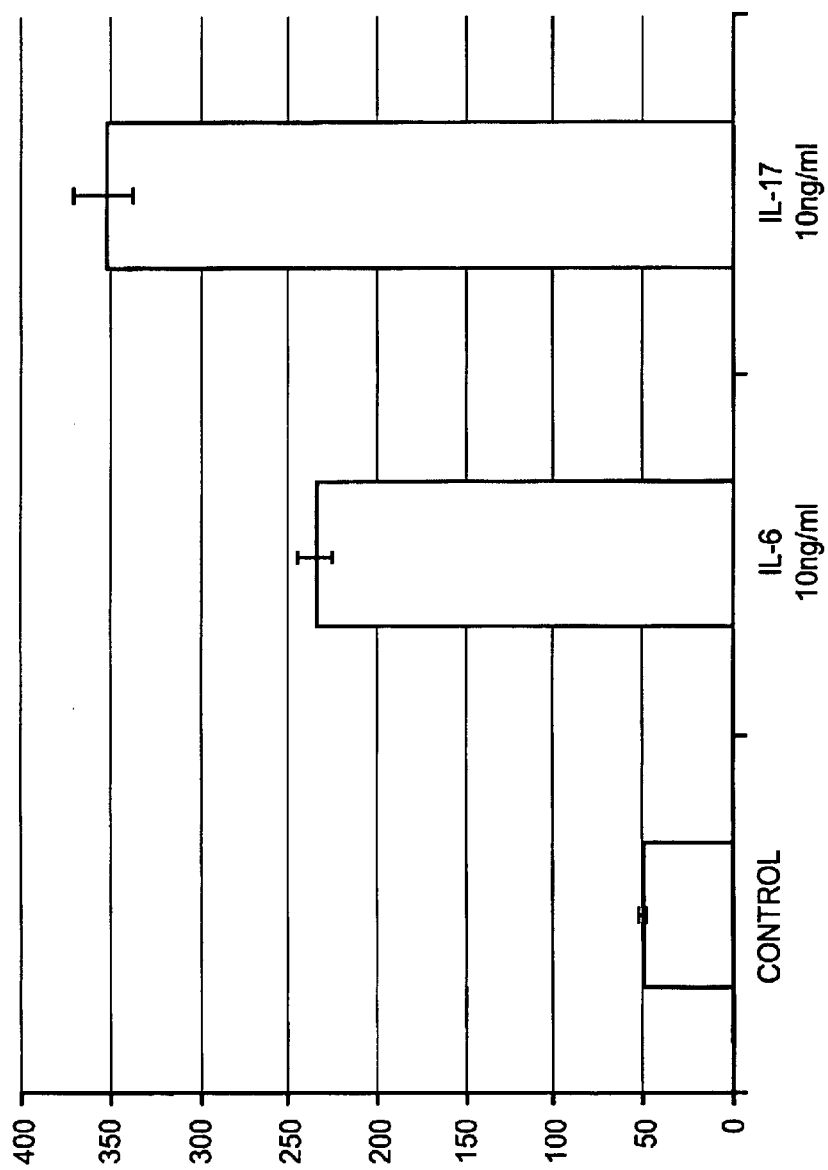
FIG. 16 shows the results of an analysis of MUC5B-b2 luciferase reporter activity in the context of stably integrated cells derived from transgenic animals. Transgenic mice carrying the MUC5B 4,169/+7 promoter luciferase reporter were used to isolate and culture primary TBE cells. The TBE cultures were maintained in three different conditions, which were with interleukin-6, with interleukin-12 or without any interleukin (control). Cells were harvested and extracts prepared. Luciferase activity was determined for each culture, normalized for total protein in the samples, and graphed.

In one use of these transgenic cells, the transgenic mice were used to isolate TBE cells, which were maintained in culture. The TBE cells were maintained with and without interleukin-6 (IL-6) or IL-17. After a period of time in culture, the cells were harvested, cell extracts were prepared, and luciferase activity was assayed in each cell extract sample. FIG. 16 shows the results of this analysis. As can be seen in the Figure, the addition of the pro-inflammatory cytokines IL-6 or IL-17 to the cell cultures resulted in significant upregulation of the MUC5B promoter activity. It is contemplated that this situation mimics the in vivo situation, where IL-6 and IL-17 expression are frequently observed in conjunction with infection and other diseases associated with mucin hyperexpression. Thus, it is possible that IL-6 or IL-1 7 is responsible for the elevated MUC5B expression seen in various airway disease states.

X. Compositions and Methods for Cell and Tissue-Restricted Expression of Heterologous Gene Products The present invention provides compositions and methods for the cell-type and tissue-restricted expression of a desired gene product. As demonstrated in EXAMPLE 2, MUC5B expression is restricted to the epithelia or glandular mucosal surfaces, e.g., the epithelial mucosal surfaces of the airway. It is contemplated that the MUC5B genomic region −4,169 through +7 can direct expression of a cloned downstream gene product to epithelial or glandular mucosal surfaces.

It is further contemplated that the delivery of certain gene products, other than reporter gene products, under the control of the MUC5B −4169/+7 promoter region finds use in the treatment of disease. For example, delivery of a cell-type restricted expression vector encoding an apoptosis-inducing gene product to the cells of a mucinous airway tumor will suppress and possibly eradicate the tumor in the patient. Furthermore, as expression of the death-inducing gene product can be restricted to glandular mucosal epithelia, the risk of adversely effecting non-glandular mucosal epithelial cells in a patient is minimized.

In another example, it is contemplated that the −4169/+7 promoter region contains DNA elements that mediate interaction with positive or negative acting transcription factors that control transcription of the MUC5B gene (see, FIG. 8), and allow the gene to respond to various environmental stimuli, such as growth conditions and the presence of cytokines or other biological agents. Indeed, this is evidenced by the results of experiments described in EXAMPLES 8, 10 and 11. It is contemplated that cell-type specific expression of a negative regulatory protein using a MUC5B-driven expression vector to a patient suffering from a disease characterized by mucus hypersecretion will result in downregulation of mucus production, and therapeutic benefit to the patient. Similarly, expression of an antisense transcript specific for a positive-acting transcription factor (or the MUC5B transcript itself) will also result in therapeutic benefit to a patient suffering from a disease characterized by MUC5B hypersecretion. Antisense technology has been shown to be an effective means for the downregulation of gene expression.

XI. Methods for Drug Screening Using MUC5B Chimeric Reporter Constructs

The present invention provides novel compositions and methods that find use in the assessment of MUC5B gene transcription in response to various culture conditions or treatments. It is contemplated that MUC5B reporter constructs can be used to identify compounds which downregulate (i.e., inhibit) MUC5B gene expression. Compounds that are able to downregulate MUC5B production find use in the treatment of chronic airway diseases characterized by mucin hypersecretion and/or airway plugging. Examples of such diseases include, but are not limited to, cystic fibrosis, bronchial pneumonia, asthma, chronic bronchitis and emphysema. However, it is not intended that the invention be limited to any particular mechanism or mechanisms by which a compound is able to downregulate (i.e., inhibit) MUC5B promoter activity. Indeed, it is not necessary to have an understanding of the mechanism or mechanisms controlling MUC5B gene regulation in order to make and use the present invention.

The drug screening methods of the present invention comprise the assessment of activity of a MUC5B promoter reporter construct in a suitable cell, in the absence and presence of a test compound. The reporter activities in these two cultures are then compared. A compound that results in the inhibition of the MUC5B reporter construct activity is a candidate for further development as a therapeutic agent for the treatment of diseases resulting from mucin, and specifically MUC5B, hypersecretion. In a preferred embodiment, the drug screening methods comprise the identification of a compound that is able to inhibit the upregulation of reporter gene activity (i.e., the MUC5B hyperexpression) observed in response to various stimuli, such as exposure to IL-6, IL-17 or tobacco smoke. It is contemplated that compounds identified in the screening that are able to inhibit MUC5B expression can be delivered to a patient in need of such treatment by oral, parenteral or inhalation means.

In one embodiment, contacting the compound with the MUC5B reporter construct under study will result in at least a 2-fold inhibition of the MUC5B promoter activity, preferably at least 5-fold inhibition, more preferably at least 10-fold inhibition, and most preferably at least 50-fold or greater inhibition of MUC5B promoter activity.

The test compound (i.e., a candidate drug) used in the screening is not particularly limited to any type of molecule. However, compounds having low toxicity towards human cells and humans are preferred. A test compound can be organic or inorganic. Test compounds encompass numerous chemical classes, though typically they are organic molecules, preferably small organic compounds having a molecular weight of more than 50 and less than about 2,500 daltons. Candidate compounds may comprise functional groups necessary for structural interaction with proteins. The candidate compound often comprises cyclical carbon or heterocyclic structures and/or aromatic or polyaromatic structures substituted with one or more functional groups. Candidate compounds are also found among biomolecules including peptides, saccharides, fatty acids, steroids, purines, pyrimidines, derivatives, structural analogs or combinations thereof.

Candidate compounds are obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs for testing in the methods of the preset invention.

1. Reporter Constructs

The present invention provides MUC5B reporter constructs suitable for use in drug screening protocols. In one preferred embodiment, the present invention provides a luciferase reporter construct driven by MUC5B sequences −4169 to +7, relative to the site of transcription initiation (i.e., the MUC5B-b2 reporter construct). This promoter sequence is provided in SEQ ID NO: 32, and is shown in FIG. 11. In another embodiment, the present invention provides a luciferase reporter construct driven by MUC5B sequences −1098 to +7, relative to the site of transcription initiation (i.e., the MUB5B-b1 reporter construct). This promoter sequence is provided in SEQ ID NO: 31, and is shown in FIG. 10.

In other embodiments, the present invention provides a green fluorescent protein (GFP) reporter construct driven by MUC5B sequences −4169 to +7, relative to the site of transcription initiation. This construct also finds use in drug screening protocols.

However, it is not intended that the present invention be limited to luciferase or GFP reporter constructs, as the art knows well other suitable reporter genes that find use with the invention. Such alternative reporter systems include, but are not limited to, for example, chloramphenicol acetyltransferase (CAT), β-galactosidase (β-gal), β-glucuronidase (GUS), and secreted alkaline phosphatase (SEAP). Such systems are common in the art, and are described in many sources (e.g., Ausubel et al. (eds.), *Current Protocols in Molecular Biology*, Chapter 9, Part II, John Wiley & Sons, Inc., New York [1994]).

2. Cells Finding Use in Methods for Drug Screening

The present invention teaches the derivation and use of primary cell cultures and established cell lines derived from tracheobronchial epithelial tissue suitable for use in drug screening protocols in conjunction with the MUC5B reporter constructs of the invention. In one embodiment, the present invention teaches the isolation and use of primary human TBE cells derived from normal or diseased human subjects (EXAMPLE 1), that find use in drug screening methods of the invention. In another embodiment, the invention teaches the use of primary mouse TBE cells isolated from transgenic mouse lines carrying a MUC5B promoter reporter construct (EXAMPLE 10). In another embodiment, the present invention teaches the use of the established HBE-1 cell line (EXAMPLE 8), which also find use in the methods of the present invention. In another embodiment, the invention teaches the use of stably transfected HBE1 cells (EXAMPLE 11).

However, it is not intended that the present invention be limited to the use of primary TBE cells, or the established HBE1 cell line, as the art knows well numerous other suitable cell cultures and cell lines that also find use with the invention. In fact, it is not intended that the present invention be limited to the use of any particular cell line(s), as many mammalian cell lines also find use with the methods for drug screening of the present invention. The only requirement of such cell lines is that the MUC5B reporter constructs of the present invention be active in these cells. Examples of other alternative cell lines falling within the scope of the present invention include, for example but not limited to, the lung-derived lines A549 mucoepidermoid carcinoma cell line, NCI-H292 carcinoma, Calu-3, and Calu-6 (lung carcinoma). Some cell lines from other organs such as HT-29 (colonic cancer) are also common in mucin research, and also find use with the methods of the invention.

3. Cell Culture Conditions Finding Use in Methods for Drug Screening

The present invention teaches various cell culture conditions suitable for use in drug screening protocols in conjunction with the MUC5B reporter constructs. In various embodiments, the present invention teaches cell culture in standard tissue culture dishes (TC), collagen-gel coated tissue culture dishes (CG), Transwell™ chambers (Corning-COSTAR, Acton, Mass.; Catalog No. 3506) (BI) and collagen gel-coated Transwell™ chambers (BICG). In a particularly preferred embodiment, the cells are grown in a biphasic, air-liquid interface, as provided in the Transwell™ chambers. In other embodiments, standard tissue culture dishes are used. Furthermore, cultures may be grown in the absence or presence of retinoic acid. Also, cells may be grown in conditions that result in elevated MUC5B gene activity. For example, in some preferred embodiments, the cells are grown in the presence of IL-6 or IL-17 cytokines, or in the presence of tobacco smoke.

However, it is not intended that the present invention be limited to any particular culture condition(s). The only requirement of the particular culture system is that the culture conditions used result in detectable levels of reporter gene activity expressed from a MUC5B reporter gene construct.

4. Cell Transfection Techniques Finding Use in Methods for Drug Screening

The present invention teaches the use of FuGENE 6™ transfection reagent (Roche Molecular Biochemicals, Indianapolis, Ind.) in the transfection of cells in the methods of the present invention, all according to the manufacturer's instructions. However, it is not intended that the present invention be limited to the use of FuGENE 6™ transfection reagent, as the art knows well numerous other suitable cell transfection methods that also find use with the invention. Such alternative methods include, but are not limited to, for example, calcium phosphate-DNA co-precipitation, DEAE-dextran mediated transfection, polybrene-mediated transfection, electroporation, microinjection, liposome fusion, lipofection, protoplast fusion, recombinant viral infection, biolistics, and proprietary methods sold by various manufacturers. Transfection reagents are available from a large number of manufacturers, including but not limited to, for example, Sigma-Aldrich (St. Louis, Mo.) and Gibco-BRL-Life Technologies (Gaithersburg, Md.). Where viral-based vectors are used, numerous recombinant viral sequences find use with the present invention, including but not limited to adenovirus sequences, adeno-associated virus sequences, retrovirus sequences, herpes virus sequences, vaccinia virus sequences and Moloney virus sequences. Mammalian cell transfection systems are common in the art, and are described in many sources (e.g., Ausubel et al. (eds.), *Current Protocols in Molecular Biology*, Chapter 9, Part I, "Transfection of DNA into Eukaryotic Cells," John Wiley & Sons, Inc., New York [1994]).

5. Stable and Transient Cell Transfection Systems Finding Use in Methods for Drug Screening The present invention teaches the use of transient and stable transfection of eukaryotic cells using FuGENE 6™ transfection reagent (Roche Molecular Biochemicals, Indianapolis, Ind.) in the methods of the present invention. In addition, the invention also teaches the use of transgenic animals, as well as cells derived from those animals, that find use in the drug screening methods of the present invention. It is not intended that the present invention be limited to any particular transfection or transgene protocol, as one familiar with the art recognizes that numerous equivalent systems all find use with the present invention. Methods for the transfection of cells and the generation of transgenic animals are common in the art, and can be found described in many sources (e.g., Ausubel et al. (eds.), *Current Protocols in Molecular Biology*, Chapter X, Part X, John Wiley & Sons, Inc., New York [1994]).

6. Transgenic Animals Finding Use in Methods for Drug Screening

The present invention teaches the use of transgenic animals finding use in the drug screening methods of the present invention. The present invention provides transgenic mice carrying MUC5B(−4,169/+7) luciferase or GFP reporter constructs. It is contemplated that such mice can be used directly to assess whether a particular compound has the ability to inhibit MUC5B expression.

In these methods, the reporter gene used in the reporter construct is not particularly limited, but in some embodiments, a luciferase or a GFP gene are used. In one embodiment, the transgenic animal carrying the MUC5B reporter construct is a mouse. In this embodiment, the transgenic animal is first treated in such a way as to induce a state of MUC5B hyperactivity, and therefor, simulate disease state. For example, it is known that mice treated with certain allergens or tobacco smoke results in a condition characterized by mucin hypersecretion, and thus, provides an animal model for human obstructive airway diseases.

Once MUC5B expression is elevated (or sufficiently detectable), the mouse is administered a candidate compound for testing. The means used to deliver the compound to the animal are not particularly limited, as oral, parenteral and inhalation delivery techniques are all contemplated. In some embodiments, oral administration of the drug is the most preferred method for drug delivery. After a period of time for treatment with the test compound, ranging for example from 1 to 30 days, the mice are sacrificed, and the level of reporter gene activity within that animal's tissues, and in particular, for example, within the airway tissues, is compared in treated versus untreated animals.

The method of measuring the reporter gene expression in the mouse tissue can be of any suitable method, as taught in EXAMPLE 10. In some embodiments, tissue-sectioning techniques are used. In some embodiments, immunohistochemical analysis is used, where an antibody or a combination of antibodies are used to detect the reporter gene product. In some embodiments, the reporter protein is measured in crude cell or tissue extracts. Compounds that are able to inhibit the expression of the MUC5B reporter gene within the transgenic animal are candidates for further development as therapeutic agents for the treatment of diseases characterized by mucin hypersecretion and airway plugging (e.g., in cystic fibrosis or bronchial pneumonia).

The following EXAMPLES are provided in order to further illustrate certain embodiments and aspects of the present invention. It is not intended that these EXAMPLES should limit the scope of any aspect of the invention

EXAMPLE 1

Tissue Collection and Cell Culture

Eleven (11) human tracheobronchial and lung tissue samples were obtained from the University of California, Davis, Medical Center or the Anatomic Gift Foundation (Laurel, Md.). All tissue procurement procedures were approved by The Human Subjects Review Committee of the University of California, Davis. Excised tissues were transported to the lab in an ice-cold, minimal essential medium (MEM; Sigma, St. Louis, Mo.). A description of the patients from which the samples were taken is shown in TABLE 1, below.

TABLE 1

| Patient No. | Age | Sex | Race | Clinic Diagnosis |
|---|---|---|---|---|
| H311 | | | | no lung disease |
| H313 | 75 | M[1] | C[2] | no lung disease, died of cardiac arrest |
| H316 | 45 | F | A | no lung disease, died of cardiac arrest |
| H317 | 50 | M | C | no lung disease |
| H297 | | | | emphysema |
| H306 | 66 | | | UIP[3] |
| H312 | 62 | M | | UIP |
| H314 | 64 | | | emphysema |
| H315 | 57 | F | C | UIP |
| H320 | 63 | M | | emphysema |
| H321 | 55 | F | | emphysema |

[1]M: male, F: female.
[2]C: Caucasian, A: African American
[3]UIP: usual interstitial pneumonitis Tissue samples from the patients listed in TABLE 1 were processed for airway epithelial cell isolation and subsequent culture using techniques known in the art. For example, this procedure is described in Wu et al., *European Respiratory Journal* 10(10):2398–2403 [1997] and Robinson and Wu., *J. Tiss. Cult. Meth.*, 13:95–102 [1991]). Briefly, human surgical or necropsy specimens were obtained and immersed in minimum essential medium (MEM; GIBOC Laboratories) with L-glutamine and without sodium pyruvate or sodium bicarbonate. The specimens were rinsed in this same medium 2 to 5 times, then immersed in a dissociation solution comprising trypsin protease and EDTA overnight at 4° C. The next day, the mucosal surface was washed multiple times with ice-cold MEM with 10% fetal bovine serum. The washes were pooled and centrifuged to isolate the suspended cells.

The primary tracheobronchial epithelial (TBE) cells contained in the cell pellet were resuspended in a growth medium and cultured in conditions to stimulate a mucoid/ciliary differentiation pathway. This complete serum-free growth medium comprised F-12 or DME/F12 (1:1) media (GIBCO Laboratories) supplemented with insulin (5 μg/ml), transferrin (5 μg/ml), epidermal growth factor (EGF; 10 ng/ml), dexamethasone (DEX; 0.1 μM), cholera toxin (20 ng/ml), bovine hypothalamus extract (BHE; 15 μg/ml), all-trans-retinoic acid (RA; 30 nM) and calcium chloride. The medium was changed the following day, and every other day thereafter. The cells were initially innoculated in plastic tissue culture dishes for propagation, and subjected to serial cultivation and passaging as necessary. In general, the primary human TBE cells maintained on plastic culture surfaces were passaged from 1 to 5 times with a total of 20 to 25 population doublings.

The cultured cells were transferred to various growth substratum and culture conditions, as necessary. In some experiments, the cell suspensions were plated onto standard 35 mm tissue culture dishes (TC), or collagen gel-coated tissue culture dishes (CG). Passage of cells that were plated onto collagen substrate was generally not performed. Some cells are further maintained in a biphasic culture chamber where the cells were maintained in an air-liquid interface. Transwell™ 25 mm chambers (Corning-COSTAR Catalog No. 3506) were used to produce the biphasic culture conditions, although other equivalent systems can also be used, for example, Millipore MILLICELL® culture plates and the Whitcutt culture method (Whitcutt et al., *In Vitro Cell. Dev. Biol.*, 24(5):420–428 [1988]). The biphasic Transwell™ culture chambers can be used without (BI), or with collagen-gel coating (BICG). The use of a biphasic culture system facilitates polarized cell growth, simulating the in vivo condition. Furthermore, confluent primary human TBE cells maintained in BICG conditions are known to express mucociliary differentiation markers (Wu et al., *European Respiratory Journal* 10(10):2398–2403 [1997]; Koo et al., *American Journal of Respiratory Cell and Molecular Biology* 20(1):43–52 [1999]; and Bernacki et al., *American Journal of Respiratory Cell and Molecular Biology* 20(4):595–604 [1999]).

Two immortalized human TBE cell lines were also used in the present studies. These were BEAS-2B subclone S, obtained from Dr. J. F. Lechner (Wayne State University, Detroit, Mich.), which was derived from SV-40 large T-antigen immortalized bronchial epithelial cells (Ke et al., *Differentiation* 38(1):60–66 [1988]) and HBE1 cells, obtained from Dr. J. Yankaskas (University of North Carolina, Chapel Hill), which are a papilloma virus immortalized tracheal epithelial cell line (Yankaskas et al., *Am. J. Physiol.*, 264:C1219–C1230 [1993]). These cell lines were maintained in serum-free Ham's F12 medium supplemented with six hormonal supplements, which were insulin (5 μg/ml), transferrin (5 μg/ml), epidermal growth factor (10 ng/ml), dexamethasone (0.1 μM), cholera toxin (20 ng/ml), and bovine hypothalamus extract (15 μg/ml). To induce mucoid/ciliary cell differentiation in these cell lines, retinoic acid (30 nM) was added to the medium, and cultures were maintained in an air-liquid interface, as in the BICG primary culture conditions described above.

EXAMPLE 2

Tissue Fixation and in situ Hybridization

In this example, the tissue samples described in EXAMPLE 1 were fixed, sectioned and probed in situ with probes specific for the MUC5B and MUC5AC transcripts. This example examines the expression of MUC5B in mature normal airway tissue, as well as in diseased airway tissue, such as in emphysema.

Experimental—Portions of the tissues described in EXAMPLE 1 were directly fixed in 4% paraformaldehyde at 4° C. overnight. The fixed tissues were washed twice using a 50% ethanol solution for 20 min each wash, followed by two additional washes with 70% ethanol. The fixed tissues were then stored in a 70% ethanol solution at 4° C. until paraffin block processing. Following paraffin block mounting, the paraffin-embedded tissues were sectioned to a thickness of 5 µm, and mounted to glass slides.

The fixed and mounted tissue sections were then analyzed by in situ hybridization, using techniques known in the art, with antisense oligonucleotide probes corresponding to the tandem repeat units of the human MUC5B and MUC5AC genes. These probe sequences used were:

MUC5B probe:
5'-TGTGGTCAGCTTTGTGAGGATCCAGGTCGTC-CCCGGAGTGGAGGAGGG-3' (SEQ ID NO: 1), and MUC5AC probe:
5'-AGGGGCAGAAGTTGTGCTCGTTGTGGGAGC-AGGGGTTGTGCTGGTTGT-3' (SEQ ID NO: 2).

These synthetic oligonucleotides (100 pmole each) were end labeled with a digoxigenin oligonucleotide tailing kit (Roche Molecular Biochemicals, Indianapolis, Ind.), according to the manufacturer's protocol. Sense oligonucleotides corresponding to these sequences were also synthesized, digoxigenin-tailed and used as a control probe for the hybridization.

In situ hybridization was carried out as per the manufacturer's protocol (Roche Molecular Biochemicals, Indianapolis, Ind.). Briefly, the glass-mounted tissue sections were digested with 10 µg/ml Proteinase K in 50 mM Tris-Cl, pH 8.0 and 50 mM EDTA for 15 min at 37° C., rinsed twice in 0.2×SSC (where 20×SSC is 3 M NaCl and 0.3 M $Na_3$citrate, pH 7.0) and then post-fixed in 4% paraformaldehyde/PBS for 20 min. Slides were treated twice for 5 min each wash with 0.1 M triethanolamine, pH 8.0, and blocked by 0.25% acetic anhydride in a 0.1 M triethanolamine (TEA) buffer. The sections were then dehydrated through the ethanol series.

The fixed glass-mounted tissue sections were then subjected to probe hybridization. Following a prehybridization, a hybridization buffer containing 2×SSC, 1× Denhard's solution, 10% dextran sulfate, 50 mM phosphate buffer (pH 7.0), 50 mM DTT, 250 µg/ml yeast tRNA, 100 µg/ml synthetic polyA DNA (Roche Molecular Biochemicals, Catalog No. 108626), 500 µg/ml salmon sperm DNA, and 0.5 pmol of digoxigenin-tagged oligonucleotide probe (MUC5B or MUC5AC) was applied to the tissue section slides. The section was hybridized at 45° C. overnight in a humidified chamber. Following hybridization, the section was washed twice with 2×SSC for 15 min each wash at 37° C., twice with 1×SSC for 15 min each wash, and twice with 0.25×SSC for 15 min each wash. After the washes, the slide was reacted with anti-digoxigenin primary antibody-alkaline phosphatase conjugate, washed and visualized according to the manufacturer's instructions (Digeoxigenin Nucleic Acid Detection Kit, Roche Molecular Biochemicals, Indianapolis, Ind.).

Alcian blue (pH 2.5)-periodic acid-Schiff (AB-PAS) staining, as used in FIG. 2, was done using methods common in the art. The alcian blue acidic reagent was first used to stain acidic mucin proteins as blue. Addition of the periodic acid-Schiff reagent stained neutral mucin proteins as red.

Results/Conclusions—Results of the in situ hybridizations and AB-PAS staining are provided in FIGS. 1–3. The panels of FIG. 1 show images of tracheobronchial tissue from a patient with no obvious airway disease or inflammation (Patient No. H316) that have been hybridized with a MUC5B probe (SEQ ID NO: 1). The images (FIGS. 1A and 1C) reveal that MUC5B message in a normal subject is mainly expressed on submucosal gland cells of the tracheobronchial tissue. The enlarged picture of the submucosal gland in FIG. 1C supports this conclusion. For surface airway epithelium, MUC5B expression was generally very low (FIG. 1A), except in some regions (FIG. 1B). No MUC5B message could be demonstrated in the distal airway and parenchyma regions (data not shown). Similar results were also observed in tissue sections from three other patients without diagnosed lung diseases (Nos. H311, H313 and H317).

Figure 3A:
FIGS. 3A–3D show light microscopy images of in situ nucleic acid hybridizations of human bronchial tissue cross sections from patients with UIP or emphysema.
Figure 3C:
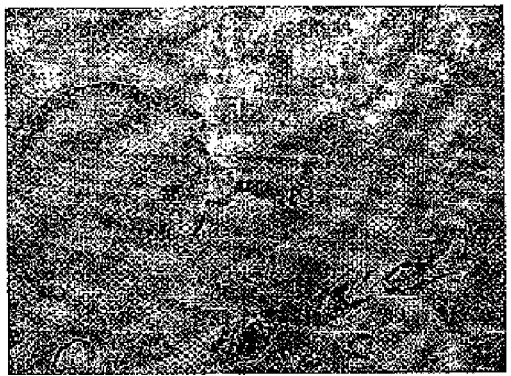
Figure 3B:
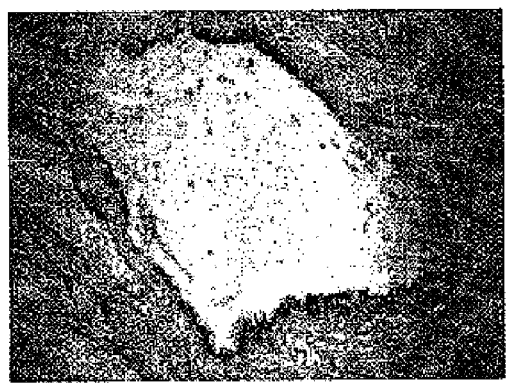

In contrast, it was observed that MUC5B message was elevated in both the surface epithelium and submucosal glands of tissue sections obtained from a usual interstitial pneumonitis (UIP) patient (No. H312; FIGS. 3A and 3B) and an emphysema patient (No. H297; FIG. 3C), respectively. In FIGS. 3A and 3C, the MUC5B message was elevated in both the surface epithelium and the submucosal gland region, in contrast to sections from the "normal" patient (see, FIG. 1). Interestingly, MUC5B message could also be seen in the surface epithelium of the bronchiole region of the UIP patient (No. H312; FIG. 3B) and emphysema patients (data not shown). Consistently, in situ hybridizations using three other emphysema patients and two other UIP patients demonstrated the same results (data not shown).

Figure 2A:
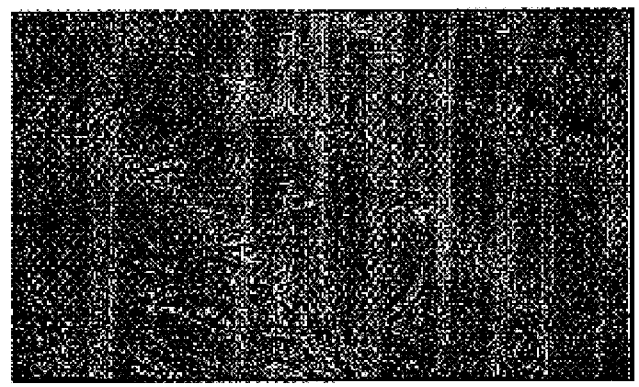
FIGS. 2A–2C show light microscopy images of normal and disease airway tissue cross sections following Alcian blue-periodic acid-Schiff (AB-PAS) staining.
Figure 2B:
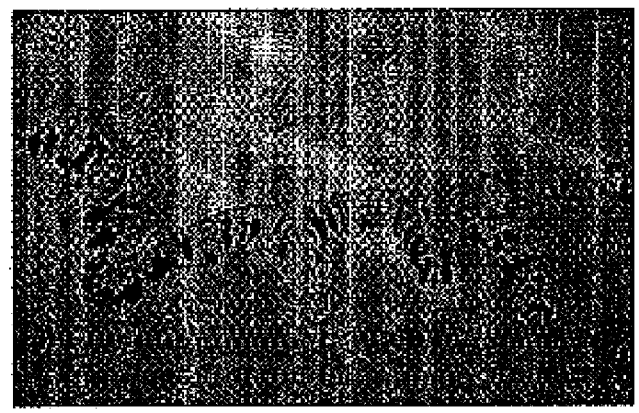
Figure 2C:
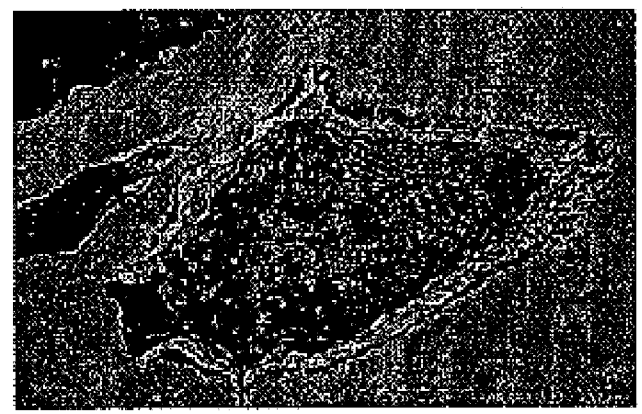

FIG. 2 shows airway tissue sections following AB-PAS staining. AB-PAS staining is a pH sensitive staining that differentiates between neutral and acidic mucosubstances (i.e., substances found on or within mucosal surfaces, cells and tissues), including glyco-conjugated proteins. Acidic mucosubstances appear blue following the staining, while neutral polysaccharides stain magenta/red. Thus, goblet cells, which produce mucin proteins and are mucin containing cells, are expected to be AB-PAS positive. In the airways of all the lung disease patients, extensive goblet cell hyperplasia (or metaplasia) in their airway epithelium (FIGS. 2B and 2C) was observed, in contrast to normal airway that had only a few goblet cells (FIG. 2A), based on AB-PAS staining and morphological analysis. The surface expression of MUC5B was limited exclusively to the goblet cells, as shown in the FIG. 3.

Figure 3D:

These results illustrate the positive correlation between the overexpression of MUC5B message by surface epithelial cells and the presence of disease in the airway region. Such an association was not seen for the expression of MUC5AC message (see, FIG. 3D). One example of such a comparative study involved seven lung tissue sections from four emphysema and three UIP patients. Representative panels are shown in FIGS. 3C and 3D. In serial tracheal tissue sections from a UIP patient, MUC5B message could be seen in both the airway surface epithelium and the submucosal glands (FIG. 3C), while MUC5AC message was seen restrictedly in the airway surface epithelium (FIG. 3D) despite an elevated expression. These observations suggest a possible role for MUC5B gene expression in airway goblet cell hyperplasia (or metaplasia), and by extension, in mucin hypersecretion.

It is known that MUC5AC expression is on the epithelial cell surface while MUC5B expression is within the mucus cells of submucosal glands. It is the novel finding of the present invention that MUC5B gene expression can be on the epithelial cell surface of patients with chronic airway disease, while in the same patients, the MUC5AC gene does not change its expression location even though its expression is also elevated.

EXAMPLE 3

RNA Isolation and Northern Blot Analysis

To further elucidate patterns of MUC5B gene regulation, the expression patterns of MUC5B in primary and established cultures of TBE-derived human cells were studied. This example describes the isolation of RNA and the analysis of MUC5B gene expression using Northern blotting techniques. This example analyzes MUC5B gene expression in various cultured cell lines derived from airway tissues, and also under various culture conditions.

Experimental—Following the establishment of primary cell cultures from the airway tissues (as described in EXAMPLE 1), the cultures were allowed to expand for 21 days following their plating on the various culture substratum. Total RNA was isolated from the 21-day cultures by a single-step acid guanidinium thiocyanate phenol-chloroform extraction method. Following similar culture conditions, total RNA was also collected from the established BEAS-2B and HBE1 cell lines.

For Northern blot hybridizations, equal amounts of total RNA (20 µg/lane) were subjected to electrophoresis on a 1.2% agarose gel in the presence of 2.2 mM formaldehyde, followed by transblotting onto Nytran® nylon membranes (Schleicher & Schuell, Keene, N.H.) and cross-linked to the membrane using a UV Stratalinker 2400 (Stratagene, La Jolla, Calif.). The membranes were prehybridized, then hybridized in a solution comprising 6×SSC, 0.5% SDS, 10 mM EDTA (pH 8.0), 0.5% disodium pyrophosphate, 5× Denhardt's solution, synthetic polyA DNA (50 µg/ml) and salmon sperm DNA (50 µg/ml). This hybridization included a single-stranded antisense 48 basepair oligonucleotide derived from the human MUC5B gene tandem repeat region (see, GenBank Accession Number X74955). The probe was end-labeled with $\gamma$-$^{32}$P-ATP by polynucleotide kinase, and had the sequence:
5'-TGTGGTCAGCTCTGTGAGGATCCAGGTCGTCCC-CGGAGTGGAGGAGGG-3' (SEQ ID NO: 3).

The blots were hybridized overnight (approximately 16 hours) at 55° C. Following hybridization, the blots were subjected to two sets of washes. The first set of washes used a wash solution comprising 2×SSC and 0.1% SDS for two washes for ten minutes each at 55° C. The second set of washes used a wash solution comprising 1×SSC and 0.1% SDS for two washes for 30 minutes each at 55° C. Following the washes, the blots were exposed to either phosphoimaging or autoradiography.

Following the above analysis for MUC5B expression, the blots were stripped, and the relative abundance of MUC5B message in the Northern blot lanes was normalized using an oligonucleotide probe specific for the human 18S ribosomal RNA (rRNA) transcript (see, GenBank Accession Number X03205).

Results/Conclusions—Northern immunoblots using a MUC5B gene probe and various RNA samples, as described above, are shown in FIGS. 4A and 4B. RNA was isolated from primary TBE cells that were alternatively plated on standard 35 mm tissue culture dishes (TC), collagen-gel coated tissue culture dishes (CG), 25 mm Transwell™ chambers (Corning-COSTAR Catalog Number 3506) (BI) or in collagen gel-coated Transwell™ chambers (BICG). The total RNA isolated from these cells was analyzed in the Northern blot, as describe above, and which is shown in FIG. 4A. From FIG. 4A, it can be seen that primary human TBE cells derived from a "normal" patient expressed detectable levels of MUC5B message when cultured in the presence of retinoic acid. The levels of MUC5B message in TC and CG cultures were very low compared to the BI and BICG culture conditions, and appeared unaffected by retinoic acid. However, the levels of MUC5B message in BI and BICG cultures were greatly enhanced by the presence of retinoic acid, and furthermore, were induced to a level far in excess of the expression observed in the TC and CG culture conditions. This observation is consistent with previous studies (Koo et al., *American Journal of Respiratory Cell and Molecular Biology* 20(1):43–52 [1999] and Wu et al., *European Respiratory Journal* 10(10):2398–2403 [1997]). Thus, MUC5B message in culture was affected not only by RA, but also by the culture condition with an order of most-to-least responsive of BICG>BI>>CG>TC. The results of this Northern blot were identical when RNA from cell cultures derived from 11 diseased human tissues were used in place of the TBE cells derived from a normal subject (data not shown).

Expression of the MUC5B gene was also studied in two commonly used human TBE immortalized cell lines (HBE1 and BEAS-2B). These cultures were maintained under the BICG culture condition and were maintained in the presence of retinoic acid. Similar to the primary TBE cells, the HBE1 cell line also showed strong MUC5B expression, although slightly lower than the TBE culture (see, FIG. 4B). For the BEAS-2B subclone S cell line, MUC5B expression was undetectable in the Northern blot under all four culture conditions as described above (FIG. 4B, and data not shown).

EXAMPLE 4

Isolation and Characterization of a MUC5B Genomic Clone

This Example describes the isolation of a MUC5B genomic clone, and also describes the characterization of the clone, including restriction mapping, sequencing and sequence annotation. The isolated genomic clone comprises 22.7 kB of genomic chromosome 11 sequence. This 22.7 kB sequence includes both MUC5AC and 5' MUC5B coding sequences, from which it is inferred that the clone must also contain the entirety of the MUC5B 5' promoter regulatory region.

Isolation of a MUC5B Genomic Clone—A DNA probe derived from MUC2 amino-terminal and promoter proximal region sequences was used to screen a genomic cosmid library derived from human placenta (CLONTECH). The probe used in this screening (SEQ ID NO: 4) corresponded to nucleotide positions 7,081 thru 11,260 of the human MUC2 genomic sequence provided in GenBank Accession Number U67167. The nucleic acid probe was radiolabeled using Ready-To-Go™ DNA Labeling Beads (Amersham-Pharmacia Biotech, Catalog Number 27–9240–01). The library screening used a bacterial colony lift assay, as widely known in the art, using low stringency hybridization conditions. Bacterial colonies containing library clones were transferred to Nytran® nylon membranes (Schleicher &

Schuell, Keene, N.H.). These membranes were prehybridized, then hybridized with the radiolabelled probe in a solution comprising 6×SSC, 0.5% SDS, 10 mM EDTA (pH 8.0), 0.5% disodium pyrophosphate, 5× Denhardt's solution, synthetic polyA DNA (50 µg/ml) and salmon sperm DNA (50 µg/ml). The membranes were hybridized overnight (approximately 16 hours) at 55° C.

Following hybridization, the blots were subjected to two sets of washes. The first set of washes used a wash solution comprising 2×SSC and 0.1% SDS for two washes for ten minutes each at 55° C. The second set of washes used a wash solution comprising 1×SSC and 0.1% SDS for two washes for 30 minutes each at 55° C. Following the washes, the blots were exposed to either phosphoimaging or autoradiography, and positive clones were identified.

In view of the amino acid conservation in the 5' end (i.e., amino-terminus) cysteine-rich domains between MUC2 and MUC5B, it was contemplated that this approach would identify genomic clones containing the amino-terminal and promoter region of the human MUC5B gene. A total of $10^6$ cosmid clones were screened, of which eight were positive for hybridization to the MUC2 probe.

These eight positive cosmids were subsequently subjected to confirmation in a secondary screen using a Southern blot hybridization with a MUC5AC cDNA probe under stringent hybridization conditions. The probe used in this screening step was derived from the 3' end of the MUC5AC gene, and corresponds to nucleotide positions 1,441 through 3,108 of GenBank Accession Number Z48314. The hybridization conditions used in the screening were, specifically, 6×SSC, 0.5% SDS, 10 mM EDTA (pH 8.0), 0.5% disodium pyrophosphate, 5× Denhardt's solution, synthetic polyA DNA (50 µg/ml) and salmon sperm DNA (50 µg/ml). The blots were hybridized overnight (approximately 16 hours) at 55° C.

Following hybridization, the blots were subjected to three sets of washes. The first set of washes used a wash solution comprising 2×SSC and 0.1% SDS for two washes for ten minutes each at 65° C. The second set of washes used a wash solution comprising 1×SSC and 0.1% SDS for two washes for 30 minutes each at 65° C. The third set of washes used a wash solution comprising 0.1×SSC and 0.1% SDS for two washes for 30 minutes each at 65° C. Following the washes, the blots were exposed to autoradiography, and positive clones were identified.

The MUC5AC probe was used in this analysis in view of the genetic map of chromosome 11p15.5. That chromosome is suggested to contain a cluster of mucin genes having the order: centromere-MUC6-MUC2-MUC5AC-MUC5B. The MUC2, MUC5AC and MUC5B genes all lie on the same strand and are transcribed in the same orientation.

Thus, a genomic clone containing MUC5AC exon sequences, as well as sequences homologous to the MUC2 promoter-proximal region, may contain sequences from the MUC5B promoter region (see, Pigny et al., *Genomics* 38(3):340–352 [1996]; Velcich et al., *Jour. Biol. Chem.*, 272(12):7968–7976 [1997]; Meerzaman et al., *Jour. Biol. Chem.*, 269(17):12932–12939 [1994]; and Desseyn et al., *Jour. Biol. Chem.*, 272(6):3168–3178 [1997]).

Of the eight positive clones identified in the primary screen, only one of those (a single cosmid clone termed Cos-1) was positive in the secondary screening. Sequence analysis of this clone started with the T3 and T7 primer ends of the cosmid backbone to reveal the DNA sequence of both ends of the cloned genomic insert. This sequencing revealed the presence of the 3' end of the MUC5AC cDNA and the 5' end of the large central exon of MUC5B, respectively. Thus, knowing the gene order 5'-MUC5AC-MUC5B-3', the Cos-1 clone should contain genomic DNA that spans the region between the 3' end of MUC5AC gene and the 5' end of MUC5B coding sequences, and therefor, must also contain the entirety of the MUC5B promoter 5' regulatory sequences. The organization of this positive clone is depicted in FIG. 5A. The full length of the genomic DNA insert on Cos-1 is estimated to be approximately 44 kB, as estimated by restriction mapping. An expanded view of the promoter proximal region and the MUC5B exon/intron structure of this region is depicted in FIG. 5B.

Restriction Mapping of the MUC5B Cosmid—Genomic DNA from the Cos-1 cosmid was prepared and digested with Kpnl and EcoRl restriction enzymes. Southern blotting hybridization was carried out to determine which DNA fragments contain MUC5AC gene sequences or MtJC5B cDNA sequences. The probe corresponding to th 3' end of the MUC5AC message is provided in SEQ ID NO: 5 (corresponding to nucleotide positions 1,441 through 3,108 of GenBank Accession Number Z48314). The probe corresponding to the 5' end of MUC5B large central exon is provided in SEQ ID NO: 34 (corresponding to nucleotide positions 1 through 809 of GenBank Accession Number Z72496).

Figure 9:
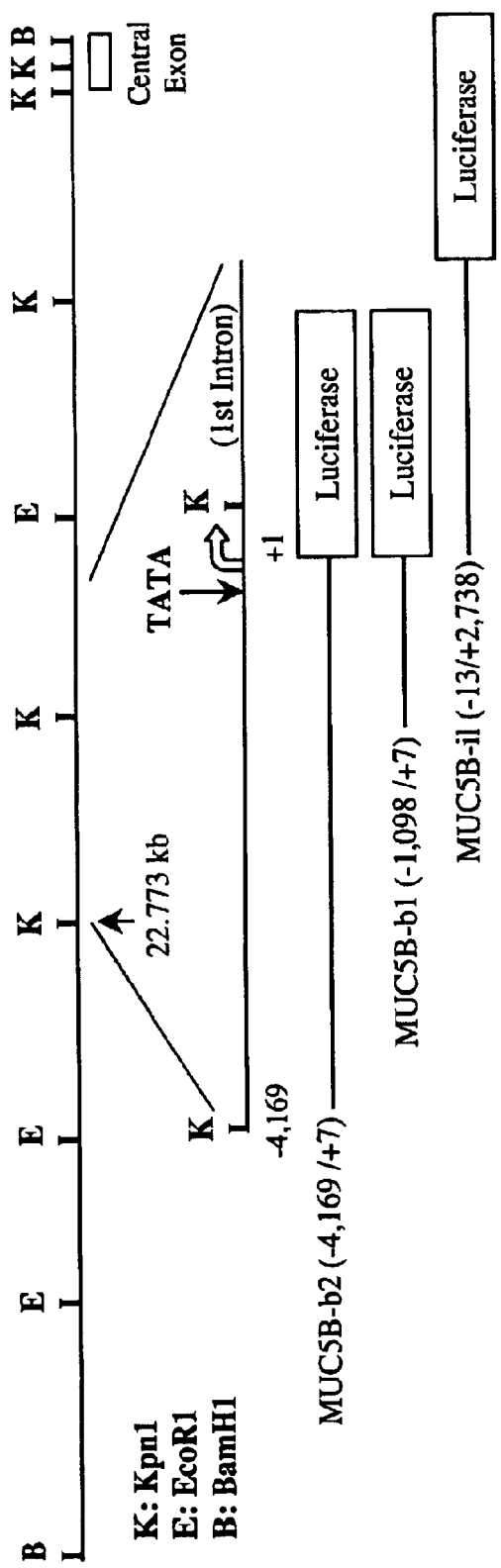
FIG. 9 shows a schematic of the chimeric promoter-reporter gene constructs made using the isolated MUC5B gene sequences. The chimeric constructs are termed MUC5B-b1, MUC5B-b2, and MUC5B-i1. Each construct contains the luciferase reporter gene and various extents of MUC5B promoter-proximal sequences.

DNA fragments that hybridized to the MUC5B cDNA probe were isolated and further subcloned by various restriction enzyme digestions into pGem 4Z (Promega, Madison, Wis.). These subclones were further mapped by restriction enzyme digestion and sequenced. A restriction map of this region is shown in FIG. 9.

Genomic DNA Sequencing—Human genomic DNA in the Cos-1 clone was sequenced using an ABI Prism Model 377 Automated DNA sequencer (Applied Biosystems, Foster City, Calif.). Various primers corresponding to different regions of the Cos-1 cosmid clone were used in the sequencing. The sequencing data was analyzed and aligned using LaserGene software (DNASTAR, Madison, Wis.). The genomic sequencing data was used to verify the restriction map and also to establish the exon/intron gene structure. MUC5B genomic sequence comprising 22,773 base pairs upstream of the large central exon was generated and submitted to GenBank with the Accession Number AF107890. This 22.7 kB includes all exons/intons upstream of the large central exon, as well as 5' regulatory sequences upstream of the transcription start site. This 22.7 kB sequence is shown in SEQ ID NO. 6, and FIG. 6. This sequence includes 4169 nucleotides upstream of the predicted transcription start site (see EXAMPLES 5 and 6, and FIG. 7), as well as 18,604 nucleotides encompassing the 5'-untranslated (5'-UT) region and exon/intron structure from the 5' terminal half of the gene through exon 31 (also termed the large central exon).

Sequence Analysis and Annotation—Among the 22,773 base pairs sequenced, the 5'-most distal 4,169 base pairs correspond to the 5'-flanking region (i.e., the promoter sequence) of MUC5B. In addition to the identification of the MUC5B transcription start site (see, EXAMPLES 5 and 6), other landmarks are also noted in this genomic sequence. Analysis of the sequence revealed the presence of a TATA box 30 nucleotides upstream of the transcription start site and a putative translation start codon ATG embedded within a Kozak consensus sequence. Furthermore, based on the deduced amino acid sequence, the amino terminal peptide contained a classic putative secretory signal sequence (see, FIG. 8). This feature is consistent with the secretory nature of the mucin gene products in the airway and various other organs.

Several putative motifs for various transcription factor binding sites were also identified upstream of the transcription start site, including binding motifs for c-Myc at −101, Ap-2 at −1,155, Hoxd9/10 at −1,189, and GRE at. −1,978. In addition, there are two putative motifs for binding of NF-κB (at −237 and −371) and AP1 (at −497 and −2,000) (see, FIG. 8).

EXAMPLE 5

Determination of the MUC5B Transcription Start Site by Primer Extension Analysis This example describes the identification of the MUC5B transcription start site using a primer extension methodology.

Experimental—A primer extension method was used to map the start site(s) of the MUC5B transcription unit. In this primer extension protocol, 50 μg of total RNA was reverse-transcribed using a $^{32}$P end-labeled oligonucleotide primer termed Pel1 having the sequence GCGGCACCACGAGCATGGC (SEQ ID NO. 7, and see TABLE 2). This primer lies at nucleotide position +123/+105 according to the numbering convention of FIG. 8. The radiolabeled reverse-transcribed products were analyzed on a 6% polyacrylamide gel simultaneously with a corresponding Sanger (i.e., di-deoxy) sequencing series (which used the same Pel1 primer and pcDNA3 vector template) along with DNA size reference markers (pBR322 DNA digested by MspI, New England Biolabs, Inc., Beverly, Mass.).

Results/Conclusions—Due to the large size of the human MUC5B message (Desseyn et al., *Jour. Biol. Chem.*, 273 (46):30157–30164 [1998]), the integrity of the isolated MUC5B mRNA is difficult to maintain, thus, the primer extension signal is likely to be weak or degraded. The results of the primer extension analysis are shown in FIG. 7. This denaturing PAGE gel contains a Sanger dideoxynucleotide sequencing ladder (in the order GATC) in lanes 3–6 generated using the fmol® DNA Cycle Sequencing System (Promega Corporation, Catalog Number Q4100), and also contains radio-labeled DNA size markers indicated on the right. The primer extension reactions are shown in lanes 1 and 2, where lane 1 used RNA template isolated from human trachea tissue, and lane 2 used RNA isolated from human primary tracheobronchial epithelial (TBE) cells. As can be seen in lanes 1 and 2, the primer extension reactions showed the transcription start site to be located approximately at basepair position 4176, as shown in FIG. 6, and GenBank Accession No. AF107890 (see, FIG. 8). Significant degradation and weak signal are observed (FIG. 7).

TABLE 2

| Method | Primer sequence | Orientation | Position | SEQ ID NO. |
|---|---|---|---|---|
| 5' RACE | GCGGT GCCCA TTGTA CCAGC | antisense | +4106/+4087 | 8 |
| | TGGAC CAGCG GCAGA CCTCG | nested antisense | +4086/+4067 | 9 |
| | CAGTC ACCAT GCAGG TCGTAGA | antisense | +1402/+1381 | 10 |
| | TCATA GGTGG AGATG TGGGC | nested antisense | +1372/+1353 | 11 |
| | GTGGA AGGGC TTGGG GGTTG ATGAT | antisense | +1997/+1973 | 12 |
| | GAGAA GGCAC TGTTG GGATC GG | nested antisense | +1960/+1939 | 13 |
| | TGGGC ATAGA ACTCG TTGAA GG | antisense | +724/+703 | 14 |
| | GTTGA AGTCC CCACA CAGGC | nested antisense | +692/+673 | 15 |
| | GGTCT GGTTG GCGTA TTTGG | nested antisense | +668/+649 | 16 |
| | CTGGG GAAGA CAGTG ACGGG T | antisense | +250/+230 | 17 |
| | CGGGT GGAAC AAAGC TCACG C | nested antisense | +234/+214 | 18 |
| | CTGTG GAGCC GAGCT GGGGG A | nested antisense | +162/+142 | 19 |
| oligo d(T) anchor primer | GACCACGCGTATCGATGTCGACTTTTTT TTTTTTTTTTV | sense | | 20 |
| oligo d(A) anchor primer | GACCACGCGTATCGATGTCGACAAAAA AAAAAAAAAAV | sense | | 21 |
| RT-PCR | GTGGA AGGGC TTGGG GTTGA TGAT | antisense | +1997/+1974 | 22 |
| | GAGAA GGCAC TGTTG GGATC GG | nested antisense | +1960/+1939 | 23 |
| | GGGCC CACAT CTCCA CCTAT | sense | +1351/+1370 | 24 |
| Primer Extension | GCGGCACCACGAGCATGGC (Pell Primer) | antisense | +123/+105 | 7 |
| Promoter Constructs | | | | |
| MUC5B-b1 | AAGGATCCGGGTGCTTGCTCCCCTGG[1] | antisense (PL1) | +7/−13 | 25 |
| | AAGCTAGCGCCACGGAGCATTCAGG | sense (PU2) | −1098/−1080 | 26 |
| MUC5B-b2 | AAGGATCCGGGTGCTTGCTCCCCTGG | antisense (PL1) | +7/−13 | 27 |
| | AAGCTAGCCTGGTTGTGCCTGTCGCTCA | sense (PU1) | −4169/−4149 | 28 |
| MUC5B-i1 | AAAGATCTCCAAATTCCAGCCCCTCCAG | antisense (PiL1) | +2738/+2719 | 29 |
| | AAGCTAGCCAGGGGAGCAAGCACCC | sense (PiU1) | −13/+5 | 30 |

Underlined nucleotides are added to the 5'-end of oligonucleotide primers to facilitate cloning. These cloning sites are NheI (GCTAGC), BglII (AGATCT), and BamHI (GGATCC), and each is preceded by two "A" residues. V means A or G or C but not T.

43

EXAMPLE 6

MUC5B Transcription Start Site Mapping Using a Modified 5'-RACE Protocol

This example describes refined mapping of the start site of the MUC5B transcription unit. To overcome the limitations of the primer extension mRNA mapping method of EXAMPLE 5, a modified 5'-rapid amplification of cDNA ends (5'-RACE) method was developed, and is described in the present example.

Experimental—A modified 5'-RACE method was developed to determine the MUC5B transcription start site. A 5'-RACE kit (Roche Molecular Biochemicals, Indianapolis, Ind.) containing a reverse transcriptase was used to synthesize the first-strand cDNA from total RNA (3 µg) isolated from human tracheobronchial tissues or cultures of primary human TBE cells that had been cultured using air-liquid interface culture conditions for at least 21 days. An antisense primer at nucleotide position +250/+230 having the sequence CTGGGGAAGACAGTGACGGGT (SEQ ID NO. 17, and TABLE 2) was used to initiate first-strand cDNA synthesis.

In the RACE reactions, only a portion of the 5'-most sequence of the transcript is known. Based on that information, a new primer is designed to generate additional PCR products. After tailing, the resulting double stranded cDNA products were used in polymerase chain reactions (PCR) with nested primers within the 3'-end and the 5'-anchor oligo d(T) adapter. These new products are then cloned and sequenced. Still additional primers are designed based on the new sequence, until the 5' terminus of the message is reached. Since every RACE 5' end product is poly-A tailed, if the message start site is A, it will not be detected in the sequencing reactions. To circumvent this problem, the 5' end of the final RACE product was tailed with oligo d(T) by terminal deoxynucleotidyl transferase, instead of 3' tailing with oligo d(A), so that the true start site can be detected. PCR amplification was carried out using the following primers (also see TABLE 2):

sense oligo d(A) 5' primer:
GACCACGCGTATCGATGTCGA-CAAAAAAAAAAAAAAAAV (SEQ ID NO. 21)

sense oligo d(T) 5' primer:
GACCACGCGTATCGATGTC-GACTTTTTTTTTTTTTV (SEQ ID NO. 20)

antisense 3' primer +234/+214:
CGGGTGGAACAAAGCTCACGC (SEQ ID NO. 18)

antisense 3' primer +162/+142:
CTGTGGAGCCGAGCTGGGGA (SEQ ID NO. 19)

The resulting PCR products were subcloned into the TA Cloning® vector (Invitrogen, Carlsbad, Calif.) and sequenced. Since there should be only one common DNA sequence adjacent to oligo d(T) and oligo d(A) adapters, this DNA sequence should be identical to that of the 5'-end message upstream to the +250/+230 primer. A major advantage of this approach is the use of PCR, which allows the amplification of the 5'-ends of low abundance messages.

Results/Conclusions—The sequence analysis of the PCR products generated above identified a transcription start site located at approximately basepair position 4176, as shown in FIG. 6, and GenBank Accession No. AF107890 (see, FIG. 8). This position is in agreement with the primer extension analysis described in EXAMPLE 5, and shown in FIG. 7. Both approaches yielded the same conclusion, suggesting that the transcription start site is 18604 basepairs upstream of the large central exon (using the numbering convention of FIG. 8). This putative transcription start site is different from the sites previously reported (Offner et al., Biochem. Biophys. Res. Comm., 251(1):350–355 [1998]; and Van Seuningen et al., Biochemical Jour., 348 Pt 3(12):675–686 [2000]).

EXAMPLE 7

Construction of Chimeric MUC5B Promoter Reporter Constructs

This example describes the construction of luciferase reporter constructs under the transcriptional control of MUC5B gene sequences. Three constructs are described that contain various portions of the MUC5B gene promoter region. The gene sequences used to make these reporter constructs were derived from the isolated genomic DNA described in EXAMPLE 4. Assessment of the activity of these constructs is described in EXAMPLE 8.

Fragments of the human MUC5B gene corresponding to different 5'-flanking regions as well as a region downstream of the transcription start site and including exon 1 were PCR amplified using appropriate primer pairs (see, TABLE 2 for complete primer sequences). Total RNA isolated from primary TBE cells grown in an air-liquid interface in a collagen gel in the presence of retinoic acid served as the template for these PCR reactions. The PCR products were digested with appropriate restriction enzymes and subcloned into the promoterless pGL-3 basic vector (Promega, Madison, Wis.), which contains the luciferase gene open reading frame. Thus, the luciferase gene is under the transcriptional control of the subcloned nucleic acid upstream of the luciferase open reading frame. Clones of these chimeric constructs were verified by DNA sequencing. Three constructs were made, as shown in TABLE 3.

TABLE 3

| Construct | Nucleotide Positions | PCR Primer Pairs | Subcloning Sites |
|---|---|---|---|
| MUC5B-b1 | −1098 to +7 (SEQ ID NO: 31 and FIG. 10) | PL1 (antisense) SEQ ID NO: 25 PU2 (sense) SEQ ID NO: 26 | NheI/BamHI |
| MUC5B-b2 | −4169 to +7 (SEQ ID NO: 32 and FIG. 11) | PL1 (antisense) SEQ ID NO: 27 PU1 (sense) SEQ ID NO: 28 | NheI/BamHI |
| MUC5B-i1 | −13 to +2738 (SEQ ID NO: 33 and FIG. 12) | PiL1 (antisense) SEQ ID NO: 29 PiU1 (sense) SEQ ID NO: 30 | NheI/BglII |

In addition to the luciferase reporter constructs described above, a MUC5B promoter reporter construct encoding a green fluorescent protein (GFP) reporter gene was also constructed. To make this construct, the −4169 to +7 MUC5B promoter region was subcloned into a vector backbone (Promega Corporation, Madison, Wis.) carrying the GFP open reading frame, such that transcription of the open reading frame is under the transcriptional control of the MUC5B sequences.

EXAMPLE 8

Transient Transfections and Assessment of Reporter Construct Activity

This example describes the transient transfection of the MUC5B luciferase reporter constructs (i.e., the constructs described in EXAMPLE 7), and the subsequent analysis of their activity in the context of various cell lines and cell culture conditions. This analysis was conducted in primary TBE cells as well as established TBE cell lines, and also in response to various culture conditions.

Experimental—For transient transfection studies, primary TBE cells were cultured in 35 mm dishes and grown to 60–80% confluence. The chimeric reporter plasmids used in the transfections were purified using QIAGEN® plasmid isolation kits, and the transient transfections were done using Roche FuGENE 6™ transfection reagent (Roche Molecular Biochemicals, Indianapolis, Ind.) according to the manufacturer's instructions. In these transfections, 0.5 μg of MUC5B-luciferase reporter plasmid DNA per 35 mm culture dish was used for each transfection. In addition, 0.5 μg of the pSV-β-gal expression vector was also included in each transfection for the normalization of transfection efficiency between dishes. Following the transfection, cells were cultured for an additional 48 to 72 hours, then harvested.

Cell extracts were prepared by removing the culture media from the various culture dishes, washing the cells with PBS solution, adding 200 μl of lysis buffer (0.5 M HEPES pH 7.5, 5% Triton-N101, 1 mM $CaCl_2$ and 1 mM $MgCl_2$) directly to each 35 mm dish, incubating and mechanically scraping and removing the contents of the dish. Luciferase reporter gene activity was quantitated using the LucLite™ luciferase reporter assay system (Packard Bioscience/Packard Instrument Company, Meriden, Conn.) according to the manufacturer's instructions, using a Packard LumiCount™ luminometer (Packard Instruments, Meriden, Conn.).

The β-galactosidase reporter gene activity was assayed according to methods known in the art. Briefly, the luciferase cell extracts described above were mixed with an equal volume of β-galactosidase assay buffer (120 mM $Na_2HPO_4$, 80 mM $NaH_2PO_4$, 2 mM $MgCl_2$, 100 mM β-mercaptoethanol, 1.33 mg/ml o-nitrophenyl-beta-D-galactopyranoside [ONPG]), then read in a microplate reader (Molecular Devices) at wavelength 420 nm.

For studying the effects of culture conditions on the promoter-reporter gene activity, primary human TBE cultures were grown in 60 mm dishes and transfected with 1 μg of MUC5B promoter-luciferase construct DNA and 0.5 μg pSV-β-gal expression vector. One day following the transfection, cultures were passaged into either 35 mm tissue culture dishes or into collagen gel-coated 25 mm Transwell™ chambers (Coming-COSTAR Catalog Number 3506). Additionally, the cultures were maintained either in the absence or presence of supplemental all-trans-retinoic acid (30 nM). For Transwell™ cultures, chambers were maintained in an air-liquid interface for an additional three days. Cell extracts were prepared and luciferase and β-galactosidase activities were analyzed as described above.

For each transfection, relative luciferase activity was expressed after normalization for β-galactosidase activity. The results are presented as a mean of relative activities from at least triplicate dishes, and data is collected from at least three independent experiments. Activity is expressed as units of luciferase activity per unit of β-gal activity (units/beta-gal).

Results/Conclusions—To determine whether the 5' subdomains cloned in EXAMPLE 7 (SEQ ID NOS: 31, 32 and 33, and see FIGS. 10–12) contain cis-elements sufficient for the initiation or regulation of MUC5B transcription, the luciferase reporter constructs were used in transient transfection assays, as described above. The MUC5B-b1 and MUC5B-b2 constructs comprise various extents of MUC5B sequence upstream of the predicted transcription start site. These two constructs contain sequences –1098 to +7 (SEQ ID NO: 31) and –4169 to +7 (SEQ ID NO: 32), respectively. In addition, the third construct, MUC5B-il, comprises sequences –13 to +2738 (SEQ ID NO: 33). This construct was made to test whether these downstream sequences contain elements capable of promoting transcription initiation of the MUC5B gene, as proposed in previously published reports (Desseyn et al., *Jour. Biol. Chem.*, 273(46):30157–30164 [1998]; and Van Seuningen et al., *Biochemical Jour.*, 348 Pt 3(12):675–686 [2000]).

FIG. 13 shows the results of a transfection assay using the chimeric reporter constructs shown in FIG. 9 and passage-1 primary TBE cells. The TBE cells were also co-transfected with a β-galactosidase expression vector, and luciferase activity was normalized against β-galactosidase activity to take into account transfection efficiency variability. Relative activities of each of the reporter constructs following transfection in the TBE cells is shown, and activity is expressed as units of luciferase activity per unit of β-gal activity (units/beta-gal). As can be seen in this FIG. 13, the reporter gene activity in MUC5B-b1 and MUC5B-b2 transfected cells was two- to five-fold higher, respectively, than those transfected with the promoterless control construct, pGL-3 (labeled "control"). However, no significant activity was observed in the transfection using the MUC5B-il construct. These results indicate that the regions –1098 to +7 and –4169 to +7 both have promoter activity, and the –4169 to +7 region contains stronger promoter activity than does the –1098 to +7 region. Furthermore, the –13 to +2738 region contained no detectable promoter activity under these conditions.

Based on the above study, the MUC5B-b2 construct was further used to characterize the specificity of the promoter activity. The result of this experiment are shown in FIG. 14. The MUB5B-b2 construct and the pGL3 control construct were transfected into three different cell types, which were passage-1 TBE cells (unfilled bars), HBE1 cells (striped bars) and BEAS-2B (S clone) cells (black bars). As can be seen in FIG. 14, the MUC5B-b2 promoter was most active in the primary TBE cells, followed by activity observed in the HBE1 cells. No significant promoter activity was observed in the BEAS-2B cells. These results are consistent with the Northern blot data (FIG. 4), which suggests cell type-specific gene expression of the MUC5B gene.

In another experiment, as shown in FIG. 15, the effect of cell culture conditions on MUC5B-b2 promoter activity in primary human TBE cells was tested. The TBE cells were maintained in either standard tissue culture dishes (TC) or collagen gel-coated Transwell™ chambers (BICG), and activity of the MUC5B-b2 reporter construct was observed in these cultures. Furthermore, the cultures were maintained either in the presence or absence of retinoic acid (RA). The luciferase reporter gene activity in each transfected culture was normalized to the activity of a cotransfected β-galactosidase expression vector. Results are expressed as "fold increase" of luciferase activity, comparing RA-treated and RA-untreated cultures, where the activity of the RA untreated culture is set to 1. The activity of the MUC5B-b2 reporter in RA-untreated culture in the TC conditions was normalized to 1. Transfections were done in triplicate, and the mean results of two independent experiments are shown.

As shown in FIG. 15, when transfected cells were plated on tissue culture dishes, the reporter gene activity was not affected by RA. In contrast, the reporter gene activity was elevated five-fold by RA treatment when transfected cells were maintained under BICG conditions. This culture condition-dependent, RA-stimulated promoter activity was consistent with the Northern blot data, which showed that culture conditions influenced RA-dependent MUC5B gene expression.

EXAMPLE 9

Construction of Non-Human Transgenic Animals

This example describes the construction of transgenic mice carrying luciferase and green fluorescent protein (GFP) reporter constructs driven by the MUC5B promoter genomic region −4169 to +7. These constructs are described in EXAMPLE 7. The transgenic mice were made using techniques well known in the art. Briefly, construction followed the following steps:

Egg Production for Injections

To obtain a large quantity of eggs (>250) for injection, sexually immature FVB/N females (4–5 weeks of age) were superovulated by using consecutive pregnant mare serum gonadotropin (PMS) and human chorionic gonadotropin (HCG) hormone injections. Females were mated to stud males immediately following the HCG injection.

Harvesting Eggs

Eggs were harvested the next day from the ampulla of the oviduct of the mated females. Eggs were treated with hyaluronidase to remove nurse cells, and were then washed through several dishes of M2 media. Fertilized eggs are then stored in M16 media at 37° C. and in 5% $CO_2$ until injection.

Injection of Eggs

Approximately 30–50 eggs were removed from the incubator at a time for injection. Under high magnification, each egg is individually injected with a MUC5B promoter reporter transgene (either a MUC5B-luciferase reporter or a MUC5B-GFP reporter). After each egg in that group was injected, all eggs were returned to the incubator. This procedure was repeated until all eggs were injected. At the end of the injection period, eggs which did not survive injection were removed from each group.

Implanting the Eggs

Injected eggs were then implanted in groups of 10–15 bilaterally into the oviduct of pseudopregnant females (females which were mated to vasectomized males). The animals were allowed to recover from anaesthesia on a warming plate, and then returned to the animal room. Animals were kept under sterile conditions throughout their pregnancy, and the implanted mothers were brought to term.

Selection of Transgenic Progeny

Progeny of the implanted mothers were analyzed for the presence of transgene sequences using a combination of PCR and Southern blotting techniques with tail DNA. Mice demonstrating germ line transmission of transgene sequences were identified. The transgenic mice were maintained as heterozygotes. Multiple lines of mice that stably inherit MUC5B-luciferase and MUC5B-GFP transgene sequences were identified and independently maintained.

EXAMPLE 10

Analysis of MUC5B Reporter Constructs in Transgenic Animals

This example describes the analysis of MUC5B promoter reporter constructs carried as integrated transgenes in mice. The construction of these mice is described in EXAMPLE 9. The expression of these reporter genes is analyzed using two different protocols (i.e., one for luciferase activity analysis, and one for GFP analysis). Furthermore, the activity of these reporters is studied in response to various cytokines and environmental factors, such as interleukin-6 (IL-6), IL-17 and tobacco smoke.

A. Analysis of Reporter Gene Activity in Primary TBE Cultures Derived from Transgenic Mice The transgenic mice described in EXAMPLE 9 were used to isolate TBE cells, which were maintained in culture. The TBE cells were maintained in three culture conditions, which were control (no supplement), with interleukin-6 (IL-6) at a concentration of 10 ng/ml or with IL-17 at a concentration of 10 ng/ml. The cells were maintained in the presence of the cytokines for 7 days, harvested and cell extracts were prepared as described in EXAMPLE 8. The luciferase activity in each cell extract was determined, and normalized for total protein concentration of the extract samples.

FIG. 16 shows the results of this analysis of the MUC5B-b2 luciferase reporter activity. As can be seen in the Figure, the addition of the pro-inflammatory cytokines IL-6 or IL-17 to the cell cultures resulted in significant upregulation of the MUC5B promoter activity. It is contemplated that this situation mimics the in vivo situation, where IL-6 and IL-17 expression are frequently observed in conjunction with infection and other diseases associated with mucin hyper-expression. Thus, it is possible that IL-6 or IL-17 is responsible for the elevated MUC5B expression seen in various airway disease states.

B. Analysis of Reporter Gene Activity in Tissues Derived from Transgenic Mice

Alternatively, and in a manner similar to that described above, reporter gene activity can be analyzed in cultured cells isolated from any particular tissue from the transgenic animal. For example, it is contemplated that cultured colon tissue epithelial cells can also be used in a manner as described in this EXAMPLE, as colon tissue has been demonstrated to produce mucin proteins in vivo, and is also a suitable system for the study of MUC5B gene regulation.

In another alternative protocol, analysis of reporter gene activity in cells of a particular tissue isolated from the transgenic animal can be done directly by generating protein extracts from tissues isolated from the transgenic animals. Samples of these tissue extracts can be analyzed for the presence of reporter gene, for example, using the same luciferase assay as described in EXAMPLE 8. In a related protocol, the presence of GFP can also be quantitated in a crude protein extract using a suitable scintillation fluid (e.g., FloroCount, Packard Bioscience) and a fluorescence excitation detection apparatus.

C. Analysis of Reporter Gene Activity in Tissue Sections Derived from GFP-Reporter Transgenic Mice In another alternative protocol, GFP reporter gene activity in the cells of any particular tissue isolated from a transgenic animal carrying a MUC5B-GFP reporter construct can be assessed by fluorescence microscopy. For example, tissues can be isolated from a transgenic mouse carrying the MUC5B-GFP reporter construct, and this tissue is sectioned and mounted to glass slides. These sections are then observed under a suitable excitation fluorescence microscope, and the GFP protein can be visualized.

D. Analysis of Reporter Gene Activity in Tissue Sections Derived from Transgenic Mice Using Immunohistochemistry In another alternative protocol, reporter gene activity in the cells of any particular tissue isolated from a transgenic animal carrying a MUC5B promoter reporter construct can be analyzed by immunohistochemistry using a primary antibody to the particular reporter gene product encoded by the transgene. For example, anti-GFP and anti-luciferase antibodies are commercially available (see, e.g., Goat Anti-Luciferase Polyclonal Antibody, Promega Corporation, Catalog No. G7451). The bound primary antibody can then be detected using a suitable secondary antibody (e.g., Donkey Anti-Goat IgG Alkaline Phosphatase Conjugate, Promega Corporation, Catalog No. V1151), and thus, expression of the reporter gene in the tissue sections can be visualized.

EXAMPLE 11

Construction and Analysis of Stably Transfected Established Cell Lines Carrying MUC5B Promoter Reporter Constructs This example describes the stable transfection of the −4,169/+7 MUC5B-luciferase and MUC5B-GFP reporter constructs (i.e., the constructs described in EXAMPLE 7) into the established TBE cell line HBE1.

Experimental—The established cell line HBE1 was cultured in 35 mm dishes and grown to 60–80% confluence. These cells were cotransfected with either MUC-5B reporter construct and a second plasmid encoding the neomycin-resistance (neo) selectable marker. The chimeric reporter plasmids used in the transfections were purified using QIAGEN® plasmid isolation kits, and the cotransfections were done using Roche FuGENE 6™ transfection reagent (Roche Molecular Biochemicals, Indianapolis, Ind.) according to the manufacturer's instructions. In these transfections, 2.5 µg of MUC5B reporter plasmid DNA and 0.5 µg of the neomycin resistance marker plasmid per 35 mm culture dish were used for each transfection.

Following the cotransfection, cells were cultured for an additional 48 to 72 hours. At this time, the medium was replaced with fresh medium containing the neomycin analogue G-418 at a concentration of 100 µg/ml. The selection was maintained for approximately 21 days, at which time clones of resistant transfected cells were replated and maintained as continuous lines. Cell extracts were prepared and luciferase activity quantitated exactly as described in EXAMPLE 8, with the exception that cell extracts were normalized for total protein content, and not β-galactosidase activity. In addition, these cells were cultured in the absence or presence of IL-6 (10 ng/ml) or IL-17 (10 ng/ml). It was observed that these cells expressed detectable luciferase activity, and this activity is upregulated when cells are cultured in the presence of IL-6 or IL-17.

All of the references identified herein, including patents, patent applications, and publications, are hereby incorporated by reference in their entireties.

While the invention has been described with an emphasis upon preferred embodiments, it will be obvious to those of ordinary skill in the art that variations in the preferred method, compound, and composition can be used and that it is intended that the invention can be practiced otherwise than as specifically described herein. Accordingly, this invention includes all modifications encompassed within the spirit and scope of the invention as defined by the following claims.

SEQUENCE LISTING

<160> NUMBER OF SEQ ID NOS: 36

<210> SEQ ID NO 1
<211> LENGTH: 48
<212> TYPE: DNA
<213> ORGANISM: Homo sapiens

<400> SEQUENCE: 1
tgtggtcagc tttgtgagga tccaggtcgt ccccggagtg gaggaggg         48

<210> SEQ ID NO 2
<211> LENGTH: 48
<212> TYPE: DNA
<213> ORGANISM: Homo sapiens

<400> SEQUENCE: 2 agggcagaa gttgtgctcg ttgtgggagc aggggttgtg ctggttgt           48

<210> SEQ ID NO 3
<211> LENGTH: 48
<212> TYPE: DNA
<213> ORGANISM: Homo sapiens

<400> SEQUENCE: 3
tgtggtcagc tctgtgagga tccaggtcgt ccccggagtg gaggaggg         48

<210> SEQ ID NO 4
<211> LENGTH: 4180
<212> TYPE: DNA
<213> ORGANISM: Homo sapiens

<400> SEQUENCE: 4

```
ggagggcccc cagacctcag tttacccact ggcgacacag gggtgcctgc ctgtgccctc      60
ccggccgggc gcaagcagtg gtgggcccag tggtctcgta gtctggggtc ggtgtgagtt     120
ccggttctcc aggcttttt ccagacaact gctgggattg gtgggcgaga ccaaggctca     180
tcaaaggcac agccttgggg gcaggatccc caccatgagt cagaggtagt tctggggagc     240
ctgggcaggc tgtcacctcc tcagctgtca ggcccgaggt cctcatgtgg tccccaggag     300
aaggggcaga cggccacttc cggccaccag ccagctccct gtgtgcctga ttccgtaaca     360
tgtcccctgg ctgggcatgt actccccaag ttctaattac atgtaactgc agagaagggc     420
tcagcctggg aaaaggatgg gcataggggg tggttggggg ctggggcctc tgacacagct     480
ccatgagccc ggccaagagt cccacacaag tcagtggccc cccggaccc tgaaggatcc     540
cacatcctcc ctgcccttgg ggaggcccct ttctggggtc aggcctggaa gctgccccag     600
agcttgggcc ccaggaatgg gttggtcctc ccagcgtaac gtgagcctga tcaggcctgg     660
ggacctgctc agcgggtgtc tgggggccca tggcgggcta aggagcctga ccagacttgc     720
ttctggcagg acacccctcc cccggccacc ctgggctcgc ccctctagta gctgcatgtg     780
ttccccgggt gtgtgttggc attcaggcta cagggctgcc tcatcctgaa gaaggctgcg     840
tttacccagg gagccataaa gagatgacct ccgataacct gaatcaatat ttccccattg     900
gggctcgggc cccgcagct gtcttcttga tcatctggca gatgccacac ccacccttgg     960
ccctcccctg ccttcctgcc ctcctaccct cctgccagga catataagga ccagaccct    1020
gcccccgggc gcaacccaca ccgcccctgc cagccaccat ggggctgcca ctagcccgcc    1080
tggcggctgt gtgcctggcc ctgtctttgg caggggctc ggagctccag acaggtgaga    1140
gagcagacac agggtctgg ggcctggcag agtgtcctgg gggcagggcg aggcgggcgg    1200
gcaagtcgcg tctgggagga ggagctggtc ccagagtgca gcctgcgcgg ctctgctgag    1260
gctcctggcc cgggttggtc cctggaagcc cccggccctg ctgactttca aggagctgga    1320
aggtcggggc tccctgcta ttcctttggg tttgactgcc cgacgacagt gtgggtcttg    1380
gggccagcac caggtggaaa cagcaggtca ggccccagtg aactgggtca ttgtccatag    1440
gggaggaagg ggtggccagg atcccaccag aaggcccat tctcaggtgg cagagaccct    1500
tgaagagttg gggcagcaca gcccttgctg gggagcgggg tgcccagaat gccctctcct    1560
acatcccgct tggcacccgg ccgcactcct caccaggccg ggggtagaag ccctgagacc    1620
cctgtggtgg ggtgaccaag gcccagcaga gggcccgagg ataggaagga acctttcccg    1680
gccaggggcc ctgtgctggg ctcgaagctg cttccaggtg cttcttcagg ggccttctcg    1740
agggtagctt gggcagcctt ccccctccgg gccactcacc cctcattccc cgctgctccc    1800
tcagagggca gaacccgaaa ccacggccac aacgtctgca gcacctgggg caacttccac    1860
tacaagacct tcgacgggga cgtcttccgc ttccccggcc cctgcgacta caacttcgcc    1920
tccgactgcc gaggctccta caaggaattt gctgtgcacc tgaagcgggg tccgggccag    1980
gctgaggccc ccgccggggt ggagtccatc ctgctgacca tcaaggatga caccatctac    2040
ctcacccgcc acctggctgt gcttaacggg gccgtgtgag tgtggtcggt ggcacccctc    2100
ccacatccta gcaacggggg ctgatgtttc ccaaagggat attccttgta gccctagaag    2160
accccttccg ccccagcaca cagctcagga gaacagcctt gaggtttggg ttcaggtcac    2220
taattcattc aacaaacact gatgagcccc caccattccc cccataggca aggggtttca    2280
gttatccctt tgcctgtgtg tccctgacag cccctcccct cggagccctc caggctccgg    2340
```

-continued

| | |
|---|---|
| acagacttgg cacccctgga ggctgcatgt ctctggtcct gtgcatggag tggccgtgtg | 2400 |
| tgccctcccc aggctagagt tacagaagcc ggtgcagggg gctgtgggac cccttcccc | 2460 |
| atccccagct attgctcccc tattgtctcc agaacaatga ggccctgtaa gtgcgttccc | 2520 |
| atccagcgcc tgcccctctt ctgcctgggg atttagtttc ctgcaagggg ccccagcatg | 2580 |
| ggcatgggca ggcgggtgga ggccctcagg catgggcatg gcaggcggg tgggtagagg | 2640 |
| ccctcaggcg tgagtgcggg cgggtgggtg gatagaagcc gtcacggatg ggtgcaggcg | 2700 |
| ggtgggtaga ggtcctcagg tgtgggcatg ggcaggtggg tgggtagagg gcgtcaggtg | 2760 |
| tgggcgcggg tgggtgggta gaggccctca ggcatgggtg caggcgggtg ggtgggtaga | 2820 |
| ggccctcagg cgtgggcgcg ggtggtgga tagaggccgc tacgggtagg tgcgggcggg | 2880 |
| tgggtagagg tcctcaggtg tgggcgcagg tgggtgggtg ggtagaggcc ctcaggcatg | 2940 |
| gcacaggtgg gtgggtagag gccctcaggc atgggcgcag gtgggtgggt gggtaggggc | 3000 |
| cctcaggcat gggtgttggc aggtgggtgg gtagaggctt tcaggcatgg gcaggcaggt | 3060 |
| agaggcccctt gaggaccgag gcacagaggc tgggtgagt gcctctacct ggaccagcaa | 3120 |
| ggggcactgg caggaggtgg ggtagggccc ctgacgttct caggggcagc ctgggggct | 3180 |
| ctgggggtt tgggacccca tgggggatg ttccaccaag caggggcct ggaagggggc | 3240 |
| tgggcagcct ggtccctcct ctcccaacct ggtgccctca gggcctctga gggggaccc | 3300 |
| tgcccaggac cgtgcccga ggagggagtg gagaggaggg gcgtgcaggc aggaggtggc | 3360 |
| tctgccgggg aagcccggc agcggagatg gacaggtgct ctttggccac tgcctatgtc | 3420 |
| cctccacccc agaggccggc caagttggtg atcccagggc aggagctggg cctggcagag | 3480 |
| ccatctccac caccccaggt gcccagcttc agtcccctct gggcggcggg gtcccgggag | 3540 |
| gacaagctgg ggcggggggg cctgggtggt ggacccaaga gtgaccccga tgtgcctccg | 3600 |
| ccagggtcag caccccgcac tacagccccg ggctgctcat tgagaagagc gatgcctaca | 3660 |
| ccaaagtcta ctcccgcgcc ggcctcaccc tcatgtggaa ccgggaggat gcactcatgg | 3720 |
| tgctcagggg tccccggact cgtggggctg gtggggctc cgtcaggcct ctgggcagac | 3780 |
| cccaagggag ggcagggagg gcagtgctct gacccctcac cgagagggca tgggtggggc | 3840 |
| agggcctcgg cagcgcgggg cgtcggtgct ggacttgggg ggcagcagca gaagccgacc | 3900 |
| tggccctgac ccccccaggc ctcagccttc ccccaaacgc actcggcttc tcagggacct | 3960 |
| gccctgccag gccgctccct ggctgctgac cccagccttc ctgccccacc ttcctctggc | 4020 |
| tcaaacaagc cacgagtctt ggggttcct ggcggctgtg ggccgggcgg gaggccagct | 4080 |
| cacctgctcc ctcccgcaac agctggagct ggacactaag ttccggaacc acacctgtgg | 4140 |
| cctctgcggg gactacaacg gcctgcagag ctattcagaa | 4180 |

<210> SEQ ID NO 5
<211> LENGTH: 1668
<212> TYPE: DNA
<213> ORGANISM: Homo sapiens

<400> SEQUENCE: 5

| | |
|---|---|
| tgtgctccag cctggagctg tacgcggcac tctgcgcgtc ccacgacatc tgcatcgatt | 60 |
| ggagaggccg gaccggccac atgtgcccat tcacctgccc agccgacaag gtgtaccagc | 120 |
| cctgcgcccc gagcaacccc tcctactgct acgggaatga cagcgccagc ctcgggctc | 180 |
| tgccggaggc cggcccccatc accgaaggct gcttctgtcc ggagggcatg accctcttca | 240 |

```
gcaccagtgc ccaagtctgc gtgcccacgg gctgccccag gtgtctgggg ccccacggag      300
agccggtgaa ggtgggccac accgtcggca tggactgcca ggagtgcacg tgtgaggcgg      360
ccacgtggac gctgacctgc cgacccaagc tctgcccgct gccccctgcc tgcccctgc       420 ccggcttcgt gcctgtgcct gcagccccac aggccggcca gtgctgcccc cagtacagct      480
gcgcctgcaa caccagccgc tgccccgcgc ccgtgggctg tcctgagggc gcccgcgcga      540
tcccgaccta ccaggagggg gcctgctgcc cagtccaaaa ctgcagctgg acagtgtgca      600
gcatcaacgg gaccctgtac cagcccggcg ccgtggtctc ctcgagcctg tgcgaaacct      660
gcaggtgtga gctgccgggt ggcccccat cggacgcgtt tgtggtcagc tgtgagaccc       720
agatctgcaa cacacactgc cctgtgggct tcgagtacca ggagcagagc gggcagtgct      780
gtggcacctg tgtgcaggtc gcctgtgtca ccaacaccag caagagcccc gcccacctct      840
tctaccctgg cgagacctgg tcagacgcag ggaaccactg tgtgacccac cagtgtgaga      900
agcaccagga tgggctcgtg gtggtcacca cgaagaaggc gtgccccccg ctcagctgtt      960
ctctggacga ggcccgcatg agcaaggacg gctgctgccg cttctgcccg ctgccccgc      1020 ccccgtacca gaaccagtcg acctgtgctg tgtaccatag gagcctgatc atccagcagc     1080
agggctgcag ctcctcggag cccgtgcgcc tggcttactg ccgggggaac tgtggggaca     1140
gctcttccat gtactcgctc gagggcaaca cggtggagca caggtgccag tgctgccagg     1200
agctgcggac ctcgctgagg aatgtgaccc tgcactgcac cgacggctcc agccgggcct     1260
tcagctacac cgaggtggaa gagtgcggct gcatgggccg cgcgctgccct gcgccgggcg    1320 acacccagca ctcggaggag gcggaacccg agcccagcca ggaggcagag agtgggagct     1380
gggagagagg cgtccagtgt cccccatgca ctgaccagca ctgccgccct cctgacctcc     1440
aaggagaacc tcccatatgt cctctgagct cggcttccaa ggccagtgga acttgtgccc     1500
ctgtccaggc ggctgcagct ttgaacacac tgtccacgcc cgctttcttg tggagggtgt     1560
gggctatggg tcacctgctg cctggaggag gggcccttac ccaccccgcc tgcagccacc     1620
tctcaggacc agccccgggg ctggccgagc tcctctggcc atgcatcc                  1668
```

<210> SEQ ID NO 6
<211> LENGTH: 22773
<212> TYPE: DNA
<213> ORGANISM: Homo sapiens

<400> SEQUENCE: 6

```
ggtaccctg gttgtgcctg tcgctcagtg ggccagggtc taagggctgt gaagactcaa       60
catgccccca cctgctactt ctgaacacca ggcactggct ctgagacccc cgggccttgc      120
tggacatctc cccaggtgta ctgggccagg ggacagggc ctggcatcc caacacccag       180 gagcaagcag cccgtcacct gcccaggtcc ccgaggcccg gaacaccttc ctgctgggcc     240 caccccagccc tggacctgtc ccgcttggtc acacgatggg accctcggcc catcagcagg    300 tgagcccca ggagcgtgcg tctggcctgg taaggcctcc accccaggag ttggggggcc      360
cccgtgccag ggagcaggag gctgccgagg tgagggtcc cacacagcta ccactcccta     420
tccccagcac agcctggggc ctggctctga gtacacatcc tggggcctgg ctctgagcag    480
accaagagcc catccctgct ttgtgacccc ctgggctgtg cctgacaccc caggtgtcca   540
gcgtggagct ggggcccagc tcagtgcctg ggagctgatg accctgggg cccggctcag    600 tgcctggtgg ctgatggaca ctggggcctg gctcaaacct gcaccgctgt ggtcggggga    660
ggggagggct gagccacgtg gggaacccag ccccagtgac gactctttgc ggtggccaag    720
```

```
ccctccaggt gtcccccagg gctgaggggc tgggcttggg gcagctggtg acagcagatg    780
gtggccctga tcactggtgc ctggacggcc tctgaagggg tctgtggggt cctggacggg    840
tccccattca tggcaggatt aaccccctc gggttctgtg tggtccaggc cgccccttg      900
tctccactgc cccctggcca gaatgaggga cagtgaccca cccagggctg ggcctggctc    960
agactccgtc agagccgcag ggcaagttcc tggcacgtcc gaggtgggag gctcctctgc   1020
gctccaggag gctgtgcctg gcccccttc ccggcaggaa ccggctgtgt ccctttcctt    1080
cctttatctt ctgttttcag cgccttcaac tgtgaagagg tgaactcttc aaacacgctg   1140
agcaaacagg cccgactccc agggccgcat ccgggatgtc tcaatagctg tggccttgac   1200
gtccacctcg gacccctgcc ccggacccag cccagttccc aatgggccct ctgcccgggg   1260
aggtgcctag tgggagggac gagggcaaag tcggggcccc cacttgtttg gtgtcactgt   1320
gtgccagcgg ccactggcgg gcgaggctgt tccaggtgg aggcggggag ggttggacca    1380
caggcactga gcgggacag aggagctgcc tgagggtccc agctctgcca tggagaaaac    1440
gctatctcgc tgatgcagag gtgcccggcc cactcgagct gggggtgagg gggctgctcc   1500
ccagtgggcc gccagccccc atgaaggccg cgggcaccgg ccgtggtcag ggagggcagg   1560
ggacaggcag tggggggccag caggggagac actaggcttg gccccagcac ccaggtgggc   1620
atcggcttgt gagctggagc cgcgggcagg gagggggat gtcacgaggg cttggctaag    1680
gtgggagacc tgggcgggtg cgtcgggggg acgtctgcag cagaggcctg ggcagcaggc   1740
acaccctcc tgccagtgcg aggaacgagg cgccacagcg gccggtagcc ccccatttgc    1800
ccagcctggc ctggagcagg caggaaggcc ggggagaggg gtctggctgg ggcctgggtg   1860
cagtcacagc cacgagccca ggggtgggga ctctggccca cccttcagac catgctcaag   1920
gcccactggc ccaggcatgc ccgccacccc ttccaccgtg ccgtgctgca gcgggtctac   1980
cggcctggat gtgaaagaga gcttggagac cccagagacc tcggaacctt cagctttgga   2040
agtgacgtcg gtgggtggg tggggggagc acaggctctg gagtcccgga agtgagcggg    2100
gagctacgct gagatctggg agacccctg ccccccaccca ggtacagggc caggcagaag   2160
cccgaggtgt gccctgagtt aaagaaaccg tcacaaagaa caagggaga aggcgggttc    2220
cagcctgcac cacagccctc gcgctctgag gagccacctg ggggcttcag ccatgagggg   2280
tgacaggtgg caaaacgggc cagctccgtt cacgtcgctg tgcagctgtc tccggccctc   2340
catctccaga acgttctcac attcccaagc tgaaaccctg tccccatgca acaccagctc   2400
accatcccct ctgccagccc ctggcgccca ccgtccacac tccgtctctg cgggtttcat   2460
gactccaggg gcagcacacg agtggcccct cctgcctttg tcctctgtgt ccacctgcct   2520
cactctgcac agtgtcccca gcttccccca tggagcagcc tgggccagcc cctccttttc   2580
acggctgaac cgtattccac cgcacggatc agcctcacga tgctgaccca gtcctccgcc   2640
cagggacaca tgggcagctt ctgcccttg tcagtgatgc tgctgtggac atgggtgtgc    2700
aaatgtccct caggacccgc cttcagttct tctggggaca gacccagagt ggagttgctg   2760
gtcaccccca ccagcagggc acagggctcc gggtccccac gtctctgcca acacttccta   2820
cttcctgtgt ttcttgatcc ccgccatcct attgagcgtg agacaggtca gaagctttga   2880
agatgggctt tcgtcttgtc ccagaaatcc cacctctaag aatttaactt cagaaagaca   2940
aacgcggggg agctggtgca gggcccgtga cggggactgt gacgtaaata aaacaacaga   3000
cctggacacc accctagggt ccccatgggg ccggacgagg ccacaccacc cgacctggtg   3060
```

-continued

```
cttcctgcct ggcgtctgcg ccacggagca ttcaggacgc tggtgaccag ggagccagga    3120
ggtgggagca tctgaggtgc aggtcacacg ggcaggaggt gtttgcaaga ggtattgcag    3180
cgcggacgga gtgtcctgca gatgacgctg tctgtcctgt agatgacgct cgtcaaggag    3240
gtttaccaca tagcccccgg gaagcccacc caacaccagc cggaggtgct aggcttctgc    3300
ggctcccacc tggggcaggc ggaggacccc gggcaggtcc aggacccccc ggagcagctg    3360
cttcctcaac cctgccaggg ttaatgagga ggccccagag tgaggtggag gccaaatggg    3420
actcagggcc ggagcctctg gcctggctgg atcagggctg gcattggaca gcgcagctg    3480 actcccgatg tgcatggcca ggagacactc tgggcctcag tttcccttg aatgtgaacc    3540 ttgaaacaga tcagcccaga gacctcccac ggtcttcaag gggctctggt cagctgggct    3600
ggggtctctg gaaatagagc ctcctccagg gaccccaca agccacccag actgagcatc    3660
ctggccatgt gcatgcctga gctcagcagg agcctgccgg gctcccgtg ggctaagcag    3720 tggtgggagg ggagctccag cctcgtgggc cctgcccggg cctcggggac ccatggtcag    3780
tggctggggg tgctgcccag aggctgggat tcccttccag caggagccgc agtggggctg    3840
agtgtgaggc aggctggctg accactgttt ccatggaccc tgcgtccaag gccagccctg    3900
ccttccagcg gctttgccat ctaggacggg tgccaggtgg ggtaggccct tctctccctt    3960
ccgattctca gaagctgctg ggggtggggg cgtcctgggc ctcagggcac agagctgcaa    4020
atccttcctg atccaggcct ctcccctgcc acagcccctc cccgagagca acacacgtg    4080 gctggagcgg ggaagagcac ggtgccctgc gtggcctggc ctggcttggg gccaaggctc    4140
cctgctacat aagctggggc ccccagggga gcaagcaccc ggcccggctc cctccctgcc    4200 cgtcccgtc cccccacccg tgccagcccc caggatgggt gccccgagcg cgtgccggac    4260
gctggtgttg gctctggcgg ccatgctcgt ggtgccgcag gcaggtaaga gcccccccact    4320 ccgccccctc tcgatgctgt cttcacgcg ggggtctctg caggtcgctt gcctgggagc    4380
ttctcctgca gagtgcacgg gcagatcccc ctacgactcc ctgagtgtcc tggatgggac    4440 cctaccgtc cccaacacag ggctctgggg ccccacgggc tcacagtgtc aggaaactca    4500
ggggctggct tggatgggt gtccaggaga aggtgggccc ctgaccgcag ggcaaggccc    4560 ctggagacc accgaaaggg tcttggtctt ggggtggga caggagtggg caatggggga    4620
gggggtcaca gctggggtc tctctggagc cccatgaggc ccaggcatca gagtgagcag    4680
gggcaggctt agcgtggacc cctgtccagg accggctcta cccttcacga cctccctggg    4740
gatcacagct ggcagggcag gtgagggtac ccgggaccct caagggttgc acagccagcc    4800
gcaagagccc cggcctcaac ccacgctcga ctcccacggc ccatctgtgg gcatctcatg    4860
ccgcacgggc tgcctggctc tcagccgagc gttttccctc gtctgctgtc tcttggccag    4920
agccgcagca ttaatactta ctgtcaatag agaaagatgc agcccaggg gccaccggga    4980 gacacccagc caggctggcc atgaggctgc tgcagcccct ccctgccccg ccctccgccc    5040
cctcccaagc ttggggtctg ggctgggcag gtgaggttcc ctgggtctc tctccatctg    5100 tggaagggag gctgggtggt cagcagggct ggagcaggg ggcttccccc agtggctccc    5160
agcctgggcc cgggggagc tgcgtctggc tgcaaggttt gggggctggt ttgaccagaa    5220
tagccacctc cttgcatctg attcttccgg gccatgcagc cttggctccc ctcacctgag    5280
caggcagggc ctagggactc tcagcccacc cgtcctcctg tcctccacgc acgtccaagt    5340 tgggagatc aagcccttgg caggactgt gctttagtca ccagatgcac gtcctgtggc    5400
cggggaaggc agccctgcac agagcagctt catgttaggg gacacacccc aaagtgatgg    5460
```

-continued

```
ggtggctggt ggtgggcact tctctggcta caagatggag gcccaggtgg tccagcccaa   5520
ggagggcact gcacggagca gataaccaag ggcagtcagc ctgggcaggg gagggctgc    5580 ctgggggga  ggggttgcct gggttgggga ggggctgtct gggcagggg  aggagctgcc   5640 tgggcgggg  gaggggctgt agggccaggg aggggctgcc tggggctggg gagggctgc    5700 tggggtgggg aggggctgcc tgcggcggga gccggggcgt gggagtggct ggttgggctg   5760
gcacacaggg gcagggctgt gagctgtggg tcggggtgga ggactcaggg atcggctggc   5820
tttctgggaa aggcagtcaa cctggatctc tggaggcggc ccctgtggtg gttcccagat   5880
gtcagcagga cctggctgga aaagccaggc agggccaggc cagagtgcga accacagggc   5940
cggcccctcg ctgagccctg accatgcttg tggggctgg  ggcctcacct cccacctccc   6000
cacagagagt ctcagatcag gatccaggga ggagctctgg ggtcctgtga aggggcgcc    6060 ccaacccaaa ctgggcagac aatgccgggg ggtcctcaga gtcctgtggg ttggagctgc   6120
ctcctcccag cctccatggg gttggtgggt gaggccttgc ccggaggcgg tggtcagcct   6180
ggggaccttt gggcggccat cccagtatca acggccacac agcttgcgcg cccagagtc   6240 ctgcccccag cctgccccac tcgccctgac ttaggatcta gttcgaaact ggttctgtgt   6300
ttaggtttct gctaagtcac gcctggaagg ctccaagtgt gtcctcctaa caaagctggt   6360 cttttgtcctt ctccaaggga tgtgtgggat ggggcgaaat ccccccttgg ggcggccaac  6420 gcctttttcct gattccattt tctcccccat cccttgagaa ggaggcacca tcccgcctg   6480 tcagtcgggg acagggcagg ccgtgctggg ggcagctcag ggctccctgc tggaagcttc   6540
catcccgcag gctttccata gcattgagca ggagcggagg catctgcggc tgacggttgg   6600
ggtggcctga gcggctgggg aggagtcccg gccttggcca cagtgtgtcg tgagggtgaa   6660
cctgcagggc atggagaccg ccaccaagga ccccacatgc ggctgccgca ccagggatgt   6720
ggccaggtcc gtggttgggt tcgtggctgg cagccacatc tagttcctca ctgactccca   6780
ttccctcttc ccacagagac ccagggccct gtggagccga gctgggggaa tgcagggcac   6840
accatggatg gcggtatgtg gccaggttcg ggggtggggg gttcctgacc aggctggagg   6900
ggctggaatt tgggctgggg caggcagacg cctctccaag cagccatgcg tctgacagag   6960
accctccctg gtcccctgc  ccaggacaat acccagcacc cgaggcggag cttggtgctc    7020
caaagaagag gaaagtgcag agcagagaga catgcacaca gaagcacacg cgtggacagg   7080
cacatgcgtg cccacactta cactggcaca cacatgtgtg cacacacagg ccaaaacaca   7140
agggcagcag tgtttgtggg gcagacaggg ccaagggtaa aggggctgcc ttggccccag   7200
cccatcagtt ttgggctccc cttcaactct ggtggctggc gaggagggtg ggccccgggg   7260
agggtgtctc tgcttcccct tcctggccac gttcctgggg tgaccagcct tcacccacag   7320
gtgccccgac gtcctcgccc acccggcgcg tgagctttgt tccacccgtc actgtcttcc   7380
ccagcctgag ccgtaagcag atgctgcccc tgccagccgg gaagggggtg tttgccagtc   7440
ccaaaggtgg gggcccagat ctaggggtgc agctgccacc aggtggggcc gttgggccag   7500
acccagagtc ctccgtgtgg gcggtctcct ggtcactggc caccctgggg gatggggacg   7560
ggtcaggggt cttggagcaa acagacgca  gtccagggtg agccaggcag ggcacagcca   7620
gcagccgacc atgggctttt ccattccaaa aaccagggtg cctcggccca ggggaggcta   7680
ccccgtgggg ggctggcatg gggatgggcc tcatcccgcg ctcccacag  ccctgaaccc   7740 ggcgcacaat gggcgggtgt gcagcacctg gggtgacttc cactacaaga ccttcgacgg   7800
```

-continued

```
cgacgtcttc cgcttccctg gcctttgcaa ctacgtgttc tctgagcact gccgcgccgc    7860
ctacgaggac ttcaacgtcc agctacgccg aggcctagtg ggctccaggc ctgtggtcac    7920
ccgtgttgtc atcaaggccc aggggctggt gctgaaggcg tccaacggct ccgtcctcat    7980
caatgggcag cggtgagccg ccacccctgg ggaggggcga gggccgggcc acacagtgtg    8040
acctccccac acggccatgt ctgacctggg ccagggctgg ggtggggttg ggtgggcagg    8100
cagccaggag agcggggccc agggagagac cccgctgtct cgcagggag gagctgcctt    8160
acagccgcac tggcctcctg gtggagcaga gcggggacta catcaaggtc agcatccggc    8220
tggtgctgac attcctgtgg aacgagagg acagtgccct ggtgaggaag ccccctcgcc    8280
ccttgcccct tcaggcctgg ccacaaaacc cccaccgggg gtcgagggat gcctccctgg    8340
gcttggggtc acgggcttg gggcatgttg ccagtggggg gatcagaggt cctgaggctg    8400
gagctgcccc tccccactct cagctggagc tggatcccaa atacgccaac cagacctgtg    8460
gcctgtgtgg ggacttcaac ggcctccgg ccttcaacga gttctatgcc cacagtgagt    8520
gccacctggg tgagggggcg gtgaccaatt atgtcggcca acgaagagcc acagtcccgg    8580
ggaggccggg aggggcgga gtggggaccg ggcaccaggc agggaggggc cacgaggact    8640
gtgccctaca tggtgggagg agtgcccctc ggggtgttg ggccctaggc aggagtggga    8700
gtcctctggc ctgggctcag gaagtgggag cccatatctt gtccccagga gcccctcaga    8760
gccaccacac ccctgctttc ttcccggcag acgccaggct gaccccgctc cagtttggga    8820
acctgcagaa gttggatggg cccacagagc agtgccgga cccgctgccc ttgccggccg    8880
gcaactgcac ggacgaggtg agtcccccgc cacccccagc tcctgggcag ggacggcctc    8940
caggtccagg gggagctggg ccgaggtctg aggaatgttc ccagctggtg gagagatggt    9000
gccattggag ggaggccggg cagccaccct ctgtgtgctc agttccacgg tacacactgt    9060
ccgagtgtgg tgacgtgcgt gttcatcagg ccacgcgtgt gcccatctgt gtgagcaaac    9120
acaggcccat gctgcacagg ctgggctgag ggtgggcact cgggaagccc ggagccagcc    9180
cttcccacca gcaggtggac tcagaagggg cctggaggct ccaggatccc caaaccagca    9240
ggatctctga gccttaaatt gtgctgtgaa tgacagcatg agccccctg tgagctgggc    9300
cccgcagccg gcagccctgg gcctggggac ggaggacact cagcactgga ctgccctgaa    9360
cctgccgggc tgcccagaga ggcggggcct ccacctcccc tccttggctc cgcctcctgg    9420
ggtgggggtc tgcaccttc ttgggcgctt actccacggg caggcacatc cggagtaggg    9480
gatcccgggt tgacgggtca ctccccaagg gccaagcaga gctctgcatg gccacagtgg    9540
gtggaagggg tggggctggg tacaaggaac cccgacaggg agagggcttc ccggcctggc    9600
ctgccatggg tcctattcca gcaccgtggc agccccatg gatggcaggg gtgcccagcc    9660
tggcccactg tgctccccag gagggcatct gccaccgcac cctgctgggg ccggcctttg    9720
cggagtgcca cgcactggtg gacagcactg cgtacctggc cgcctgcgcc caggacctgt    9780
gccgctgccc cacctgcccg tgtgccacct ttgtggaata ctcacgccag tgcgcccacg    9840
cgggggggcca gccgcggaac tggaggtgcc ctgagtctg ccgtgagtgc tcccagggcc    9900
ttcgccaggg attgtgccag agagaagggg caggggagc gccttggggg ccactgggg    9960
tggggaggcc tggggacag gggtggaggg cagaggaccc accccaggca tagtgggcag   10020
aggccacccc aggaccccag gaggggtgg ggccgccggg ggctgcaggg gaaggagagg   10080
cttgtgagaga ggcttgtgca gcaggtggca ggggctgggg ctgagggtg tagctgccca   10140
cgatgagggg cgtcagggcc accctggggc ctagctctgg cttctgtgga cttgatggca   10200
```

-continued

```
tgtggaaggc cgtggaaggc ggctggggct gaccacacgg gcagtacagg gcccttcccc    10260
tggcccagcc ccgcctcctt tgcgcagcc cggacctgcc ccctcaacat gcagcaccag     10320
gagtgtggct caccctgcac ggacacctgc tccaaccccc agcgcgcgca gctctgcgag    10380
gaccactgtg tggacggctg cttctgcccc ccaggcagtg cttgtgtgcc ctgaacccct    10440
caggggggctt tcaggtccct gctcccaacc ccgcccccag cctcatcagg cctggaagca   10500
gagcccctca tgccagaagg tcccaccaga gggcccaggg tgggaagggc actggctggg    10560
agggtgctgg aagacctgcc gatgcgtgga gggaggtaga gcagtgccat gagccagctg    10620
ggcatggtgg ggaaactgag gcccagaggt gcttggtgtt catccaagcg agtgcagctc    10680
agggcgggg  cagtgtcctg gagcaggaat tcctccccaa gggaggcagc ttgtccccaa    10740
ggccggtgtc ttctgacctt ggtgtccccc gtgcatgggc cggccctgcc tcacgccgcg    10800
ccccacaggc acggtgctgg atgacatcac gcactctggc tgcctgcccc tcgggcagtg    10860
cccctgcacc cacggcggcc gcacctacag cccgggcacc tccttcaaca ccacctgcag   10920
ctcctggtac ttatgagccc accagcctcc gcctggggtg gggtgtggag ctcctggtat    10980
ttatgaaccc gccagcctct gcctggggtg ggggtgtgga gctcctggtg tgcacccacc    11040
agcctccgcc tgcggtgggg gtgtggaggg tggggcccac ctcctcccga catgccggtt    11100
ctgctcacgg cctccctccc cagcacctgc tccgggggc tatggcagtg ccaggacctg     11160
ccgtgccctg gcacctgctc tgtgcagggc ggggcccaca tctccaccta tgatgagaaa   11220
ctctacgacc tgcatggtga ctgcagctac gttctgtcca aggtctgggc ttggggccgg    11280
gtcttcagac acccagaccc tcctgggacc ctcatgccac ttccacccag gggaggcccc    11340
cacgatggtc atagaggggt ggatgtccct gctgaggggg gagccctggg tccccatgat    11400
ggtcatagag ggatggctct ccctgctgag cggcatgggg ccaaggagcc cccaggccct    11460
gagacaagct gctgggaggt gaccagaggt gccaaggacc acctcccac  agagccacat    11520
cccccacatg ggcatcccca gcacacttct gggggcacc ccacatcatc gagccaggcc     11580
caatgcacgc gtgggtcctt ctccccagaa atgtgccgac agcagcttca ccgtgctggc    11640
tgagctgcgg aagtgcggcc tgacggacaa cgagaactgc ctgaaagcgg tgacgctcag    11700
cctggacggc ggggacacgg tgaggacctg gctgggcccc tgggctggga caggaagagg   11760
catgcgaagg tgtgtgggga gcaagcacgg tcaggtcccc ctccagcccc gaggccaggt    11820
ccccctcca gccccaggc caggtccccc tccagccccc aggtcaggtc ccccctccag      11880
ccctgaggtc aggtcctccc gggggggcaa ttgcagagcc caccgcaggt ccaggcctga   11940
gcttctctgt gggctctgtc cccagtgggg gcccctgggc aggccacccc ctcatttgag   12000
agtcgggaat gggttcctcc ccagagctga cctcccgccc gcctccttcc gcaggccatc   12060
cgggtccaag cggacggcgg cgtgttcctc aactccatct acacgcagct gcccctgtcg    12120
gcaggtatgt ggctctccca ggacggccgg gctggtgggc gcctgcttgc aggggcagct    12180
cccacagcct gggcagcgtc cgctccatcc ctgctagttc tccgtggcct cgggcagctc    12240
caggagctcc ctgtgctcgg tttctcgtct gcagagtggg gatgccaggc tcccaccccg    12300
gcagcggcag ggaccccaca tccagctcgc tcagccccac tctctcaggg agccggtct    12360
ccacctgagc ccacttggcg gccacaggca tgggacaggg agcctgaggg ctcctggcca   12420
ctcctgggtc tcactcccgg gtctcagtgg ggtggcccgg cccactggat gccctgcccc   12480
tccaatctag ccagatctgt ccctgcaccc ctgaccggcc tctcccccac actcccggca    12540
```

```
gccaacatca ccctgttcac accctcgagc ttcttcatcg tggtgcagac aggcctcggg   12600
ctgcagctgc tggtgcagct ggtgccactc atgcaggtgt ttgtcaggct ggaccccgcc   12660
caccagggcc agatgtgcgg tgaggctggg caggggcctt cggggacagg gccattgggg   12720
acggggcctg gactagcgcc aggctgcagg gaggggcagg cagaggcggg caggggaccg   12780
gggagggggc tgcccccagg gcatggcgga gatcctggtg ccagcgcagg acaccagcat   12840
tggaccagcg gccccggaag cagccagctg ggaggatgga gcgggcagcc ctgccctggc   12900
tcaggccgac tttgcacagg ggctggcttt gcacaggggc cgactgcaca ggggcgcccc   12960
ccgccagggc ttatctgcag agggttctgg agcagaatc ctgggacagg gctcccagcc   13020
gttctaccct gtgtggtgcc tggagggatg gcaggggcca ggagccaggt gggcccaaca   13080
gtggccgctg acatccccca accctggccc ccaggcctgt gtgggaactt caaccagaac   13140
caggctgacg acttcacggc cctcagcggg gtggtggagg ccacgggcgc agccttcgcc   13200
aacacctgga aggcccaggc tgcctgtgcc aatgccagga acagctttga ggaccctgc    13260 tccctcagtg tggagaatgg tactcctcgc ccccaccccc acagtcaccc caggctcaag   13320
tcccacccag caccttcctg tccctgggc cacggggacc cctgggtggg attggggacc    13380
ccatggaggc aggtgggagg catcaggagg aggtgcttgg ggccaggcgg ccagaacccc   13440
ccaaggcgca gcaggtgagc cgcaaattcc aactcactgt tccccgggct gagggggtcg   13500
caggcctgcg tgtcaggggt gtgggcttcg gggcagggcg tggagatgag gtcaggtctt   13560
ccccacagag aactacgccc ggcactggtg ctcgcgcctg accgatccca acagtgcctt   13620
ctcgcgctgc cactccatca tcaaccccaa gccttccac tcggtgagag gctgaggcca    13680
gacccccacg cctgggcagg atgggtgggg gagccctggc aggctggggt ccctgacgcc   13740
ccgacgcctc ccacctccgc agaactgcat gtttgacacc tgcaactgtg agcggagcga   13800
ggactgcctg tgcgccgcgc tgtcctccta cgtgcacgcc tgtgccgcca agggcgtaca   13860
gctcagcgac tggagggacg gcgtctgcag tgagtgccca cgctgggggt gggatgtgtc   13920
cacaccgcgt gggggtgcgg gggaccctgg ccggcagcag ccgtcactca cacggttctc   13980
agcccagagc tttgcacttc ctcatcccag cctcgcaaga acctcatgcc cttgcgatcc   14040
ccacgtcaca gacggggatg ctgagttgaa gatgggggct ggccaggctg ctcggccgct   14100
gacctgtccc ccctggcccc accgaccaca gccaagtaca tgcagaactg ccccaagtcc   14160
cagcgctacg cctacgtggt ggatgcctgc cagcccactt gccgcggcct gagtgaggcc   14220
gacgtcacct gcagcgtttc cttcgtgcct gtggacggct gcacctgccc cgcgggcacc   14280
ttcctcaatg acgcgggcgc ctgtgtgccc gcccaggagt gccctgcta cgctcacggc    14340 accgtgctgg ctcctggaga ggtggtgcac gacgagggcg ccgtgtggta agggtctggg   14400
gggaaagcag gccccccagg tgctcctcag agccacttcc cgccctcccc gaaggcttct   14460
gtgcctcccc ccgagggttc tgagacacga ggggccaggc tggggagagt ggggcagggt   14520
ggacccagca cattctgaag agaaaattcc cagctgggaa agaggccagg agaggaggtg   14580
gccctgggag gacacctgct ggctgttctc agctgggtcc acatggcagc ccctgccagg   14640
aaaggtgggt ggcccccact cccaccctgg gctcaaaggc cgctcctaac cccagggtcc   14700
tggctgcttt gctgccccc tgtgtgtatt tacccatgtg cctccagggg atttgggggc    14760
tcccagcaaa cacagcagca ggcaccgtct ggccttacaa ggaggtggcc aggctgggga   14820 gcccagcat tcggcggggg ctcggaagcc cggggtggg gtctgcgggg tgaggccgc      14880 agatccaggc tgtgccgtct gtctcttgta gttcatgtac gggtgggaag ctaagctgcc   14940
```

-continued

```
tgggagcctc tctgcagaaa agcacaggta agtgccaccc ctgccctgcc ctgccccgcc    15000
ccgcatcacc ccgcctggcc tggccccaac acgccccacc ctgccccacc ccacctgaac    15060
cctgccgggc caggtcagtc ctcacctggg ctctgccaca ggcacccatg ccctgacacg    15120
ccagggacgg aggggccagt gggtctctgc cccgcagtgt ggccggggtg tcctggggtt    15180
gggggctgca ggtgtcatgg aagctttggc tcgggggctg ttaacttgat cagcaggaca    15240
ggctcagggc tgcctggggt cagttgaggg ccgtggctgc ccttccccag gaccccatcccc   15300 accaagctct gtccccaggg tgtgcagccc ccatggtgta cctggactgc agcaacagct    15360
cggcgggcac ccctggggcc gagtgcctcc ggagctgcca cacgctggac gtgggctgtg    15420
tgagttccat gcttcaggga ggggtgggca gggaagggggt cccagctttc ccagctcccg    15480
agcccaggga tctggtggtc ctggagacac ttacccacct ggaagctccg ccctggccca    15540
tgcgttgccc tgggtgctgc tgggtgcgcc tgtcccagag ggtgagtgac atctgcccac    15600
cctggtgtcc agccctgacc ggtacctgcc tgggcccac agttcagcac acactgcgtg     15660
tccggctgtg tctgtccccc ggggctggtg tcggatggga gtgggggctg cattgccgag    15720
gaggactgcc cctgtgtgca caacgaggcc acctacaagc ctggagagac catcagggtc    15780
gactgcaaca cctggtgggt cgtgagtctc tcggaggcag caggtgggga gggcggggc     15840 ggggagggca gcgggtgggg aggcagcggg caggagggc aggggcggg gagggcaggg     15900 ggccagctgg ccagggtgag gtggggccgt ggcaggagag agagttgcta ggaaagccat    15960
gggccgtcct gtgcgtcctc tggaaggtgg cccaggggcc atggtgctac caggagcctg    16020
gtggggctgc gtgccctgca ttcacagtgg gggacaccac ttcttccacg gaggaggggt    16080
caggctgggc ctggggaggc tgaggccccg tgctgacctg cacaggcctg ggtgccgggt    16140
ctcaggaagg ccgggagagc aggcccctgt gagcaggcac cattgtggcc ccttgcagca    16200
cctgcaggaa ccgggaggtgg gagtgcagcc accggctctg cctgggcacc tgcgtggcct    16260
acggggatgg ccacttcatc acctttgatg gcgatcgcta cagctttgaa ggcagctgcg    16320
agtacatctt ggcccaggta cgccgccccc tcgcccactc ctgcaggccg gcacactcc     16380 agcccgcggc cagcagcttg tctctttctg gcccaggact actgtgggga caacaccacc    16440
cacgggacct tccgcatcgt caccgagaac atccctgtg ggaccaccgg caccacctgc    16500
tccaaggcca tcaagctctt cgtggaggtg agaacggccc cagctgtgag caccccgac     16560 cctgcagcca acgagccggc ccccagggaa gcttcgtgag gctttagctg cacccacagg    16620
ttctcagcag tgtcctggcc ccgggctgct gttccaagca gccacaaacc aggggggctta    16680 gacaacagaa atgcattctc agtcctggag ccggaagtca gagatccagg cgggcagggc    16740
cacactccct gtcgagggtc tggggaggtc cttcctgcct ctcccagctt cacaggcggc    16800
aggcgtccct gggctgtggc tgcctgtggc ctcccgctgt gtctgcgtct gtcttctctc    16860
tgtttttctc ttctgtctct tgtaaggaca ctggtcattg gatttagggc cccccccgc    16920 ccccacgtag tccaggatga tctcatttca agatgcttca cttaatcccg tctgcagaga    16980
tgctttctcc cagtgagggc ccgggctgag gttctggag ttcgcatgtg acaggcatt     17040 ttcaggagcc acgattcacc ctgccacacc tagagacacc cactccagca aaggggggcc    17100
agagctccca ggggataaag cagcgccgct ggccgggatg ctccctgcag atggcgggag    17160
gggctgagga ccgcagcggg tcaggggagg ctggtgtgag ggcgtggggg ctgcagggct    17220
ggatggggag caggtggggg tggagtgggc ctactgcagc ctctgctgct cccgtgcagc    17280
```

```
cccaaggttc ccaggcagcc cctgttccca gcacttcctg gccagcctct tgccaaacct    17340
tcactgaggg tctcacggac ccagctcacc cctaacgcca gccgcttgtg ctaagagccc    17400
gtgcgcacct gcagagcact gggtggggca tccctgggtc tcaggcccct ccctgggggc    17460
cacagggtcg gcttccggca gcgtctgcct ccctgcaga gctacgagct gatcctccaa    17520
gaggggacct ttaaggcggt ggcgagaggg ccgggtgggg acccacccta caagatacgc    17580
tacatgggga tcttcctggt catcgagacc cacgggatgg ccgtgtcctg ggaccggaag    17640
accagcgtgt tcatccgact gcaccaggac tacaaggtga gctcgggccg tgcactccta    17700
ggccctgcag gaccctctca cagtgacaga aaccctggtg ccaggtgggg cctgtgggac    17760
tcgctgaccc gtgggtgcgt gagcctggct ggtgagggcc ctgcctgtgg cctccacagt    17820
gggcagagga ttttgcaggg aagcaggtgc cacccagcgg cccacccagg acccactgc    17880 acacctgtct cctacaagtt caccaggcac tgcctgggga accggctgcc ctccctccat    17940
cccccgaggg ctctggagcc cagggtgggc tctgtgctgc ctcccacggg tgcctgtggc    18000
cccagctcca gggccccact ctctcgctgc ctctgcaggg cagggtctgc ggcctgtgcg    18060
ggaacttcga cgacaatgcc atcaatgact ttgccacgcg tagccggtcc gtggtggggg    18120
acgcactgga gtttgggaac agctggaagc tctcccccctc ctgcccggac gccctggcac    18180
ccaaggaccc ctgcacggcc aaccccttcc gcaagtcctg ggcccagaag cagtgcagca    18240
tcctccacgg ccccaccttc gccgcctgcc gctcccaggt ggggctctgg tcttggcagg    18300
cagggtctgg tggggatggc agttgcttcc ttcccgccga gaactgggtc ttctgggcag    18360
acagcagcgc tccaaggagg gtctgaccat gtcccacggc acacagtcct ggatgtcagg    18420
tcccaagtcc ggatctcccg tcagccccac acctgtgcct cttgcccctg gcacgaagcc    18480
atcttggctg tttccggcc actcctttga ccacagcctc agtcacaccc agaggctcac    18540
agggaggggc agccctctat gtgggcccta gccaccctcc tctatgatcc ccagacctgc    18600
ccagtcctca gcacaaactg gaatgccagc ctggctcccc gctcagccag ggaggaatca    18660
gagatctgcc ctaagcagag acttccgaaa agcagtttcc tgactgggcg cggtggctca    18720
tgtctgtaat cccagcactt tgggacgctg aggcaggtgg atcacctgag gtcaggagtt    18780
tgagaccagc ctggtcaaca tggcgaaacc ccgtctctac aaaaaataca aaaatagccg    18840
ggtgtggtgg tgtgtgcctg taatcccagc tactcgggag gctgaggcag gagaatcact    18900
tgaacctggg aagaggaggt tgcagtgagc caagatcgtg ccactgcact ccagcctaag    18960
caaaaagagt gagactctgt ctcaaaacaa aacaacaaaa aaccaaaaag cagtttcgtg    19020
tcatcttaag gaagacttga gtgcccactt aggcacacag catggtggct caggagctga    19080
gatgaggggc tggcgtaggg gcagcagtgg gcatactcgc tcgtgggagg ccctgaagca    19140
ctctcatgtc ggccgccgct tgcccctctt gagaaggcagc tggtgacccc ttggaaggtc    19200
ctgtggcctg acaaagctga gcccaggttc agatggggcc tgggagggt gtgggctgcc    19260 tggaggaagc aggcagcttc ccatggtcag gacgcattca cagctcagct ccccgcgtgg    19320
ctggtctgga aaggaagtga ccactccttc cttagtgcac attcactggg tgcctggaat    19380
agcctggcat gttctgggct caccccagtg atcagggac gaggctgacc ctcacagagc    19440
ttccagagga ggcagaaagg cggtgggtgc tgggtggtcg gatgctagga tgtgagggc    19500 cctggccggg ggttggttcc gctggaggga aggcccccag gtggaaagga ggccagtacg    19560
actgcagcgg agggaggtgg gggcgagggc agagggtaag caggggtgct atgctccaca    19620 tgggttttgaa acctgtgggc cacatgacca gatccacgtg atagaaagat ccaaagagca    19680
```

-continued

```
catgtgaagg caggcagatg ggcaggtgca taggtgggca ggtgcatagg tgggcagatg      19740
gacaggtggg cagatgggca ggtgggcagg gatataggtg gacgagggca caggtgggct      19800
ggagaagtgc tggggcagct cccatttggg gcacgctctg aggtattcca ggccccagga      19860
gctcagagag ctgccatggg gggtgttgaa atacagatgg ttccagcaac tggccctggg      19920
ccagccaccc cctggccggg ggggccattg tcccggctga gctgcacctt ggcctcaccc      19980
gcaggttgac tccaccaagt actacgaggc ctgcgtgaac gacgcgtgtg cctgcgactc      20040
gggtggcgac tgcgagtgtt tctgcacggc tgtggctgcc tacgcccagg cctgccacga      20100
cgcgggcctg tgtgtgtcct ggcggactcc ggacacctgc cgtgagtcgg gctctgtccg      20160
tggtgctgaa gggtggagct gctggggcag gggaggaggt gtggcagcct ccgaaggtgc      20220
attgacctgg gcctgagccg cacacagaca tccaacacgc atgtgcctcc atgtgagtgc      20280
acaagtttct atgcacagag gaagacctgt gcaaaaccac cagacaggtt gccccagcat      20340
gagacagctc ctaggggaca agagttccaa gggcagggct ggggagtgga ggggaaggtg      20400
aggcaccacc cggccgaggc cctgcatgtc tgggacaagc ccgggtctgg ctctggggac      20460
accggccccc acgcccgggg tagggctgc cctgcacaac aggggtgagg gctggtggcg      20520
cctccttagc ctctgccctc tgtgcccag  ccttgttctg tgacttctac aacccacatg      20580
ggggctgtga gtggcactac cagccctgcg ggcaccctg  cctaaaaacc tgccggaacc      20640
ccagtgggca ctgcctggtg gacctgcctg gcctggaagg tgaggggcag cctttcttgg      20700
atggagcctc ctctccttgg gttcccgagt gtacgtgggg gggcggggat ccccagggac      20760
gcggtgtagg ctcccgtaaa ctgcacaatg caagccttga gggcaggccc ctgctggctg      20820 gtgggggcg  gctactccct gcagcatgga gcccctggct ggagagacta aagggccctg      20880
gtgagtcttc tgctcaccct gccggcccta ggctgctacc cgaagtgccc acccagccag      20940
cccttcttca atgaggacca gatgaagtgc gtggcccagt gtggctgcta cgacaaggac      21000
ggaaactact atgacgtcgg tgcaagggtc cccacagcgg agaactgcca gagctggtga      21060
gggggtggga agcgggtggc gctggggagg cagggctggg gagcaggccc tgcaggctgc      21120 ccccaggcc ctcagctcgc ctctccccca cccctagtaa ctgcacaccc agtggcatcc      21180
agtgcgctca cagccttgag ggtaaggaag gccggggggg ttagtgggcc ggtgaaggct      21240
ggggccaggg gctcggaggc cctgggtgac tctgccggct ccatcccag  cctgcacctg      21300 cacctatgag gacaggacct acagctacca ggacgtcatc tacaacacca ccgatgggct      21360 tgcgcctgc  ttgatcgcca tctgcggaag caacggcacc atcatcagga aggctgtggc      21420
atgtcctgga actccagcca caacgccatt caccttcacc accgcctggg tcccccactc      21480
cacgacaagt aagccctgcc tggctctcct gaggcccagt actgtctggg tgacaaggag      21540
gaccccctgg gctcttagtg caggtgccct gtatggtagc gacagtccca atccactgac      21600
cttccgggct ctgtctaggg gtgcacggcc cctcaacacc ctgcgtgtct ccagggcctc      21660
cccacgaagc ctcagcacaa tgattgatgg gatacccaa  ggagacaata aagctttcct      21720
ggactccgtc ccatccctca gcacggccta tcccagccag ccagctccct caaggccagg      21780
ctgccaggcc ccagtccctc atgcagaaac ggctctaacc aaggctgagg caggcactgg      21840
ggtccccagt atcccacagg ggcagggcca gccctgggga aagggtcctc tggggcccct      21900
ccaccttgtg aggccaggac tggaggatgc tgagccagga ccccttccc  atgcccttg       21960 caggcccggc cctcccggtc tccaccgtgt gtgtccgcga ggtctgccgc tggtccagct      22020
```

-continued

```
ggtacaatgg gcaccgccca gagcccggcc tgggaggcgg agactttgag acgtttgaaa    22080
acctgaggca gagagggtac caggtatgcc ctgtgctggc tgacatcgag tgccgggcgg    22140
cgcagcttcc cgacatgccg ctggaggagc tgggccagca ggtggactgt gaccgcatgc    22200
gggggctgat gtgcgccaac agccaacaga gtcccccgct ctgtcacgac tacgagctgc    22260
gggttctctg ctgcgaatac gtgccctgtg gccctcccc ggcccaggc accagccctc     22320 agccctccct cagtgccagc acggagcctg ctgtgcctac cccaacccag accacagcaa    22380
ccgaaaagac caccctatgg gtgaccccga gcatccggtc gacggcggcc ctcacctcgc    22440
agactgggtc cagctcaggc cccgtgacgg tcaccccctc ggcccaggt accaccacct     22500 gccagccccg gtgtcagtgg acagagtggt ttgatgagga ctaccccaag tctgaacaac    22560
ttggagggga cgttgagtcc tacgataaga tcagggccgc tggagggcac ttatgccagc    22620
agcctaagga catagagtgc caggccgaga gcttccccaa ctggaccctg gcacaggtgg    22680
ggcagaaggt gcactgtgac gtccacttcg gcctggtgtg caggaactgg gagcaggagg    22740
gcgtcttcaa gatgtgctac aactacagga tcc                                22773
```

<210> SEQ ID NO 7
<211> LENGTH: 19
<212> TYPE: DNA
<213> ORGANISM: Homo sapiens

<400> SEQUENCE: 7

```
gcggcaccac gagcatggc                                                 19
```

<210> SEQ ID NO 8
<211> LENGTH: 20
<212> TYPE: DNA
<213> ORGANISM: Homo sapiens

<400> SEQUENCE: 8

```
gcggtgccca ttgtaccagc                                                20
```

<210> SEQ ID NO 9
<211> LENGTH: 20
<212> TYPE: DNA
<213> ORGANISM: Homo sapiens

<400> SEQUENCE: 9

```
tggaccagcg gcagacctcg                                                20
```

<210> SEQ ID NO 10
<211> LENGTH: 22
<212> TYPE: DNA
<213> ORGANISM: Homo sapiens

<400> SEQUENCE: 10

```
cagtcaccat gcaggtcgta ga                                             22
```

<210> SEQ ID NO 11
<211> LENGTH: 20
<212> TYPE: DNA
<213> ORGANISM: Homo sapiens

<400> SEQUENCE: 11

```
tcataggtgg agatgtgggc                                                20
```

<210> SEQ ID NO 12
<211> LENGTH: 25

```
<212> TYPE: DNA
<213> ORGANISM: Homo sapiens

<400> SEQUENCE: 12
gtggaagggc ttgggggttg atgat                                   25

<210> SEQ ID NO 13
<211> LENGTH: 22
<212> TYPE: DNA
<213> ORGANISM: Homo sapiens

<400> SEQUENCE: 13
gagaaggcac tgttgggatc gg                                      22

<210> SEQ ID NO 14
<211> LENGTH: 22
<212> TYPE: DNA
<213> ORGANISM: Homo sapiens

<400> SEQUENCE: 14
tgggcataga actcgttgaa gg                                      22

<210> SEQ ID NO 15
<211> LENGTH: 20
<212> TYPE: DNA
<213> ORGANISM: Homo sapiens

<400> SEQUENCE: 15
gttgaagtcc ccacacaggc                                         20

<210> SEQ ID NO 16
<211> LENGTH: 20
<212> TYPE: DNA
<213> ORGANISM: Homo sapiens

<400> SEQUENCE: 16
ggtctggttg gcgtatttgg                                         20

<210> SEQ ID NO 17
<211> LENGTH: 21
<212> TYPE: DNA
<213> ORGANISM: Homo sapiens

<400> SEQUENCE: 17
ctggggaaga cagtgacggg t                                       21

<210> SEQ ID NO 18
<211> LENGTH: 21
<212> TYPE: DNA
<213> ORGANISM: Homo sapiens

<400> SEQUENCE: 18
cgggtggaac aaagctcacg c                                       21

<210> SEQ ID NO 19
<211> LENGTH: 21
<212> TYPE: DNA
<213> ORGANISM: Homo sapiens

<400> SEQUENCE: 19
ctgtggagcc gagctggggg a                                       21

<210> SEQ ID NO 20
```

```
<211> LENGTH: 39
<212> TYPE: DNA
<213> ORGANISM: Artificial Sequence
<220> FEATURE:
<223> OTHER INFORMATION: Synthetic primer comprising Homo sapiens
      sequence and an artificial tail
<220> FEATURE:
<221> NAME/KEY: unsure
<222> LOCATION: 39
<223> OTHER INFORMATION: v is a or g or c

<400> SEQUENCE: 20
gaccacgcgt atcgatgtcg acttttttttt tttttttttv                39

<210> SEQ ID NO 21
<211> LENGTH: 39
<212> TYPE: DNA
<213> ORGANISM: Artificial Sequence
<220> FEATURE:
<223> OTHER INFORMATION: Synthetic primer comprising Homo sapiens
      sequence and an artificial tail
<220> FEATURE:
<221> NAME/KEY: unsure
<222> LOCATION: 39
<223> OTHER INFORMATION: v is a or g or c

<400> SEQUENCE: 21
gaccacgcgt atcgatgtcg acaaaaaaaa aaaaaaaav                  39

<210> SEQ ID NO 22
<211> LENGTH: 24
<212> TYPE: DNA
<213> ORGANISM: Homo sapiens

<400> SEQUENCE: 22
gtggaagggc ttggggttga tgat                                  24

<210> SEQ ID NO 23
<211> LENGTH: 22
<212> TYPE: DNA
<213> ORGANISM: Homo sapiens

<400> SEQUENCE: 23
gagaaggcac tgttgggatc gg                                    22

<210> SEQ ID NO 24
<211> LENGTH: 20
<212> TYPE: DNA
<213> ORGANISM: Homo sapiens

<400> SEQUENCE: 24
gggcccacat ctccacctat                                       20

<210> SEQ ID NO 25
<211> LENGTH: 26
<212> TYPE: DNA
<213> ORGANISM: Artificial Sequence
<220> FEATURE:
<223> OTHER INFORMATION: Synthetic primer comprising Homo sapiens
      sequence and an engineered terminal restriction site

<400> SEQUENCE: 25
aaggatccgg gtgcttgctc ccctgg                                26

<210> SEQ ID NO 26
<211> LENGTH: 25
<212> TYPE: DNA
```

```
<213> ORGANISM: Artificial Sequence
<220> FEATURE:
<223> OTHER INFORMATION: Synthetic primer comprising Homo sapiens
      sequence and an engineered terminal restriction site

<400> SEQUENCE: 26
aagctagcgc cacggagcat tcagg                                          25

<210> SEQ ID NO 27
<211> LENGTH: 26
<212> TYPE: DNA
<213> ORGANISM: Artificial Sequence
<220> FEATURE:
<223> OTHER INFORMATION: Synthetic primer comprising Homo sapiens
      sequence and an engineered terminal restriction site

<400> SEQUENCE: 27
aaggatccgg gtgcttgctc ccctgg                                         26

<210> SEQ ID NO 28
<211> LENGTH: 28
<212> TYPE: DNA
<213> ORGANISM: Artificial Sequence
<220> FEATURE:
<223> OTHER INFORMATION: Synthetic primer comprising Homo sapiens
      sequence and an engineered terminal restriction site

<400> SEQUENCE: 28
aagctagcct ggttgtgcct gtcgctca                                       28

<210> SEQ ID NO 29
<211> LENGTH: 28
<212> TYPE: DNA
<213> ORGANISM: Artificial Sequence
<220> FEATURE:
<223> OTHER INFORMATION: Synthetic primer comprising Homo sapiens
      sequence and an engineered terminal restriction site

<400> SEQUENCE: 29
aaagatctcc aaattccagc ccctccag                                       28

<210> SEQ ID NO 30
<211> LENGTH: 25
<212> TYPE: DNA
<213> ORGANISM: Artificial Sequence
<220> FEATURE:
<223> OTHER INFORMATION: Synthetic primer comprising Homo sapiens
      sequence and an engineered terminal restriction site

<400> SEQUENCE: 30
aagctagcca ggggagcaag caccc                                          25

<210> SEQ ID NO 31
<211> LENGTH: 1105
<212> TYPE: DNA
<213> ORGANISM: Homo sapiens

<400> SEQUENCE: 31
gcgccacgga gcattcagga cgctggtgac cagggagcca ggaggtggga gcatctgagg    60
tgcaggtcac acgggcagga ggtgtttgca agaggtattg cagcgcggac ggagtgtcct   120
gcagatgacg ctgtctgtcc tgtagatgac gctcgtcaag gaggtttacc acatagcccc   180
cgggaagccc acccaacacc agccggaggt gctaggcttc tgcggctccc acctggggca   240
ggcggaggac cccgggcagg tccaggaccc cccggagcag ctgcttcctc aaccctgcca   300
```

-continued

```
gggttaatga ggaggcccca gagtgaggtg gaggccaaat gggactcagg gccggagcct      360
ctggcctggc tggatcaggg ctggcattgg acaagcgcag ctgactcccg atgtgcatgg      420
ccaggagaca ctctgggcct cagtttcccc ttgaatgtga accttgaaac agatcagccc      480
agagacctcc cacggtcttc aagggctct ggtcagctgg ctggggtct ctggaaatag       540 agcctcctcc agggaccccc acaagccacc cagactgagc atcctggcca tgtgcatgcc      600
tgagctcagc aggagcctgc cgggctcccc gtgggctaag cagtggtggg aggggagctc      660
cagcctcgtg ggccctgccc gggcctcggg gacccatggt cagtggctgg ggtgctgcc      720 cagaggctgg gattcccttc cagcaggagc cgcagtgggg ctgagtgtga ggcaggctgg      780
ctgaccactg tttccatgga ccctgcgtcc aaggccagcc ctgccttcca gcggctttgc      840
catctaggac gggtgccagg tggggtaggc ccttctctcc cttccgattc tcagaagctg      900 ctggggtgg gggcgtcctg ggcctcaggg cacagagctg caaatccttc ctgatccagg      960
cctctcccct gccacagccc ctccccgaga gcaaacacac gtggctggag cggggaagag     1020
cacggtgccc tgcgtggcct ggcctggctt ggggccaagg ctccctgcta cataagctgg     1080
ggcccccagg ggagcaagca cccgg                                           1105
```

<210> SEQ ID NO 32
<211> LENGTH: 4176
<212> TYPE: DNA
<213> ORGANISM: Homo sapiens

<400> SEQUENCE: 32

```
cctggttgtg cctgtcgctc agtgggccag ggtctaaggg ctgtgaagac tcaacatgcc      60
cccacctgct acttctgaac accaggcact ggctctgaga cccccgggcc ttgctggaca     120 tctcccagg tgtactgggc caggggacag gggcctggcc atcccaacac ccaggagcaa      180
gcagcccgtc acctgcccag gtccccgagg cccggaacac cttcctgctg ggcccaccca     240
gccctggacc tgtcccgctt ggtcacacga tgggaccctc ggcccatcag caggtgagcc     300
cccaggagcg tgcgtctggc ctggtaaggc ctccaccca ggagttgggg ggcccccgtg      360
ccagggagca ggaggctgcc gaggtggagg gtcccacaca gctaccactc cctatccca     420 gcacagcctg ggcctggct ctgagtacac atcctgggc ctggctctga gcagaccaag      480
agcccatccc tgctttgtga ccccctgggc tgtgcctgac accccaggtg tccagcgtgg     540
agctggggcc cagctcagtg cctgggagct gatggaccct ggggcccggc tcagtgcctg     600
gtggctgatg gacactgggg cctggctcaa acctgcaccg ctgtggtcgg ggagggggag     660
ggctgagcca cgtggggaac ccagcccag tgacgactct tgcggtggc caagccctcc      720 aggtgtcccc caggggctgag gggctgggct tggggcagct ggtgacagca gatggtggcc     780
ctgatcactg gtgcctggac ggcctctgaa ggggtctgtg gggtcctgga cgggtcccca     840
ttcatggcag gattaacccc cctcgggttc tgtgtggtcc aggccgcccc tttgtctcca     900 ctgcccctg gccagaatga gggacagtga cccacccagg gctgggcctg gctcagactc      960
cgtcagagcc gcaggcaag ttcctggcac gtccgaggtg ggaggctcct ctgcgctcca     1020
ggaggctgtg cctggccccc cttcccggca ggaacggct gtgtcccttt ccttccttta     1080
tcttctgttt tcagcgcctt caactgtgaa gaggtgaact cttcaaacac gctgagcaaa     1140
caggcccgac tcccagggcc gcatccggga tgtctcaata gctgtggcct tgacgtccac     1200
ctcggacccc tgcccggac ccagcccagt tcccaatggg ccctctgccc ggggaggtgc     1260
ctagtgggag ggacgagggc aaagtcgggg cccccacttg tttggtgtca ctgtgtgcca     1320
```

-continued

```
gcggccactg gcgggcgagg ctgttccagg gtggaggcgg ggagggttgg accacaggca    1380
ctgagcgggg acagaggagc tgcctgaggg tcccagctct gccatggaga aaacgctatc    1440
tcgctgatgc agaggtgccc ggcccactcg agctgggggt gaggggctg ctccccagtg     1500 ggccgccagc ccccatgaag gccgcgggca ccggccgtgg tcagggaggg caggggacag    1560
gcagtggggg ccagcagggg agacactagg cttggcccca gcacccaggt gggcatcggc    1620
ttgtgagctg gagccgcggg cagggagggg ggatgtcacg agggcttggc taaggtggga    1680
gacctggggc ggtgcgtcgg ggggacgtct gcagcagagg cctgggcagc aggcacaccc    1740
ctcctgccag tgcgaggaac gaggcgccac agcggccggt agccccccat ttgcccagcc    1800
tggcctggag caggcaggaa ggccggggag aggggtctgg ctggggcctg ggtgcagtca    1860
cagccacgag cccagggggtg gggactctgg cccaccccttc agaccatgct caaggcccac   1920
tggcccaggc atgcccgcca ccccttccac cgtgccgtgc tgcagcgggt ctaccggcct    1980
ggatgtgaaa gagagcttgg agaccccaga gacctcggaa ccttcagctt tggaagtgac    2040
gtcggtgggg tgggtggggg gagcacaggc tctggagtcc cggaagtgag cggggagcta    2100
cgctgagatc tgggagaccc cctgccccca cccaggtaca gggccaggca gaagcccgag    2160
gtgtgccctg agttaaagaa accgtcacaa agaacaaagg gagaaggcgg gttccagcct    2220
gcaccacagc cctcgcgctc tgaggagcca cctgggggct tcagccatga ggggtgacag    2280
gtggcaaaac gggccagctc cgttcacgtc gctgtgcagc tgtctccggc cctccatctc    2340
cagaacgttc tcacattccc aagctgaaac cctgtcccca tgcaacacca gctcaccatc    2400
ccctctgcca gccccctggcg cccaccgtcc acactccgtc tctgcgggtt tcatgactcc    2460
aggggcagca cacgagtggc ccctcctgcc tttgtcctct gtgtccacct gcctcactct    2520
gcacagtgtc cccagcttcc cccatggagc agcctgggcc agcccctcct tttcacggct    2580
gaaccgtatt ccaccgcacg gatcagcctc acgatgctga cccagtcctc cgcccaggga    2640
cacatgggca gcttctgccc tttgtcagtg atgctgctgt ggacatgggt gtgcaaatgt    2700
ccctcaggac ccgccttcag ttcttctggg acagaccca gagtggagtt gctggtcacc     2760
cccaccagca gggcacaggg ctccgggtcc ccacgtctct gccaacactt cctacttcct    2820
gtgtttcttg atccccgcca tcctattgag cgtgagacag gtcagaagct ttgaagatgg    2880
gctttcgtct tgtcccagaa atcccacctc taagaattta acttcagaaa gacaaacgcg    2940
ggggagctgg tgcagggccc gtgacgggga ctgtgacgta aataaaacaa cagacctgga    3000
caccacccta gggtccccat ggggccggac gaggccacac cacccgacct ggtgcttcct    3060
gcctggcgtc tgccgcacgg agcattcagg acgctggtga ccaggagcc aggaggtggg     3120 agcatctgag gtgcaggtca cacgggcagg aggtgtttgc aagaggtatt gcagcgcgga    3180
cggagtgtcc tgcagatgac gctgtctgtc ctgtagatga cgctcgtcaa ggaggtttac    3240
cacatagccc ccgggaagcc cacccaacac cagccggagg tgctaggctt ctgcggctcc    3300
cacctggggc aggcggagga ccccgggcag gtccaggacc cccgagca gctgcttcct      3360 caaccctgcc agggttaatg aggaggcccc agagtgaggt ggaggccaaa tgggactcag    3420
ggccggagcc tctggcctgg ctggatcagg gctggcattg acaagcgca gctgactccc     3480 gatgtgcatg gccaggagac actctgggcc tcagtttccc cttgaatgtg aaccttgaaa    3540
cagatcagcc cagagacctc ccacggtctt caagggctc tggtcagctg ggctggggtc     3600
tctggaaata gagcctcctc cagggacccc cacaagccac ccagactgag catcctggcc    3660
```

| atgtgcatgc | ctgagctcag | caggagcctg | ccgggctccc | cgtgggctaa | gcagtggtgg | 3720 |
| gagggggagct | ccagcctcgt | gggccctgcc | cgggcctcgg | ggacccatgg | tcagtggctg | 3780 |
| ggggtgctgc | ccagaggctg | ggattcccctt | ccagcaggag | ccgcagtggg | gctgagtgtg | 3840 |
| aggcaggctg | gctgaccact | gtttccatgg | accctgcgtc | caaggccagc | cctgccttcc | 3900 |
| agcggctttg | ccatctagga | cgggtgccag | gtggggtagg | cccttctctc | ccttccgatt | 3960 |
| ctcagaagct | gctgggggtg | gggcgtcct | gggcctcagg | gcacagagct | gcaaatcctt | 4020 |
| cctgatccag | gcctctcccc | tgccacagcc | cctccccgag | agcaaacaca | cgtggctgga | 4080 |
| gcggggaaga | gcacggtgcc | ctgcgtggcc | tggcctggct | tggggccaag | gctccctgct | 4140 |
| acataagctg | ggcccccag | gggagcaagc | acccgg | | | 4176 |

<210> SEQ ID NO 33
<211> LENGTH: 2751
<212> TYPE: DNA
<213> ORGANISM: Homo sapiens

<400> SEQUENCE: 33

| ccaggggagc | aagcacccgg | cccggctccc | tccctgcccg | tccccgtccc | ccacccgtg | 60 |
| ccagccccca | ggatgggtgc | cccgagcgcg | tgccggacgc | tggtgttggc | tctggcggcc | 120 |
| atgctcgtgg | tgccgcaggc | aggtaagagc | ccccactcc | gccccctctc | gatgctgtct | 180 |
| tcacggcggg | ggtctctgca | gtcgcttgc | ctgggagctt | ctcctgcaga | gtgcacgggc | 240 |
| agatccccct | acgactccct | gagtgtcctg | gatgggaccc | tacccgtccc | caacacaggg | 300 |
| ctctggggcc | ccacgggctc | acagtgtcag | gaaactcagg | ggctggcttg | gatgggtgt | 360 |
| ccaggagaag | gtgggcccct | gaccgcaggg | caaggcccct | gggagaccac | cgaaagggtc | 420 |
| ttggtcttgg | gggtgggaca | ggagtgggca | atggggagg | gggtcacagc | tgggggtctc | 480 |
| tctggagccc | catgaggccc | aggcatcaga | gtgagcaggg | gcaggcttag | cgtggacccc | 540 |
| tgtccaggac | cggctctacc | cttcacgacc | tccctgggga | tcacagctgg | cagggcaggt | 600 |
| gagggtaccc | gggaccctca | agggttgcac | agccagccgc | aagagccccg | gcctcaaccc | 660 |
| acgctcgact | cccacggccc | atctgtgggc | atctcatgcc | gcacgggctg | cctggctctc | 720 |
| agccgagcgt | tttccctcgt | ctgctgtctc | ttggccagag | ccgcagcatt | aatacttact | 780 |
| gtcaatagag | aaagatgcag | ccccaggggc | caccgggaga | cacccagcca | ggctggccat | 840 |
| gaggctgctg | cagcccctcc | ctgccccgcc | ctccgcccccc | tcccaagctt | gggtctggg | 900 |
| ctgggcaggt | gaggttccct | ggggtctctc | tccatctgtg | gaagggaggc | tggtggtca | 960 |
| gcagggctgg | aggcaggggg | cttcccccag | tggctcccag | cctggcccg | ggggagctg | 1020 |
| cgtctggctg | caaggtttgg | gggctggttt | gaccagaata | gccacctcct | tgcatctgat | 1080 |
| tcttccgggc | catgcagcct | tggctcccct | cacctgagca | ggcagggcct | agggactctc | 1140 |
| agcccacccg | tcctcctgtc | ctccacgcac | gtccaagttg | gggagatcaa | gcccttggca | 1200 |
| gggactgtgc | tttagtcacc | agatgcacgt | cctgtggccg | gggaaggcag | ccctgcacag | 1260 |
| agcagcttca | tgttagggga | cacaccccaa | agtgatgggg | tggctggtgg | tgggcacttc | 1320 |
| tctggctaca | agatggaggc | ccaggtggtc | cagcccaagg | aggcactgc | acggagcaga | 1380 |
| taaccaaggg | cagtcagcct | gggcagggga | gggctgcct | ggggggagg | ggttgcctgg | 1440 |
| gttggggagg | ggctgtctgg | ggcagggag | gagctgcctg | gggcgggga | ggggctgtag | 1500 |
| ggccagggag | gggctgcctg | gggctgggga | ggggctgctg | gggtgggag | gggctgcctg | 1560 |
| cggcgggagc | cggggcgtgg | gagtggctgg | ttgggctggc | acacaggggc | aggctgtga | 1620 |

-continued

```
gctgtgggtc ggggtggagg actcagggat cggctggctt tctgggaaag gcagtcaacc    1680
tggatctctg gaggcggccc ctgtggtggt tcccagatgt cagcaggacc tggctggaaa    1740
agccaggcag ggccaggcca gagtgcgaac cacagggccg gcccctcgct gagccctgac    1800
catgcttgtg ggggctgggg cctcacctcc cacctcccca cagagagtct cagatcagga    1860
tccagggagg agctctgggg tcctgtgaag ggggcgcccc aacccaaact gggcagacaa    1920
tggccggggg tcctcagagt cctgtggggtt ggagctgcct cctcccagcc tccatggggt    1980
tggtgggtga ggccttgccc ggaggcggtg gtcagcctgg gggaccttgg gcggccatcc    2040
cagtatcaac ggccacacag cttgcgcggc ccagagtcct gcccccagcc tgccccactc    2100
gccctgactt aggatctagt tcgaaactgg ttctgtgttt aggtttctgc taagtcacgc    2160
ctggaaggct ccaagtgtgt cctcctaaca aagctggtct ttgtccttct ccaagggatg    2220
tgtgggatgg ggcgaaatcc ccccttgggg cggccaacgc cttttcctga ttccattttc    2280
tcccccatcc cttgagaagg aggcaccatc cccgcctgtc agtcgggac agggcaggcc    2340 gtgctggggg cagctcaggg ctccctgctg aagcttcca tcccgcaggc tttccatagc    2400
attgagcagg agcggaggca tctgcggctg acggttgggg tggcctgagc ggctggggag    2460
gagtcccggc cttggccaca gtgtgtcgtg agggtgaacc tgcagggcat ggagaccgcc    2520
accaaggacc ccacatgcgg ctgccgcacc agggatgtgg ccaggtccgt ggttgggttc    2580
gtggctggca gccacatcta gttcctcact gactcccatt ccctcttccc acagagaccc    2640
agggccctgt ggagccgagc tgggggaatg cagggcacac catggatggc ggtatgtggc    2700
caggttcggg ggtgggggt tcctgaccag gctggagggg ctggaatttg g    2751
```

<210> SEQ ID NO 34
<211> LENGTH: 809
<212> TYPE: DNA
<213> ORGANISM: Homo sapiens

<400> SEQUENCE: 34

```
gcccggccct cccggtctcc accgtgtgtg tccgcgaggt ctgccgctgg tccagctggt      60
acaatgggca ccgcccagag cccggcctgg gaggcggaga ctttgagacg tttgaaaacc     120
tgaggcagag agggtaccag gtatgccctg tgctggctga catcgagtgc cgggcgcgc     180 agcttcccga catgccgctg gaggagctgg gccagcaggt ggactgtgac cgcatgcggg     240
ggctgatgtg cgccaacagc caacagagtc ccccgctctg tcacgactac gagctgcggg     300
ttctctgctg cgaatacgtg ccctgtggcc cctccccggc cccaggcacc agccctcagc     360
cctccctcag tgccagcacg gagcctgctg tgcctacccc aacccagacc acagcaaccg     420
aaaagaccac cctatgggtg accccgagca tccggtcgac ggcggccctc acctcgcaga     480
ctgggtccag ctcaggcccc gtgacggtca ccccctcggc cccaggtacc accacctgcc     540
agccccggtg tcagtggaca gagtggtttg atgaggacta ccccaagtct gaacaacttg     600
gaggggacgt tgagtcctac gataagatca gggccgctgg agggcactta tgccagcagc     660
ctaaggacat agagtgccag gccgagagct tccccaactg gaccctggca caggtggggc     720
agaaggtgca ctgtgacgtc cacttcggcc tggtgtgcag gaactgggag caggagggcg     780
tcttcaagat gtgctacaac tacaggatc                                        809
```

<210> SEQ ID NO 35
<211> LENGTH: 2143
<212> TYPE: DNA

<213> ORGANISM: homo sapiens

<400> SEQUENCE: 35

```
tgtgccctga gttaaagaaa ccgtcacaaa gaacaaaggg agaaggcggg ttccagcctg      60
caccacagcc ctcgcgctct gaggagccac ctgggggctt cagccatgag gggtgacagg     120
tggcaaaacg ggccagctcc gttcacgtcg ctgtgcagct gtctccggcc ctccatctcc     180
agaacgttct cacattccca agctgaaacc ctgtccccat gcaacaccag ctcaccatcc     240
cctctgccag cccctggcgc ccaccgtcca cactccgtct ctgcgggttt catgactcca     300
ggggcagcac acgagtggcc cctcctgcct ttgtcctctg tgtccacctg cctcactctg     360
cacagtgtcc ccagcttccc ccatggagca gcctgggcca gcccctcctt ttcacggctg     420
aaccgtattc caccgcacgg atcagcctca cgatgctgac ccagtcctcc gcccagggac     480
acatgggcag cttctgccct ttgtcagtga tgctgctgtg acatgggtg tgcaaatgtc      540
cctcaggacc cgccttcagt tcttctgggg acagacccag agtggagttg ctggtcaccc     600
ccaccagcag ggcacagggc tccgggtccc cacgtctctg ccaacacttc ctacttcctg     660
tgtttcttga tccccgccat cctattgagc gtgagacagg tcagaagctt tgaagatggg     720
ctttcgtctt gtcccagaaa tcccacctct aagaatttaa cttcagaaag acaaacgcgg     780
gggagctggt gcagggcccg tgacggggac tgtgacgtaa ataaaacaac agacctggac     840
accaccctag ggtccccatg gggccggacg aggccacacc accgacctgg tgcttcctgc     900
ctggcgtctg cgccacggag cattcaggac gctggtgacc agggagccag gaggtgggag     960
catctgaggt gcaggtcaca cgggcaggag gtgtttgcaa gaggtattgc agcgcggacg    1020
gagtgtcctg cagatgacgc tgtctgtcct gtagatgacg ctcgtcaagg aggtttacca    1080
catagccccc gggaagccca cccaacacca gccggaggtg ctaggcttct gcggctccca    1140
cctggggcag gcggaggacc ccgggcaggt ccaggacccc ccggagcagc tgcttcctca    1200
accctgccag ggttaatgag gaggccccag agtgaggtgg aggccaaatg ggactcaggg    1260
ccggagcctc tggcctggct ggatcagggc tggcattgga caagcgcagc tgactcccga    1320
tgtgcatggc caggagacac tctgggcctc agtttcccct tgaatgtgaa ccttgaaaca    1380
gatcagccca gagacctccc acggtcttca aggggctctg gtcagctggg ctggggtctc    1440
tggaaataga gcctcctcca gggaccccca caagccaccc agactgagca tcctggccat    1500
gtgcatgcct gagctcagca ggagcctgcc gggctcccg tgggctaagc agtggtggga     1560
ggggagctcc agcctcgtgg gccctgcccg ggcctcgggg acccatggtc agtggctggg    1620
ggtgctgccc agaggctggg attcccttcc agcaggagcc gcagtggggc tgagtgtgag    1680
gcaggctggc tgaccactgt ttccatggac cctgcgtcca aggccagccc tgccttccag    1740
cggctttgcc atctaggacg ggtgccaggt ggggtaggcc cttctctccc ttccgattct    1800
cagaagctgc tgggggtggg ggcgtcctgg gcctcagggc acagagctgc aaatccttcc    1860
tgatccaggc ctctcccctg ccacagcccc tccccgagag caaacacacg tggctggagc    1920
ggggaagagc acggtgccct gcgtggcctg gcctggcttg ggccaaggc tccctgctac     1980
ataagctggg gcccccaggg gagcaagcac ccggcccggc tccctccctg cccgtccccg    2040
tccccccacc cgtgccagcc cccaggatgg gtgccccgag cgcgtgccgg acgctggtgt    2100
tggctctggc ggccatgctc gtggtgccgc aggcagagac cca                      2143
```

<210> SEQ ID NO 36
<211> LENGTH: 25

-continued

```
<212> TYPE: PRT
<213> ORGANISM: Homo sapiens

<400> SEQUENCE: 36

Met Gly Ala Pro Ser Ala Cys Arg Thr Leu Val Leu Ala Leu Ala Ala
1               5                   10                  15

Met Leu Val Val Pro Gln Ala Glu Thr
            20                  25
```

What is claimed is:

1. A vector comprising a reporter gene operably linked to a regulatory region comprising a nucleotide sequence of SEQ ID NO: 31 or SEQ ID NO: 32.

2. The vector of claim 1 wherein said reporter gene encodes a polypeptide selected from the group consisting of luciferase, green fluorescent protein (GFP), chloramphenicol acetyl transferase (CAT), β-glucuronidase (GUS), secreted alkaline phosphatase (SEAP) and β-galactosidase (β-gal).

3. The vector of claim 2, wherein said vector is a cloning vector.

4. The vector of claim 2, wherein said vector is an expression vector.

* * * * *